US006924113B2

(12) United States Patent
Li

(10) Patent No.: US 6,924,113 B2
(45) Date of Patent: Aug. 2, 2005

(54) METHOD AND KIT FOR ISOLATING DNA PROBES THAT BIND TO ACTIVATED TRANSCRIPTION FACTORS

(75) Inventor: Xianqiang Li, Palo Alto, CA (US)

(73) Assignee: Panomics, Inc., Redwood City, CA (US)

( * ) Notice: Subject to any disclaimer, the term of this patent is extended or adjusted under 35 U.S.C. 154(b) by 365 days.

(21) Appl. No.: 09/877,738

(22) Filed: Jun. 8, 2001

(65) Prior Publication Data

US 2003/0022173 A1 Jan. 30, 2003

(51) Int. Cl.[7] .............................................. G01N 33/53
(52) U.S. Cl. ................................ 435/7.1; 435/6; 435/4; 435/DIG. 17; 435/DIG. 15; 435/DIG. 14; 536/23.1; 536/23.4; 536/22.1
(58) Field of Search ................. 435/7.1, 6, 4; 536/23.4, 536/23.1, 22.1

(56) References Cited

U.S. PATENT DOCUMENTS

| | | | |
|---|---|---|---|
| 5,403,712 A | 4/1995 | Crabtree et al. ............... | 435/6 |
| 5,563,036 A | 10/1996 | Peterson et al. ............... | 435/6 |
| 5,578,444 A | 11/1996 | Edwards et al. ............... | 435/6 |
| 5,738,990 A | 4/1998 | Edwards et al. ............... | 435/6 |
| 5,744,131 A | 4/1998 | Edwards et al. ......... | 424/78.08 |
| 5,747,253 A | 5/1998 | Ecker et al. ............... | 435/6 |
| 5,804,374 A | 9/1998 | Baltimore et al. ............ | 435/6 |
| 5,849,493 A | 12/1998 | Montminy et al. ............ | 435/6 |
| 5,859,227 A | 1/1999 | Giordano et al. .......... | 536/24.1 |
| 5,861,246 A | 1/1999 | Weissman et al. ............ | 435/6 |
| 5,908,750 A | 6/1999 | Reed et al. .................... | 435/6 |
| 5,981,188 A | 11/1999 | Barbosa et al. ............... | 435/6 |
| 6,040,138 A | 3/2000 | Lockhart et al. ............... | 435/6 |
| 6,051,373 A | 4/2000 | Green et al. .................... | 435/5 |
| 6,066,452 A * | 5/2000 | Weissman et al. ............ | 435/6 |
| 6,100,032 A | 8/2000 | Kern et al. ..................... | 435/6 |
| 6,100,035 A | 8/2000 | Kauffman et al. ............ | 435/6 |
| 6,150,090 A | 11/2000 | Baltimore et al. ............ | 435/6 |
| 6,153,383 A | 11/2000 | Verdine et al. ................ | 435/6 |
| 6,156,502 A | 12/2000 | Beattie .......................... | 435/6 |
| 6,156,511 A | 12/2000 | Schatz et al. .................. | 435/6 |
| 6,171,798 B1 | 1/2001 | Levine et al. .................. | 435/6 |
| 6,180,763 B1 | 1/2001 | Sherr et al. ................. | 530/413 |
| 6,183,956 B1 | 2/2001 | Sivaraja et al. ................ | 435/6 |
| 6,183,965 B1 | 2/2001 | Verdine et al. ................ | 435/6 |
| 6,194,171 B1 | 2/2001 | Pulst et al. ................ | 435/69.1 |
| 6,194,638 B1 | 2/2001 | Dhugga et al. ............ | 800/284 |
| 6,197,580 B1 | 3/2001 | Susulic et al. ............. | 435/325 |
| 6,537,749 B2 * | 3/2003 | Kuimelis et al. .............. | 435/6 |

FOREIGN PATENT DOCUMENTS

| | | | | |
|---|---|---|---|---|
| WO | WO 99/10535 | 3/1999 | ............ | C12Q/1/68 |
| WO | WO 00/04196 | 1/2000 | ............ | C12Q/1/68 |
| WO | WO 01/16605 | 3/2001 | .......... | G01N/33/68 |

OTHER PUBLICATIONS

Skov et al, Blood, 91, (10), (May 15, 1998), 3566–73.*

Klein, Joachim, "A New Family of DNA binding proteins includes putative transcriptional regulators of the *Antirrhinum majus* floral meristem identity gene SQUAMOSA", 1996, vol. 250, pp. 7–16.

Thiel, Karl A., "Understanding Your Inner Transistor Radio: The Large–Scale Study of Gene Regulation", http://www-.doubletwist.com/news/co. . . /article,jhtml?section=weekly01name=weekly011, May 26, 2000.

Van Brunt, Jennifer (Editor), "Systems Biology in the Post-Genomics Era", http://www.recap.com/signal . . . /0A9F0F7DD2D01BBE88256874004 C143C?, Jan. 28, 2000.

Takahashi, Nobuaki et al., "High–density cDNA filter analysis of the expression profiles of the genes preferentially expressed in human brain", *Gene*, Jun. 9, 1995, vol. 164, pp. 219–227.

Zhao, Nanding et al., "High–density cDNA filter analysis: a novel approach for large–scale, quantitative analysis of gene expression", *Gene*, Jan. 2, 1995, vol. 156, pp. 207–213.

Pisetsky, David S. et al., "Binding Specificity of a Monoclonal Anti–DNA Antibody", *Molecular Immunology*, Sep. 16, 1981, vol. 19, No. 5, pp. 645–650.

Broude, Natalia E. et al., "Enhanced DNA sequencing by hybridization", *Proc. Natl. Acad. Sci.*, Apr. 1994, vol. 91, pp. 3072–3076.

Kallioniemi, Anne et al., "Comparitive Genomic Hybridization for Molecular Cytogenic Analysis of Solid Tumors", *Science*, Oct. 30, 1992, vol. 258, pp. 818–821.

Velculescu, Victor E. et al., "Serial Analysis of Gene Expression", *Science*, Oct. 20, 1995, vol. 270, pp. 484–487.

Nallur, G.N. et al., "Multiplex Selection Technique (MuST): An Approach to clone trascription factor binding sites", *Proc. Natl. Acad. Sci.* , Feb. 1996, vol. 6, No. 93, pp. 1184–1189.

Meier–Ewert, Sebastian et al., "An automated approach to generating expressed sequence catalogues", *Nature*, Jan. 28, 1993, vol. 361, pp. 375–376.

Barringer, Kevin J. et al., "Blunt–end and single–strand ligations by *Escherichia coli* ligase: influence on an in vitro amplification scheme", *Gene*, Dec. 6, 1989, vol. 89, pp. 117–122.

(Continued)

Primary Examiner—T. D. Wessendorf

(57) ABSTRACT

Methods, arrays and kits are provided for rapidly and efficiently identifying and quantifying multiple different activated transcription factors in a biological sample at the same time. In one aspect, a method is provided for isolating DNA probes which bind to activated transcription factors, including the step of mixing a library of double stranded DNA probes with a sample containing activated transcription factors. The transcription factor probes that have bound to the activated transcription factors are isolated from the mixture via an agarose gel separation. The bound probes can be identified, for example, by using an array of hybridization probes.

15 Claims, 27 Drawing Sheets

OTHER PUBLICATIONS

Bussow, Konrad et al., "A method for global protein expression and antibody screening on high–density filters of an arrayed cDNA library", *Nucleic Acids Research*, Sep. 10, 1998, vol. 26, No. 21, pp. 5007–5008.

Vaughan, Tristan J. et al., "Human Antibodies with Sub–nanomolar Affinities Isolated from a Large Non–immunized Phage Display Library", *Nature Biotechnology*, Mar. 1996, vol. 14, pp. 309–314.

Greenberg, Michale E. et al., "Stimulation of 3T3 cells induces transcription of the c–fos proto–oncogene", *Nature*, Oct. 4, 1984, vol. 311, pp. 433–438.

Ward, E. Sally et al., "Binding activities of a repertoire of single immunoglobulin variable domains secreted from *Escherichia coli*", *Nature*, Oct. 12, 1989, vol. 341, pp. 544–546.

Prooijen–Knegt, A. C. Van et al., "In Situ Hybridization of DNA Sequences in Human Metaphase Chromosomes Visualized by an Indirect Fluorescent Immunocytochemical Procedure", *Experimental Cell Research*, Mar. 10, 1982, vol. 141, pp. 397–407.

Coutlee, Francois et al., "Nonisotopic Detection of RNA in an Enzyme Immunoassay Using a Monoclonal Antibody against DNA–RNA Hybrids", *Analytical Biochemistry*, Feb. 13, 1989, vol. 181, pp. 153–162.

Lee, Youn–Ho et al., "Reusable cDNA Libraries Coupled to Magnetic Beads", *Analytical Biochemistry*, 1992, vol. 206, pp. 206–210.

Lennon, Gregory G. et al., "Hybridization analyses of arrayed cDNA libraries", *Perspectives*, Oct. 1991, vol. 7, No. 10, pp. 314–317.

Boguslawski, Sophie J. et al., "Characterization of monoclonal antibody to DNA RNA and its application to immunodetection of hybrids", *Journal of Immunological Methods*, Dec. 17, 1985, vol. 89, pp. 123–130.

Eberwine, James et al., "Analysis of gene expression in single live neurons", *Proc. Natl. Acad. Sci.*, Apr. 1992, vol. 89, pp. 3010–3014.

Guatelli, John C. et al., "Isothermal, in vitro amplification of nucleic acids by a multienzyme reaction modeled after retroviral replication", *Proc. Natl. Acad. Sci.*, Mar. 1990, vol. 87, pp. 1874–1878.

Marshall, Christopher J., "Tumor Suppressor Genes", *Cell*, Jan. 25, 1991, vol. 64, pp. 313–326.

Wu, Dan Y. et al., "The Ligation Amplification Reaction (LAR)—Amplification of Specific DNA Sequences Using Sequential Rounds of Template–Dependent Ligation", *Genomics*, Dec. 28, 1988, vol. 4, pp. 560–569.

Palazzolo, Michael J. et al., "Phage lambda cDNA cloning vectors for subtractive hybridization, fusion–protein synthesis and Cre–loxP automatic plasmid subcloning", *Gene*, Oct. 5, 1989, vol. 88, pp. 25–36.

Nguyen, Catherine et al., "Differential Gene Expression in the Murine Thymus Assayed by Quantitative Hybridization of Arrayed cDNA Clones", *Genomics*, Jun. 23, 1995, vol. 29, pp. 207–216.

Fornace, Albert J. et al., "DNA damage–inducible transcripts in mammalian cells", *Proc. Natl. Acad. Sci.*, Dec. 1988, vol. 85, pp. 8800–8804.

Schena, Mark et al., "Parallel human genome analysis: Microarray–based expression monitoring of 1000 genes", *Proc. Natl. Acad. Sci.*, Oct. 1996, vol. 93, pp. 10614–10619.

Chee, Mark et al., "Accessing Genetic Information with High–Density DNA Arrays", *Science*, Oct. 25, 1996, vol. 274, pp. 610–614.

Campbell, David A. et al., "Phosphonate Ester Synthesis Using a Modified Mitsunobu Condensation", *J. Org. Chem.*, 1994, vol. 59, No. 3, pp. 658–660.

Viscidi, Raphael P. et al., "Monoclonal Antibody Solution Hybridization Assay for Detection of Human Immunodeficiency Virus Nucleid Acids", *Journal of Microbiology*, Jan. 1989, vol. 27, No. 1, pp. 120–125.

Van Gelder, Russell N. et al., "Amplified RNA synthesized from limited quantities of heterogeneous cDNA", *Proc. Natl. Acad. Sci.*, Mar. 1990, vol. 87, pp. 1663–1667.

DeWitt, Sheila Hobbs et al., "Diversomers: An approach to nonpeptide, nonoligomeric chemical diversity", *Proc. Natl. Acad. Sci.*, Aug. 1993, vol. 90, pp. 6909–6913.

Sasmor, Henri et al., "Symmetric lac operator derivatives: effects of half–operator sequence and spacing on repressor affinity", *Gene*, Jan. 7, 1990, vol. 89, pp. 1–6.

Oelgeschlager, Thomas et al., "Probing the function of individual amino acid residues in the DNA binding site of the EcoRI restriction endonuclease by analysing the toxicity of genetically engineered mutants", *Gene*, Nov. 10, 1989, vol. 89, pp. 19–27.

Dignam, John David et al., "Accurate transcription initiation by RNA polymerase II in a soluble extract from isolated mammalian nuclei", *Nucliec Acids Research*, Jan. 18, 1983, vol. 11, pp. 1475–1489.

Southern, E. M. et al., "Arrays of complementary oligonucleotides for analysing the hybridisation behavior of nucleic acids" *Nucleic Acids Research*, Mar. 9, 1994, vol. 22, No. 8, pp. 1368–1373.

Huse, William D. et al., "Generation of a Large Combinatorial Library of the Immunoglobulin Repertoire in Phage Lambda", *Science*, Dec. 8, 1989, vol. 246, pp. 1275–1281.

Theillet, Charles, "Full speed ahead for tumor screening", *Nature Medicine*, Jul. 1998, vol. 4, No. 7, pp. 767–768.

Kononen, Juha et al., "Tissue microarrays for high–throughput molecular profiling of tumor specimens", *Nature Medicine*, Jul. 1998, vol. 4, No. 7, pp. 844–847.

Liang, Rui et al., "Parallel Synthesis and Screening of a Solid Phase Carbohydrate Library", *Science*, Nov. 29, 1996, vol. 274, pp. 1520–1522.

Uetz, Peter et al., "A comprehensive analysis of protein—protein interactions in *Saccharomyces cerevisiae*", *Nature*, Feb. 10, 2000, vol. 403, pp. 623–627.

Zehetner, Gunther, "The Reference Library System—sharing biological material and experimental data", *Nature*, Feb. 3, 1994, vol. 367, pp. 489–491.

Landegren, Ulf et al., "A Ligase–Mediated Gene Detection Technique", *Science*, Aug. 1988, vol. 241, pp. 1077–1080.

Kuijpers, W.H.A. et al., "Synthesis of well–defined phosphate–methylated DNA fragments: the application of potassium carbonate in menthanol as deprotecting reagent", *Nucleic Acids Research*, Jun. 13, 1990, vol. 18, No. 17, pp. 5197–5205.

Houghten, Richard A. et al., "Generation and use of synthetic peptide combinatorial libraries for basic research and drug discovery", *Nature*, Nov. 7, 1991, vol. 354, pp. 84–86.

Kohler, G. et al., "Continuous cultures of fused cells secreting antibody of predefined specificity", *Nature*, Aug. 7, 1975, vol. 256, pp. 495–497.

Rudkin, George et al., "High resolution detection of DNA–RNA hybrids in situ by indirect immunofluorescence", *Nature*, Feb. 3, 1977, vol. 265, pp. 472–473.

Kwoh, D. Y. et al., "Transcription–based amplification system and detection of amplified human immunodeficiency virus type 1 with a bead–based sandwich hybridization format", *Proc. Natl. Acad. Sci.*, Feb. 1989, vol. 86, pp. 1173–1177.

Meier–Ewer, Sebastian et al., "Comparitive gene expression profiling by oligonucleotide fingerprinting", *Nucleic Acids Research*, Mar. 8, 1998, vol. 26, No. 9, pp. 2216–2223.

Gress, Thomas et al., "Hybridization fingerprinting of high-density cDNA–library arrays with cDNA pools derived from whole tissues", *Mammalian Genome*, Jul. 2, 1992, vol. 3, pp. 609–619.

Lockhard, David J. et al., "Expression monitoring by hybridization to high–density oligonucleotide arrays", *Nature Biotechnology*, Dec. 1997, vol. 14, pp. 1675–1680.

Schena, Mark et al., "Quantitative Monitoring of Gene Expression Patterns with a Complimentary DNA Microarray", *Science*, Oct. 20, 1995, vol. 270, pp. 467–470.

Phimster, Bette, "Going global", *Nature Genetics*, Jan. 1999, vol. 21, No. 1, pp. 1–50.

Englert, Chad R. et al., "Layered Expression Scanning: Rapid Molecular Profiling of Tumor Samples", *Cancer Research*, Mar. 15, 2000, vol. 60, pp. 1526–1530.

Taylor, Laura C. et al., "Application of a High–Density Optical Micowell Arrays in a Live–Cell Biosensing System", *Analytical Biochemistry*, May 14, 1999, vol. 26, pp. 132–142.

Arenkov, Pavel et al., "Protein Microchips: Use for Immunoassay and Enzymatic Reactions", *Analytical Biochemistry*, Jun. 7, 1999, vol. 278, pp. 123–131.

* cited by examiner

FIGURE 2
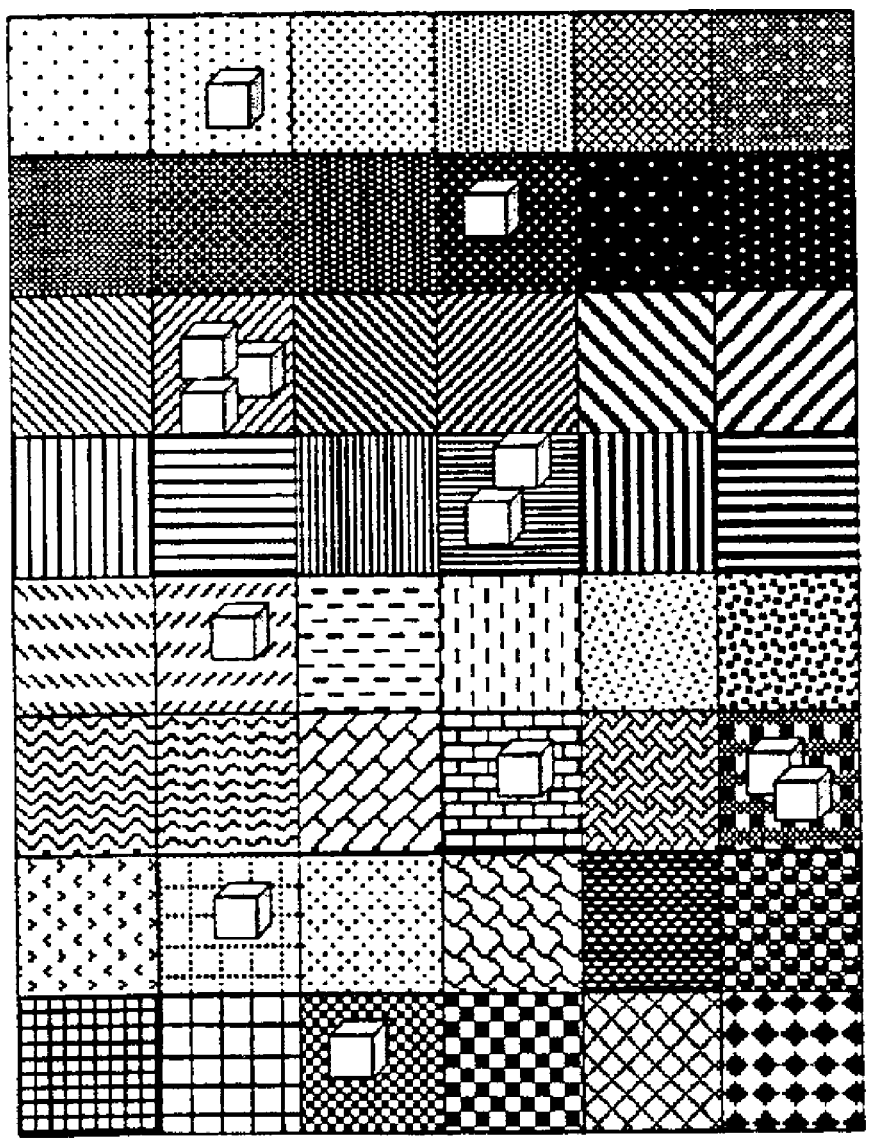
 probe with detectable marker

FIGURE 3
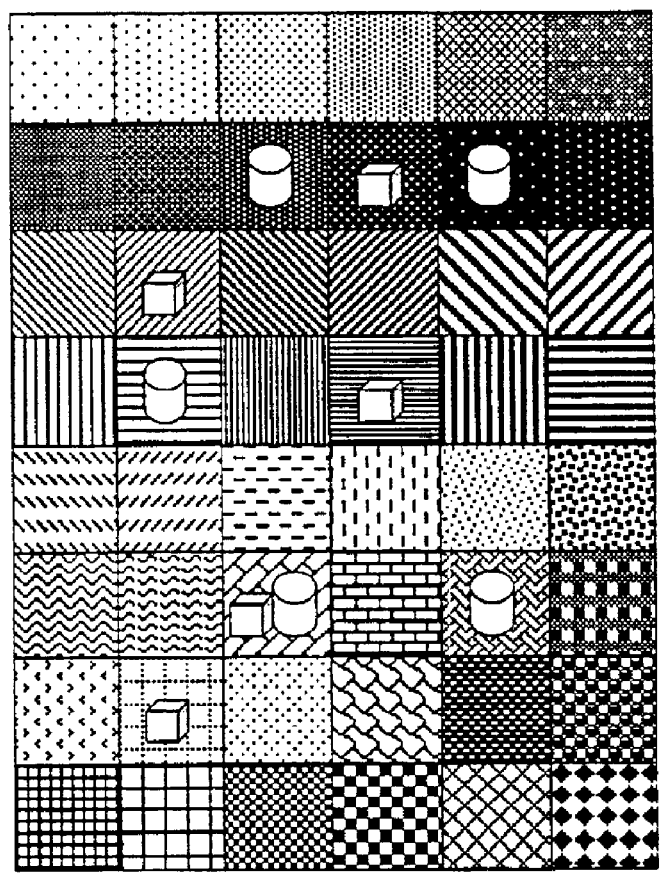
LEGEND
  probe with green dye
  probe with red dye
  region appearing yellow having both probes with green and red dyes

FIGURE 6

EXAMPLES OF TRANSCRIPTION FACTOR PROBES AND ARRAY HYBRIDIZATION PROBES

| TF | Name | Transcription Factor Probes | | Name | Hybridization Probes |
|---|---|---|---|---|---|
| AP1 | PP01 | CGCTTGATGACTCAGCCGGAA [SEQ ID NO: 1] | 5'-biotin | | |
| AP1 | PP02 | TTCCGGCTGAGTCATCAAGCG [SEQ ID NO: 2] | | MP02 | TTCCGGCTGAGTCATCAAGCGTTCCGGCTGAGTCATCAAGCGTTCCGGCTGAGTCATCAAGCG [SEQ ID NO: 109] |
| AP-2 | PP03 | GATCGAACTGACCGCCCGGCCCGT [SEQ ID NO: 3] | 5'-biotin | | |
| AP-2 | PP04 | ACGGGCCGCGGGGCGGTCAGTTCGATC [SEQ ID NO: 4] | | MP04 | ACGGGCCGCGGGGCGGTCAGTTCGATCACGGGCCGCGGGGCGGTCAGTTCGATCACGGGCCGCGGGGCGGTCAGTTCGATC [SEQ ID NO: 110] |
| ARE | PP05 | GTCTGGTACAGGGTGTTCTTTTT [SEQ ID NO: 5] | 5'-biotin | | |
| ARE | PP06 | AAAAGAACACCCTGTACCAGAC [SEQ ID NO: 6] | | MP06-1 | AAAAGAACACCCTGTACCAGACAAAAGAACACCCTGTACCAGACAAAAGAACACCCTGTACCAGAC [SEQ ID NO: 111] |
| Brn-3 | PP07 | CACAGCTCATTAACGCGC [SEQ ID NO: 7] | 5'-biotin | | |
| Brn-3 | PP08 | GCGCGTTAATGAGCTGTG [SEQ ID NO: 8] | | MP08 | GCGCGTTAATGAGCTGTGGCGCGTTAATGAGCTGTGGCGCGTTAATGAGCTGTG [SEQ ID NO: 112] |
| C/EBP | PP09 | TGCAGATTGCGCAATCTGCA [SEQ ID NO: 9] | 5'-biotin | | |
| C/EBP | PP10 | TGCAGATTGCGCAATCTGCA [SEQ ID NO: 10] | | MP10 | TGCAGATTGCGCAATCTGCATGCAGATTGCGCAATCTGCATGCAGATTGCGCAATCTGCA [SEQ ID NO: 113] |
| CBF | PP11 | AGACCGTACGTGATTGGTTAATCTCTT [SEQ ID NO: 11] | 5'-biotin | | |
| CBF | PP12 | AAGAGATTAACCAATCACGTACGGTCT [SEQ ID NO: 12] | | MP12 | AAGAGATTAACCAATCACGTACGGTCTAAGAGATTAACCAATCACGTACGGTCTAAGAGATTAACCAATCACGTACGGTCT [SEQ ID NO: 114] |

FIGURE 6 - CONTINUED

| | | | | | |
|---|---|---|---|---|---|
| CDP | PP13 | ACCCAATGATTATTAGCCAATTTCTGA [SEQ ID NO: 13] | | | |
| CDP | PP14 | TCAGAAATTGGCTAATAATCATTGGGT [SEQ ID NO: 14] | 5'-biotin | MP14 | TCAGAAATTGGCTAATAATCATTGGGTTCAGAA ATTGGCTAATAATCATTGGGTTCAGAAATTGGC TAATAATCATTGGGT [SEQ ID NO: 115] |
| c-Myb | PP15 | TACAGGCATAACGGTTCCGTAGTGA [SEQ ID NO: 15] | | | |
| c-Myb | PP16 | TCACTACGGAACCGTTATGCCTGTA [SEQ ID NO: 16] | 5'-biotin | MP16 | TCACTACGGAACCGTTATGCCTGTATCACTACG GAACCGTTATGCCTGTATCACTACGGAACCGTT ATGCCTGTA [SEQ ID NO: 116] |
| CREB | PP17 | AGAGATTGCCTGACGTCAGAGAGCTAG [SEQ ID NO: 17] | | | |
| CREB | PP18 | CTAGCTCTCTGACGTCAGGCAATCTCT [SEQ ID NO: 18] | 5'-biotin | MP18 | CTAGCTCTCTGACGTCAGGCAATCTCTCTAGCT CTCTGACGTCAGGCAATCTCTCTAGCTCTCTGA CGTCAGGCAATCTCT [SEQ ID NO: 117] |
| E2F-1 | PP19 | ATTTAAGTTTCGCGCCCTTTCTCAA [SEQ ID NO: 19] | | | |
| E2F-1 | PP20 | TTGAGAAAGGGCGCGAAACTTAAAT [SEQ ID NO: 20] | 5'-biotin | MP20 | TTGAGAAAGGGCGCGAAACTTAAATTTGAGAAA GGGCGCGAAACTTAAATTTGAGAAAGGGCGCGA AACTTAAAT [SEQ ID NO: 118] |
| EGR | PP21 | GGATCCAGCGGGGGGAGCGGGGCCA [SEQ ID NO: 21] | | | |
| EGR | PP22 | TGGCCCCGCTCGCCCCCGCTGGATCC [SEQ ID NO: 22] | 5'-biotin | MP22 | TGGCCCCCGCTCGCCCCCGCTGGATCCTGGCCC CGCTCGCCCCCGCTGGATCCTGGCCCCCGCTC GCCCCCGCTGATCC [SEQ ID NO: 119] |
| ERE | PP23 | GTCCAAAGTCAGGTCACAGTGACCTGATCAAAGTT [SEQ ID NO: 23] | | | |
| ERE | PP24 | AACTTTGATCAGGTCACTGTGACCTGACTTTGGAC [SEQ ID NO: 24] | 5'-biotin | MP24 | AACTTTGATCAGGTCACTGTGACCTGACTTTGG ACAACTTTGATCAGGTCACTGTGACCTGACTTT GGAC [SEQ ID NO: 120] |
| Ets | PP25 | GGAGGAGGGCTGCTTGAGGAAGTATAAGAAT [SEQ ID NO: 25] | | | |
| Ets | PP26 | ATTCTTATACTTCCTCAAGCAGCCCTCCTCC [SEQ ID NO: 26] | 5'-biotin | MP26 | ATTCTTATACTTCCTCAAGCAGCCCTCCTCCAT TCTTATACTTCCTCAAGCAGCCCTCCTCCATTC |

FIGURE 6 - CONTINUED

| | | | | | |
|---|---|---|---|---|---|
| Ets-1/PEA3 | PP27 | GATCTCGAGCAGGAAGTTCGA [SEQ ID NO: 27] | | | TTATACTTCCTCAAGCAGCCCTCCTCC [SEQ ID NO: 121] |
| Ets-1/PEA3 | PP28 | TCGAACTTCCTGCTCGAGATC [SEQ ID NO: 28] | 5'-biotin | MP28 | TCGAACTTCCTGCTCGAGATCTCGAACTTCCTG CTCGAGATCTCGAACTTCCTGCTCGAGATC [SEQ ID NO: 122] |
| FAST-1 | PP29 | CGGATTGTGTATTGGCTGTAC [SEQ ID NO: 29] | 5'-biotin | | |
| FAST-1 | PP30 | GTACAGCCAATACACAATCCG [SEQ ID NO: 30] | | MP30 | GTACAGCCAATACACAATCCGGTACAGCCAATA CACATCCGGTACAGCCAATACACAATCCG [SEQ ID NO: 123] |
| GAS/ISRE | PP31 | CGAAGTACTTTCAGTTTCATATTACTCTACAA [SEQ ID NO: 31] | 5'-biotin | | |
| GAS/ISRE | PP32 | TTGTAGAGTAATATGAAACTGAAAGTACTTCG [SEQ ID NO: 32] | | MP32 | TTGTAGAGTAATATGAAACTGAAAGTACTTCGT TGTAGAGTAATATGAAACTGAAAGTACTTCGTT GTAGAGTAATATGAAACTGAAAGTACTTCG [SEQ ID NO: 124] |
| GATA | PP33 | CACTTGATAACAGAAAGTGATAACTCT [SEQ ID NO: 33] | 5'-biotin | | |
| GATA | PP34 | AGAGTTATCACTTTCTGTTATCAAGTG [SEQ ID NO: 34] | | MP34 | AGAGTTATCACTTTCTGTTATCAAGTGAGAGTT ATCACTTTCTGTTATCAAGTGAGAGTTATCACT TTCTGTTATCAAGTG [SEQ ID NO: 125] |
| GRE | PP35 | GACCCTAGAGGATCTGTACAGGATGTTCTAGATCCAA TTCG [SEQ ID NO: 35] | 5'-biotin | | |
| GRE | PP36 | CGAATTGGATCTAGAACATCCTGTACAGATCCTCTAG GGTC [SEQ ID NO: 36] | | MP36 | CGAATTGGATCTAGAACATCCTGTACAGATCCT CTAGGGTCGAATTGGATCTAGAACATCCTGTA CAGATCCCTAGGGTC [SEQ ID NO: 126] |
| HNF-4 | PP37 | CTCAGCTTGTACTTTGGTACAACTA [SEQ ID NO: 37] | 5'-biotin | | |
| HNF-4 | PP38 | TAGTTGTACCAAAGTACAAGCTGAG [SEQ ID NO: 38] | | MP38 | TAGTTGTACCAAAGTACAAGCTGAGTAGTTGTA CCAAAGTACAAGCTGAGTAGTTGTACCAAAGTA CAAGCTGAG [SEQ ID NO: 127] |
| IRF-1 | PP39 | GGAAGCGAAAATGAAATTGACT [SEQ ID NO: 39] | 5'-biotin | | |
| IRF-1 | PP40 | AGTCAATTTCATTTTCGCTTCC | | MP40 | AGTCAATTTCATTTTCGCTTCCAGTCAATTCA |

FIGURE 6 - CONTINUED

| | | | | | |
|---|---|---|---|---|---|
| MEF-1 | PP41 | GATCCCCCAACACCTGCTGA [SEQ ID NO: 40] | | | TTTTCGCTTCCAGTCAATTTCATTTTCGCTTCC [SEQ ID NO: 128] |
| MEF-1 | PP42 | TCAGGCAGCAGGTGTTGGGGGATC [SEQ ID NO: 41] [SEQ ID NO: 42] | 5'-biotin | MP42 | TCAGGCAGCAGGTGTTGGGGGATCTCAGGCAG CAGGTGTTGGGGGATCTCAGGCAGCAGGTGTT GGGGGATC [SEQ ID NO: 129] |
| MEF-2 | PP43 | GATCGCTCTAAAAATAACCCTGTCG [SEQ ID NO: 43] | 5'-biotin | | |
| MEF-2 | PP44 | CGACAGGGTTATTTTTAGAGCGATC [SEQ ID NO: 44] | | MP44 | CGACAGGGTTATTTTTAGACCGATCCGACAGGG TTATTTTTAGACCGATCCGACAGGGTTATTTTT AGACCGATC [SEQ ID NO: 130] |
| Myc-Max | PP45 | GGAAGCAGACCACGTGTCTGCTTCC [SEQ ID NO: 45] | 5'-biotin | | |
| Myc-Max | PP46 | GGAAGCAGACCACGTGGTCTGCTTCC [SEQ ID NO: 46] | | MP46 | GGAAGCAGACCACGTGGTCTGCTTCCGGAAGCA GACCACGTGGTCTGCTTCCGGAAGCAGACCACG TGGTCTGCTTCC [SEQ ID NO: 131] |
| NF-1 | PP47 | TTTTGGATTGAAGCCAATATGATAA [SEQ ID NO: 47] | 5'-biotin | | |
| NF-1 | PP48 | TTATCATATTGGCTTCAATCCAAAA [SEQ ID NO: 48] | | MP48 | TTATCATATTGGCTTCAATCCAAAATATCATA TTGGCTTCAATCCAAAATATCATATTGGCTTC AATCCAAAA [SEQ ID NO: 132] |
| NFATc | PP49 | ACGCCCAAAGAGGAAATTTGTTTCATACA [SEQ ID NO: 49] | 5'-biotin | | |
| NFATc | PP50 | TGTATGAAACAAATTTCCTCTTTGGGCGT [SEQ ID NO: 50] | | MP50 | TGTATGAAACAAATTTCCTCTTTGGGCGTTGT ATGAAACAAATTTCCTCTTTGGGCGTTGTATG AAACAAATTTCCTCTTTGGGCGT [SEQ ID NO: 133] |
| NF-E1 (YY1) | PP51 | CGCTCCGGCCATCTTGGCGGCTGGT [SEQ ID NO: 51] | 5'-biotin | | |
| NF-E1 (YY1) | PP52 | ACCAGCCGCCAAGATGGCCGGGAGCG [SEQ ID NO: 52] | | MP52 | ACCAGCCGCCAAGATGGCCGGGAGCGACCAGC CGCCAAGATGGCCGGGAGCGACCAGCCGCCAA GATGGCCGGGAGCG [SEQ ID NO: 134] |
| NF-E2 | PP53 | TGGGGAACCTGTGCTGAGTCACTGGAG [SEQ ID NO: 53] | 5'-biotin | | |

FIGURE 6 - CONTINUED

| | | | | |
|---|---|---|---|---|
| NF-E2 | PP54 | CTCCAGTGACTCAGACAGGTTCCCCA [SEQ ID NO: 54] | MP54 | CTCCAGTGACTCAGCAGACAGTTCCCCACTCCAG TGACTCAGCACAGTTCCCCACTCCAGTGACTC AGACACAGGTTCCCCA [SEQ ID NO: 135] |
| NFkB | PP55 | AGTTGAGGGGACTTTCCCAGGC [SEQ ID NO: 55] | | |
| NFkB | PP56 | GCCTGGGAAAGTCCCCTCAACT [SEQ ID NO: 56] | MP56 | GCCTGGGAAAGTCCCCTCAACTGCTGGGAAAG TCCCCTCAACTGCCTGGGAAAGTCCCCTCAACT [SEQ ID NO: 136] |
| Oct-1 | PP57 | TGTCGAATGCAAATCACTAGAA [SEQ ID NO: 57] | | |
| Oct-1 | PP58 | TTCTAGTGATTTCCATTCGACA [SEQ ID NO: 58] | MP58 | TTCTAGTGATTTCCATTCGACATTCTAGTGATT TCCATTCGACATTCTAGTGATTTCCATTCGACA [SEQ ID NO: 137] |
| p53 | PP59 | TACAGAACATGTCTAAGCATGCTGGGG [SEQ ID NO: 59] | | |
| p53 | PP60 | CCCCAGCATGCTTAGACATGTTCTGTA [SEQ ID NO: 60] | MP60 | CCCCAGCATGCTTAGACATGTTCTGTACCCCAG CATGCTTAGACATGTTCTGTACCCCAGCATGCT TAGACATGTTCTGTA [SEQ ID NO: 138] |
| Pax-5 | PP61 | GAATGGGCACTGAGGCGTGACCACCG [SEQ ID NO: 61] | | |
| Pax-5 | PP62 | CGGTGGTCACGCCTCAGTGCCCATTC [SEQ ID NO: 62] | MP62 | CGGTGGTCACGCCTCAGTGCCCCATTCCGGTGG TCACGCCTCAGTGCCCCATTCCGGTGGTCACGC CTCAGTGCCCCATTC [SEQ ID NO: 139] |
| Pbx1 | PP63 | CGAATTGATTGATGCACTAATTGGAG [SEQ ID NO: 63] | | |
| Pbx1 | PP64 | CTCCAATTAGTGCATCAATCAATTCG [SEQ ID NO: 64] | MP64 | CTCCAATTAGTGCATCAATCAATTCGCTCCAAT TAGTGCATCAATCAATTCGCTCCAATTAGTGCA TCAATCAATTCG [SEQ ID NO: 140] |
| Pit 1 | PP65 | TGTCTTCCTGAATATGAATAAGAAATAA [SEQ ID NO: 65] | | |
| Pit 1 | PP66 | TTATTTCTTATTCATATTCAGGAAGACA [SEQ ID NO: 66] | MP66 | TTATTTCTTATTCATATTCAGGAAGACATTATT TCTTATTCATATTCAGGAAGACATTATTTCTTA TTCATATTCAGGAAGACA [SEQ ID NO: 141] |
| PPAR | PP67 | CAAAACTAGGTCAAAGGTCA [SEQ ID NO: 67] | | |

FIGURE 6 - CONTINUED

| | | | | | |
|---|---|---|---|---|---|
| PPAR | PP68 | TGACCTTTGACCTAGTTTTG [SEQ ID NO: 68] | | MP68 | TGACCTTTGACCTAGTTTTGTGACCTTTGACCT AGTTTTGTGACCTTTGACCTAGTTTTG [SEQ ID NO: 142] |
| PRE | PP69 | GATCCTGTACAGGATGTTCTAGCTACA [SEQ ID NO: 69] | 5'-biotin | | |
| PRE | PP70 | TGTAGCTAGAACATCCTGTACAGGATC [SEQ ID NO: 70] | | MP70 | TGTAGCTAGAACATCCTGTACAGGATCTGTAGC TAGAACATCCTGTACAGGATCTGTAGCTAGAAC ATCCTGTACAGGATC [SEQ ID NO: 143] |
| RAR(DR-5) | PP71 | TCGAGGGTAGGGTTCACCGAAAGTTCACTCG [SEQ ID NO: 71] | 5'-biotin | | |
| RAR(DR-5) | PP72 | CGAGTGAACTTTCGGTGAACCCTACCCTCGA [SEQ ID NO: 72] | | MP72 | CGAGTGAACTTTCGGTGAACCCTACCCTCGACG AGTGAACTTTCGGTGAACCCTACCCTCGACGAG TGAACTTTCGGTGAACCCTACCCTCGA [SEQ ID NO: 144] |
| RXR(DR-1) | PP73 | AGCTTCAGGTCAGAGGTCAGAGAGCT [SEQ ID NO: 73] | 5'-biotin | | |
| RXR(DR-1) | PP74 | AGCTCTCTGACCTCTGACCTGAAGCT [SEQ ID NO: 74] | | MP74 | AGCTCTCTGACCTCTGACCTGAAGCTAGCTCTC TGACCTCTGACCTCTGAAGCTAGCTCTCTGACCTC TGACCTGAAGCT [SEQ ID NO: 145] |
| SIE | PP75 | GTGCATTTCCCGTAAATCTTGTCTACA [SEQ ID NO: 75] | 5'-biotin | | |
| SIE | PP76 | TGTAGACAAGATTTACGGGAAATGCAC [SEQ ID NO: 76] | | MP76 | TGTAGACAAGATTTACGGGAAATGCACTGTAGA CAAGATTTACGGGAAATGCACTGTAGACAAGAT TTACGGGAAATGCAC [SEQ ID NO: 146] |
| Smad SBE | PP77 | AGTATGTCTAGACTGA [SEQ ID NO: 70] | 5'-biotin | | |
| Smad SBE | PP78 | TCAGTCTAGACATACT [SEQ ID NO: 78] | | MP78 | TCAGTCTAGACATACTTCAGTCTAGACATACTT CAGTCTAGACATACTTCAGTCTAGACATACT [SEQ ID NO: 147] |
| Smad3/4 | PP79 | TCGAGAGCCAGACAAAAAGCCAGACATTTAGCCAGAC AC [SEQ ID NO: 79] | 5'-biotin | | |
| Smad3/4 | PP80 | GTGTCTGGCTAAATGTCTGGCTTTTTGTCTGGCTCTC GA [SEQ ID NO: 80] | | MP80 | GTGTCTGGCTAAATGTCTGGCTTTTTGTCTGGC TCTCGAGTGTCTGGCTAAATGTCTGGCTTTTTG TCTGGCTCTCGAGTGTCTGGCTAAATGTCTGGC TTTTGTCTGGCTCTCGA [SEQ ID NO: 148] |

FIGURE 6 - CONTINUED

| | | | | 5'-biotin | |
|---|---|---|---|---|---|
| Sp1 | PP81 | ATTCGATCGGGGCGGGGCGAG<br>[SEQ ID NO: 81] | | | |
| Sp1 | PP82 | CTCGCCCCGCCCCGATCGAAT<br>[SEQ ID NO: 82] | | MP82 | CTCGCCCCGCCCCGATCGAATCTCGCCCCGCCC<br>CGATCGAATCTCGCCCCGCCCCGATCGAAT<br>[SEQ ID NO: 149] |
| SRE | PP83 | GGATGTCCATATTAGGACATCT<br>[SEQ ID NO: 83] | | 5'-biotin | |
| SRE | PP84 | AGATGTCCTAATATGGACATCC<br>[SEQ ID NO: 84] | | MP84 | AGATGTCCTAATATGGACATCCAGATGTCCTAA<br>TATGGACATCCAGATGTCCTAATATGGACATCC<br>[SEQ ID NO: 150] |
| Stat1 p84/p91 | PP85 | CATGTTATGCATATTCCTGTAAGTG<br>[SEQ ID NO: 85] | | 5'-biotin | |
| Stat1 p84/p91 | PP86 | CACTTACAGGAATATGCATAACATG<br>[SEQ ID NO: 86] | | MP86 | CACTTACAGGAATATGCATAACATGCACTTACA<br>GGAATATGCATAACATGCACTTACAGGAATATG<br>CATAACATG<br>[SEQ ID NO: 151] |
| Stat3 | PP87 | GATCCTTCTGGGAATTCCTAGATC<br>[SEQ ID NO: 87] | | 5'-biotin | |
| Stat3 | PP88 | GATCTAGGAATTCCCAGAAGGATC<br>[SEQ ID NO: 88] | | MP88 | GATCTAGGAATTCCCAGAAGGATCGATCTAGGA<br>ATTCCCAGAAGGATCGATCTAGGAATTCCCAGA<br>AGGATC<br>[SEQ ID NO: 152] |
| Stat4 | PP89 | CTAGAGCCTGATTTCCCGAAATGATGAGCTAG<br>[SEQ ID NO: 89] | | 5'-biotin | |
| Stat4 | PP90 | CTAGCTCATCATTTCGGGAAATCAGGCTCTAG<br>[SEQ ID NO: 90] | | MP90 | CTAGCTCATCATTTCGGGAAATCAGGCTCTAG<br>CTAGCTCATCATTTCGGGAAATCAGGCTCTAG<br>CTAGCTCATCATTTCGGGAAATCAGGCTCTAG<br>[SEQ ID NO: 153] |
| stat5 | PP91 | AGATTTCTAGAATTCAATCC<br>[SEQ ID NO: 91] | | 5'-biotin | |
| stat5 | PP92 | GGATTGAATTCCTAGAAATCT<br>[SEQ ID NO: 92] | | MP92 | GGATTGAATTCCTAGAAATCTGATTGAATTCC<br>TAGAAATCTGGATTGAATTCCTAGAAATCT<br>[SEQ ID NO: 154] |
| Stat5/Stat6 | PP93 | GTATTCCCAGAAAAGGAAC<br>[SEQ ID NO: 93] | | 5'-biotin | |
| Stat5/Stat6 | PP94 | GTTCCTTTTCTGGGAAATAC<br>[SEQ ID NO: 94] | | MP94 | GTTCCTTTTCTGGGAAATACGTTCCTTTTCTGG<br>GAAATACGTTCCTTTTCTGGGAAATAC<br>[SEQ ID NO: 155] |

FIGURE 6 - CONTINUED

| | | | | 5'-biotin | | |
|---|---|---|---|---|---|---|
| TFIID | PP95 | GCAGAGCATATAAAATGAGGTAGGA [SEQ ID NO: 95] | | | | |
| TFIID | PP96 | TCCTACCTCATTTTATATGTCTCTGC [SEQ ID NO: 96] | | | MP96 | TCCTACCTCATTTTATATGTCTCTGCTCCTACCT CATTTTATATGTCTCTGCTCCTACCTCATTTAT ATGTCTGC [SEQ ID NO: 156] |
| TR | PP97 | GATCGTAAGATTCAGGTCATGACCTGAGGAGA [SEQ ID NO: 97] | | 5'-biotin | | |
| TR | PP98 | TCTCCTCAGGTCATGACCTGAATCTTACGATC [SEQ ID NO: 98] | | | MP98 | TCTCCTCAGGTCATGACCTGAATCTTACGATCT CTCCTCAGGTCATGACCTGAATCTTACGATCTC TCCTCAGGTCATGACCTGAATCTTACGATC [SEQ ID NO: 157] |
| TR(DR-4) | PP99 | AGCTTCAGGTCACAGGAGTCAGAGAGCT [SEQ ID NO: 99] | | 5'-biotin | | |
| TR(DR-4) | PP100 | AGCTCTCTGACCTCTGTGACCTGAAGCT [SEQ ID NO: 100] | | | MP100 | AGCTCTCTGACCTCTGTGACCTGAAGCTAGCT CTCTGACCTCCTGTGACCTGAAGCTAGCTCTCT GACCTCCTGACCTGAAGCT [SEQ ID NO: 158] |
| USF-1 | PP101 | CACCCGGTCACGTGGCCTACACC [SEQ ID NO: 101] | | 5'-biotin | | |
| USF-1 | PP102 | GGTGTAGGCCACGTGACCGGGTG [SEQ ID NO: 102] | | | MP102 | GGTGTAGGCCACGTGACCGGGTGGTGTAGGCC ACGTGACCGGGTGGGTGTAGGCCACGTGACCGG GTG [SEQ ID NO: 159] |
| VDR(DR-3) | PP103 | AGCTTCAGGTCAAGGAGTCAGAGAGCT [SEQ ID NO: 103] | | 5'-biotin | | |
| VDR(DR-3) | PP104 | AGCTCTCTGACCTCCTTGACCTGAAGCT [SEQ ID NO: 104] | | | MP104 | AGCTCTCTGACCTCCTTGACCTGAAGCTAGCTC TCTGACCTCCTTGACCTGAAGCTAGCTCTCTGA CCTCCTTGACCTGAAGCT [SEQ ID NO: 160] |
| HSE | PP105 | CTGGAATTTTCTAGA [SEQ ID NO: 105] | | 5'-biotin | | |
| HSE | PP106 | TCTAGAAAATTCCAG [SEQ ID NO: 106] | | | MP106 | TCTAGAAAATTCCAGTCTAGAAAATTCCAGTCT AGAAAATTCCAGTCTAGAAAATTCCAG [SEQ ID NO: 161] |
| MRE | PP107 | CTCTGCGCCGGCCC [SEQ ID NO: 107] | | 5'-biotin | | |
| MRE | PP108 | GGGCCGGCGCAGAG [SEQ ID NO: 108] | | | MP108 | GGGCCGGCGCAGAGGGGCCGGCGCAGAGGGG CCGGCGCAGAGGGGCCGGCGCAGAG [SEQ ID NO: 162] |

Figure 7

Array Format of Transcription Factor Binding Elements

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A | AP1 | AP1 | AP-2 | AP-2 | ARE | ARE | Brn-3 | Brn-3 | C/EBP | C/EBP | CBF | CBF | CDP | CDP | c-Myb | c-Myb | |
| B | AP1 | AP1 | AP-2 | AP-2 | ARE | ARE | Brn-3 | Brn-3 | C/EBP | C/EBP | CBF | CBF | CDP | CDP | c-Myb | c-Myb | |
| C | CREB | CREB | E2F-2 | E2F-2 | EGR | EGR | ERE | ERE | Ets | Ets | Ets-1/PEA3 | Ets-1/PEA3 | FAST-1 | FAST-1 | GAS/ISRE | GAS/ISRE | |
| D | CREB | CREB | E2F-2 | E2F-2 | EGR | EGR | ERE | ERE | Ets | Ets | Ets-1/PEA3 | Ets-1/PEA3 | FAST-1 | FAST-1 | GAS/ISRE | GAS/ISRE | |
| E | GATA | GATA | GRE | GRE | HNF-4 | HNF-4 | IRF-1 | IRF-1 | MEF-1 | MEF-1 | MEF-2 | MEF-2 | Myc-Max | Myc-Max | NF-1 | NF-1 | |
| F | GATA | GATA | GRE | GRE | HNF-4 | HNF-4 | IRF-1 | IRF-1 | MEF-1 | MEF-1 | MEF-2 | MEF-2 | Myc-Max | Myc-Max | NF-1 | NF-1 | |
| G | NFATc | NFATc | NF-E1(YY1) | NF-E1(YY1) | NF-E2 | NF-E2 | NFkB | NFkB | Oct-1 | Oct-1 | p53 | p53 | Pax-5 | Pax-5 | Pbx1 | Pbx1 | |
| H | NFATc | NFATc | NF-E1(YY1) | NF-E1(YY1) | NF-E2 | NF-E2 | NFkB | NFkB | Oct-1 | Oct-1 | p53 | p53 | Pax-5 | Pax-5 | Pbx1 | Pbx1 | |
| I | Pit1 | Pit1 | PPAR | PPAR | PRE | PRE | RAR(DR-5) | RAR(DR-5) | RXR(DR-1) | RXR(DR-1) | SIE | SIE | Smad SBE | Smad SBE | Smad3/4 | Smad3/4 | |
| J | Pit1 | Pit1 | PPAR | PPAR | PRE | PRE | RAR(DR-5) | RAR(DR-5) | RXR(DR-1) | RXR(DR-1) | SIE | SIE | Smad SBE | Smad SBE | Smad3/4 | Smad3/4 | |
| K | Sp1 | Sp1 | SRE | SRE | Stat1 p84/p91 | Stat1 p84/p91 | Stat3 | Stat3 | Stat4 | Stat4 | Stat5 | Stat5 | Stat6 | Stat6 | TFIID | TFIID | |
| L | Sp1 | Sp1 | SRE | SRE | Stat1 p84/p91 | Stat1 p84/p91 | Stat3 | Stat3 | Stat4 | Stat4 | Stat5 | Stat5 | Stat6 | Stat6 | TFIID | TFIID | |
| M | TR | TR | TR(DR-4) | TR(DR-4) | USF-1 | USF-1 | VDR(DR-3) | VDR(DR-3) | HSE | HSE | MRE | MRE | | | | | |
| N | TR | TR | TR(DR-4) | TR(DR-4) | USF-1 | USF-1 | VDR(DR-3) | VDR(DR-3) | HSE | HSE | MRE | MRE | | | | | |
| O | | | | | | | | | | | | | | | | | |
| P | | | | | | | | | | | | | | | | | |

■ 1:1000 Biotinylated 30APB3-5Br oligonucleotides used for positioning

| Duplicate Samples | 1 | 2 | Normalized concentration |
|---|---|---|---|
| A | AP1 | AP1 | 1:10 dilutions of normalized concentration |
| B | AP1 | AP1 | |

Brn3 c-Myb

Smad3/4

Brn3--Myb+Smad3/4

Without HeLa nuclear extract

With HeLa nuclear extract

HeLa nuclear extract

↑ ↑
NF-EI  Ets

PMA-HeLa nuclear extract

↑ ↑
NF-EI  Ets

Figure 12A

| Hela | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A | 15.46 | 16.7 | 22.61 | 22.95 | 12.07 | 8.92 | 11.39 | 17.62 | 28.98 | 28.15 | 21.31 | 17.39 | 14.2 | 17.23 | 21.92 | 22.17 | 77.28 |
| B | 10.06 | 10.82 | 13.53 | 14.05 | 10.59 | 10.51 | 14.08 | 17.59 | 18.09 | 16.99 | 18.74 | 14.89 | 12.47 | 13.17 | 14.78 | 13.86 | 77.12 |
| C | 15.24 | 18.3 | 18.1 | 19.57 | 18.34 | 20.43 | 16.05 | 20.18 | 26.6 | 27.86 | 22.65 | 18.44 | 14.14 | 14.76 | 19.91 | 18.82 | 68.98 |
| D | 11.7 | 12.35 | 12.3 | 13.4 | 13.52 | 13.52 | 11.09 | 15.57 | 18.7 | 17.73 | 16.88 | 15.4 | 12.28 | 12.5 | 12.92 | 12.16 | 69.76 |
| E | 14.66 | 12.34 | 16.63 | 17.17 | 13.79 | 15 | 12.61 | 16.67 | 36.72 | 37.54 | 14.18 | 13.86 | 12.74 | 12.81 | 15.48 | 14.5 | 63.85 |
| F | 12.68 | 10.28 | 10.55 | 11.17 | 9.66 | 10.71 | 10.84 | 14.93 | 22.98 | 22.28 | 13.51 | 13.34 | 12.34 | 12.45 | 14.71 | 14.28 | 62.87 |
| G | 21.57 | 22.18 | 15.79 | 15.65 | 15.55 | 17.06 | 12.47 | 15.3 | 17.27 | 16.05 | 27.5 | 29.53 | 34.65 | 36.09 | 16.79 | 15.52 | 68.54 |
| H | 11.99 | 12.36 | 11.84 | 11.08 | 12.84 | 13.08 | 10.69 | 13.72 | 14.91 | 13.42 | 17.43 | 15.77 | 19.07 | 17.66 | 15.06 | 16.24 | 65.92 |
| I | 15.02 | 16.81 | 17.8 | 18.87 | 13.03 | 11.97 | 13.12 | 19.72 | 14.61 | 16.58 | 18.41 | 16.93 | 14.61 | 13.53 | 59.17 | 52.3 | 65.31 |
| J | 15.33 | 13.17 | 12.18 | 11.53 | 11.66 | 11.68 | 11.32 | 18.82 | 16.1 | 15.91 | 17.93 | 16.58 | 16.19 | 14.17 | 22.59 | 22.48 | 66.31 |
| K | 24.95 | 24.46 | 12 | 11.3 | 13.2 | 13.72 | 13.96 | 18.67 | 24.52 | 24.4 | 19.04 | 17.02 | 18.27 | 14.65 | 14.12 | 13.3 | 67.11 |
| L | 15.52 | 15.71 | 11 | 10.38 | 11.53 | 12.76 | 14.23 | 16.99 | 18.56 | 17.8 | 19.35 | 18 | 17.21 | 13.33 | 12.79 | 12.3 | 54.1 |
| M | 22.73 | 23.34 | 18.2 | 16.62 | 17.74 | 19.49 | 21.31 | 22.91 | 18.15 | 17.79 | 22.82 | 22.11 | 18.4 | 15.81 | 13.07 | 12.9 | 62.16 |
| N | 12.43 | 13.7 | 14.16 | 14.11 | 14.1 | 17.87 | 19.19 | 18.96 | 15.37 | 15.33 | 19.62 | 19.4 | 17.7 | 16.22 | 13.22 | 12.12 | 68.43 |
| O | 67.86 | 72.6 | 63.6 | 64.4 | 66.58 | 76.09 | 61.65 | 64 | 59.1 | 57.89 | 63.19 | 53.98 | 66.81 | 58.05 | 66.86 | 63.92 | 77.05 |

Figure 12B

| Hela pma | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A | 17.91 | 23.38 | 39.89 | 47.35 | 20.26 | 21.59 | 25.72 | 26.67 | 39.67 | 36.11 | 25.71 | 29.74 | 32.51 | 28.28 | 30.1 | 28.25 | 69.63 |
| B | 12.96 | 14.73 | 21 | 22.68 | 16.77 | 19.72 | 21.19 | 22.99 | 22.41 | 17.24 | 19.99 | 23.94 | 22.13 | 17.91 | 19.91 | 19.85 | 67.74 |
| C | 26.15 | 26.44 | 27.03 | 28.81 | 39.4 | 45.19 | 23.43 | 27.59 | 36.97 | 32.46 | 24.86 | 25.71 | 19.34 | 17.29 | 24.25 | 24.37 | 66.39 |
| D | 14.36 | 14.83 | 19.31 | 19.51 | 20.23 | 20.99 | 15.46 | 18.23 | 22.44 | 20.07 | 17.98 | 19.9 | 15.71 | 14.86 | 15.79 | 16.77 | 70.05 |
| E | 16.83 | 17.04 | 27.94 | 28.27 | 19 | 20.34 | 16.75 | 19.11 | 41.13 | 37.38 | 16.78 | 16.51 | 15.81 | 16.34 | 20.65 | 22.66 | 68.53 |
| F | 14.85 | 14.55 | 14.76 | 14.9 | 14.84 | 15.13 | 13.85 | 14.99 | 23.97 | 23.67 | 14.7 | 13.82 | 13.5 | 14.69 | 15.54 | 18.3 | 63.47 |
| G | 28.21 | 27.45 | 32.7 | 35.35 | 26.73 | 27.49 | 17.62 | 17.79 | 17.82 | 16.99 | 32.46 | 31.43 | 55.59 | 50.71 | 18.07 | 17.97 | 71.12 |
| H | 16.2 | 13.68 | 16.76 | 16.43 | 17.02 | 17.37 | 14.53 | 16.21 | 17.78 | 16.41 | 18.69 | 17.39 | 19.93 | 24.67 | 16.04 | 15.5 | 59.24 |
| I | 20.43 | 19.47 | 24.05 | 25.33 | 18.77 | 15.88 | 22.39 | 24.89 | 22.74 | 20.67 | 19.14 | 19.32 | 13.31 | 14.62 | 73.81 | 65.19 | 68.45 |
| J | 13.93 | 12.7 | 13.3 | 13.06 | 12.63 | 12.76 | 14.25 | 18.29 | 18.53 | 16.34 | 16.98 | 18.17 | 15.36 | 16.86 | 32.75 | 30.48 | 66.33 |
| K | 28.72 | 30.5 | 13.21 | 13.12 | 14.27 | 14.47 | 17.34 | 19.26 | 34.33 | 32.69 | 14.94 | 15.89 | 16.17 | 16.82 | 21.27 | 21.9 | 73.54 |
| L | 16.2 | 16.45 | 13.23 | 12.93 | 13.18 | 12.44 | 14 | 15.47 | 19.41 | 17.18 | 13.59 | 12.37 | 13.53 | 14.32 | 13.96 | 15.79 | 67.72 |
| M | 24.34 | 24.35 | 23.93 | 23.27 | 21.3 | 20.19 | 19.08 | 22.07 | 19.5 | 16.08 | 15.78 | 13.72 | 11.84 | 12.89 | 12.77 | 15.08 | 73.48 |
| N | 12.07 | 12.63 | 14.83 | 15.59 | 15.35 | 14.97 | 13.19 | 17.69 | 18.1 | 16.11 | 16.31 | 15.02 | 11.58 | 12.75 | 12.6 | 13.93 | 69.8 |
| O | 54.81 | 60.46 | 66.42 | 62.38 | 62 | 61.46 | 56.81 | 64.85 | 68.79 | 67.61 | 65.06 | 59.81 | 54.46 | 59.18 | 71.48 | 69.25 | 78.3 |

Figure 12C

| Ratio of pma vs non pma | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A | 1.16 | 1.40 | 1.76 | 2.06 | 1.68 | 2.42 | 2.26 | 1.51 | 1.37 | 1.28 | 1.21 | 1.71 | 2.29 | 1.64 | 1.37 | 1.27 | 0.90 |
| B | 1.29 | 1.36 | 1.55 | 1.61 | 1.56 | 1.83 | 1.50 | 1.31 | 1.24 | 1.01 | 1.07 | 1.61 | 1.77 | 1.36 | 1.35 | 1.43 | 0.88 |
| C | 1.72 | 1.44 | 1.49 | 1.47 | 2.15 | 2.21 | 1.46 | 1.37 | 1.39 | 1.17 | 1.10 | 1.39 | 1.37 | 1.17 | 1.22 | 1.29 | 0.96 |
| D | 1.23 | 1.20 | 1.57 | 1.46 | 1.50 | 1.55 | 1.39 | 1.17 | 1.20 | 1.13 | 1.07 | 1.29 | 1.28 | 1.19 | 1.22 | 1.38 | 1.00 |
| E | 1.15 | 1.38 | 1.68 | 1.65 | 1.38 | 1.36 | 1.33 | 1.15 | 1.12 | 1.00 | 1.18 | 1.19 | 1.24 | 1.28 | 1.33 | 1.56 | 1.07 |
| F | 1.17 | 1.42 | 1.40 | 1.33 | 1.54 | 1.41 | 1.28 | 1.00 | 1.04 | 1.06 | 1.09 | 1.04 | 1.09 | 1.18 | 1.06 | 1.28 | 1.01 |
| G | 1.31 | 1.24 | 2.07 | 2.26 | 1.72 | 1.61 | 1.41 | 1.18 | 1.19 | 1.22 | 1.18 | 1.06 | 1.60 | 1.40 | 1.08 | 1.16 | 1.04 |
| H | 1.35 | 1.11 | 1.42 | 1.48 | 1.33 | 1.33 | 1.36 | 1.26 | 1.36 | 1.25 | 1.07 | 1.10 | 1.05 | 1.08 | 1.07 | 0.95 | 0.90 |
| I | 1.36 | 1.16 | 1.35 | 1.34 | 1.29 | 1.33 | 1.71 | 1.09 | 1.15 | 1.03 | 1.04 | 1.14 | 0.91 | 1.19 | 1.25 | 1.25 | 1.03 |
| J | 0.91 | 0.96 | 1.09 | 1.13 | 1.08 | 1.09 | 1.26 | 1.03 | 1.40 | 1.34 | 0.95 | 1.10 | 0.95 | 1.15 | 1.45 | 1.36 | 0.99 |
| K | 1.15 | 1.25 | 1.10 | 1.16 | 1.08 | 1.05 | 1.24 | 0.91 | 1.05 | 0.97 | 0.78 | 0.93 | 0.89 | 1.07 | 1.51 | 1.65 | 1.36 |
| L | 1.04 | 1.05 | 1.20 | 1.25 | 1.14 | 0.97 | 0.98 | 0.96 | 1.07 | 0.90 | 0.70 | 0.69 | 0.79 | 0.82 | 1.09 | 1.28 | 1.09 |
| M | 1.07 | 1.04 | 1.31 | 1.40 | 1.20 | 1.04 | 0.90 | 0.93 | 1.18 | 1.05 | 0.69 | 0.62 | 0.64 | 0.79 | 0.98 | 1.17 | 1.07 |
| N | 0.97 | 0.92 | 1.05 | 1.10 | 1.09 | 0.84 | 0.69 | 1.01 | 1.16 | 1.17 | 0.83 | 0.77 | 0.65 | 1.02 | 0.96 | 1.15 | 1.02 |
| O | 0.96 | 0.83 | 1.04 | 0.97 | 0.93 | 0.81 | 0.92 | 1.01 | 1.16 | 1.17 | 1.03 | 1.11 | 0.82 | 1.02 | 1.07 | 1.08 | 1.02 |

Figure 14A
A431 nuclear extract
Figure 14B
PMA-A431 nuclear extract
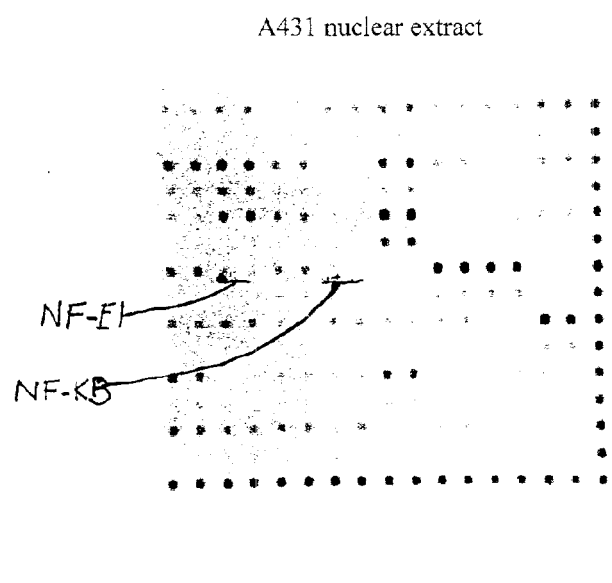
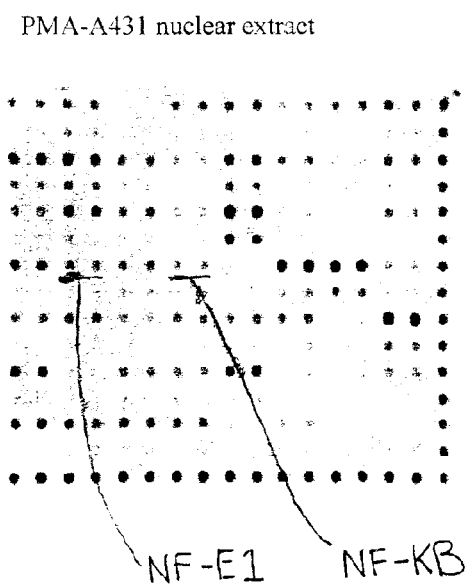

Figure 16A
Figure 16B
Jurkat nuclear extract
PMA-Jurkat nuclear extract
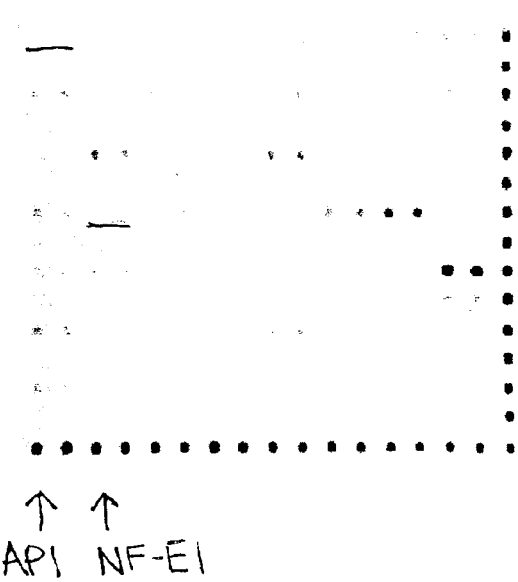
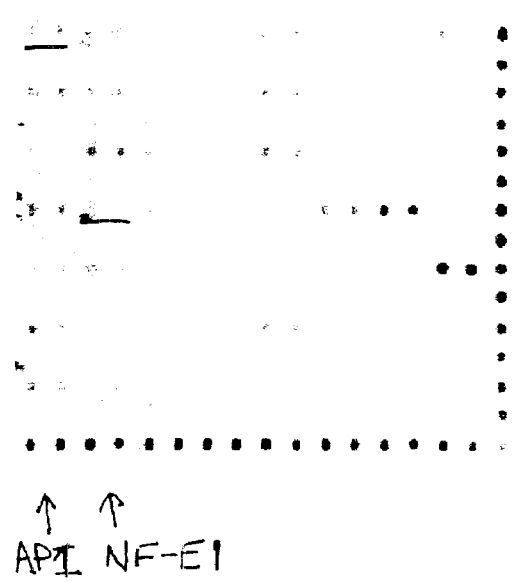

HeLa

A431

Jurkat

K562

Y79

METHOD AND KIT FOR ISOLATING DNA PROBES THAT BIND TO ACTIVATED TRANSCRIPTION FACTORS

FIELD OF THE INVENTION

The present invention relates to methods for detecting activated transcription factors in a cell sample. More specifically, the invention relates to methods for detecting multiple different activated transcription factors in a cell sample at the same time and uses arising there from.

DESCRIPTION OF RELATED ART

All living organisms use nucleic acids (DNA and RNA) to encode the genes which make up the genome for that organism. Each gene encodes a protein that may be produced by the organism through expression of the gene.

It is important to note that the mere presence of a gene in a cell does not communicate the functionality of that gene to the cell. Rather, it is only when the gene is expressed and a protein is produced that the functionality of the gene encoding the protein is conveyed.

The systems that regulate gene expression respond to a wide variety of developmental and environmental stimuli, thus allowing each cell type to express a unique and characteristic subset of its genes, and to adjust the dosage of particular gene products as needed. The importance of dosage control is underscored by the fact that targeted disruption of key regulatory molecules in mice often results in drastic phenotypic abnormalities [Johnson, R. S., et al., Cell, 71:577–586 (1992)], just as inherited or acquired defects in the function of genetic regulatory mechanisms contribute broadly to human disease.

The importance of controlled gene expression in human disease and the information available to date relating to the mechanisms of gene regulation have fueled efforts aimed at discovering ways of overriding endogenous regulatory controls or of creating new signaling circuitry in cells [Belshaw, P. J., et al., Proc. Natl. Acad. Sci. USA, 93:4604–4607 (1996); Ho, S. H., et al., Nature (London), 382:822–826 (1996); Rivera, V. M., et al., Nat. Med., 2:1028–1032; Spencer, D. M., et al., Science, 262:1019–1024 (1993)].

Critical to this research are effective tools for monitoring gene expression. It is therefore of interest to be able to rapidly and accurately determine the relative expression of different genes in different cells, tissues and organisms, over time, and under various conditions, treatments and regimes. As will be described herein in greater detail, there are a great many applications that arise from being able to effectively monitor which genes are being expressed by a given cell at a given time.

Standard molecular biology techniques have been used to analyze the expression of genes in a cell by measuring DNA. These techniques include PCR, northern blot analysis, or other types of DNA probe analysis such as in situ hybridization. Each of these methods allows one to analyze the transcription of only known genes and/or small numbers of genes at a time. Nucl. Acids Res. 19, 7097–7104 (1991); Nucl. Acids Res. 18, 4833–4842 (1990); Nucl. Acids Res. 18, 2789–2792 (1989); European J. Neuroscience 2, 1063–1073 (1990); Analytical Biochem. 187, 364–373 (1990); Genet. Annal Techn. Appl. 7, 64–70 (1990); GATA 8(4), 129–133 (1991); Pro. Natl. Acad. Sci. USA 85, 1696–1700 (1988); Nucl. Acids Res. 19, 1954 (1991); Proc. Natl. Acad. Sci. USA 88, 1943–1947 (1991); Nucl. Acids Res. 19, 6123–6127 (1991); Proc. Natl. Acad. Sci. USA 85, 5738–5742 (1988); Nucl. Acids Res. 16, 10937 (1988).

Gene expression has also been monitored by measuring levels of mRNA. Since proteins are transcribed from mRNA, it is possible to detect transcription by measuring the amount of mRNA present. One common method, called "hybridization subtraction", allows one to look for changes in gene expression by detecting changes in mRNA expression. Nucl. Acids Res. 19, 7097–7104 (1991); Nucl. Acids Res. 18, 4833–4842 (1990); Nucl. Acids Res. 18, 2789–2792 (1989); European J. Neuroscience 2, 1063–1073 (1990); Analytical Biochem. 187, 364–373 (1990); Genet. Annal Techn. Appl. 7, 64–70 (1990); GATA 8(4), 129–133 (1991); Proc. Natl. Acad. Sci. USA 85, 1696–1700 (1988); Nucl. Acids Res. 19, 1954 (1991); Proc. Natl. Acad. Sci. USA 88, 1943–1947 (1991); Nucl. Acids Res. 19, 6123–6127 (1991); Proc. Natl. Acad. Sci. USA 85, 5738–5742 (1988); Nucl. Acids Res. 16, 10937 (1988).

Gene expression has also been monitored by measuring levels of gene product, (i.e., the expressed protein), in a cell, tissue, organ system, or even organism. Measurement of gene expression by measuring the protein gene product may be performed using antibodies known to bind to a particular protein to be detected. A difficulty arises in needing to generate antibodies to each protein to be detected. Measurement of gene expression via protein detection may also be performed using 2-dimensional gel electrophoresis, wherein proteins can be, in principle, identified and quantified as individual bands, and ultimately reduced to a discrete signal. In order to positively analyze each band, each band must be excised from the membrane and subjected to protein sequence analysis using Edman degradation. Unfortunately, it tends to be difficult to isolate a sufficient amount of protein to obtain a reliable sequence. In addition, many of the bands contain more than one discrete protein.

A further difficulty associated with quantifying gene expression by measuring an amount of protein gene product in a cell is that protein expression is an indirect measure of gene expression. It is impossible to know from a protein present in a cell when that protein was expressed by the cell. As a result, it is hard to determine whether protein expression changes over time due to cells being exposed to different stimuli.

Gene expression has also been monitored by measuring the amount of particular activated transcription factors present in a cell. Transcription in a cell is controlled by proteins, referred to herein as "activated transcription factors" which bind to DNA at sites outside the core promoter for the gene and activate transcription. Since activated transcription factors activate transcription, detection of their presence is useful for measuring gene expression. Transcriptional activators are found in prokaryotes, viruses, and eukaryotes, including fungi, plants, and animals, including mammals, providing a wide range of therapeutic targets.

The regulatory mechanisms controlling the transcription of protein-coding genes by RNA polymerase II have been extensively studied. RNA polymerase II and its host of associated proteins are recruited to the core promoter through non-covalent contacts with sequence-specific DNA binding proteins [Tjian, R. and Maniatis, T., Cell, 77:5–8 (1994); Stringer, K. F., Nature (London), 345:783–786 (1990)]. An especially prevalent and important subset of such proteins, known as transcription factors, typically bind DNA at sites outside the core promoter and activate transcription through space contacts with components of the transcriptional machinery, including chromatin remodeling proteins [Tjian, R. and Maniatis, T., Cell, 77:5–8 (1994); Stringer, K. F., Nature (London), 345:783–786 (1990); Bannister, A. J. and Kouzarides, T., Nature, 384:641–643 (1996); Mizzen, C. A., et al., Cell, 87:1261–1270 (1996)]. The DNA-binding and activation functions of transcription factors generally reside on separate domains whose operation is portable to heterologous fusion proteins [Sadowski, I., et al., Nature, 335:563–564 (1988)]. Though it is believed that activation domains are physically associated with a DNA-binding domain to attain proper function, the linkage between the two need not be covalent [Belshaw, P. J., et al., Proc. Natl. Acad. Sci. USA, 93:4604–4607 (1996); Ho, S. H., et al., Nature (London), 382:822–826 (1996)]. In many instances, the activation domain does not appear to contact the transcriptional machinery directly, but rather through the intermediacy of adapter proteins known as coactivators [Silverman, N., et al., Proc. Natl. Acad. Sci. USA, 91:11005–11008 ((1994); Arany, Z., et al., Nature (London), 374:81–84 (1995)].

One of the difficulties associated with measuring gene expression by measuring transcription factors is that one must measure the subset of transcription factors which are "activated." Certain post-transcriptional modifications occur which render transcription factors "active" in the sense that they are capable of binding to DNA. It is thus necessary to distinguish between activated and non-activated transcription factors so that the "activated transcription factors" can be selectively measured.

Several different methods have been developed for detecting activated transcription factors. One method involves using antibodies selective for activated transcription factors over inactive forms of the transcription factor. This method is impractical for detecting multiple different activated transcription factors due to difficulties associated with developing numerous different antibodies having the requisite bind specificities.

Another method for detecting activated transcription factors involves measuring DNA-transcription factor complexes through a gel shift assay. [Ausebel, F. M. et al eds (1993) Current Protocols in Molecular Biology Vol.2 Greene Publishing Associates, Inc. and John Wiley and Sons, Inc., New York]. According to this method, a sample containing an activated transcription factor is contacted with a DNA probe that comprises a recognition sequence for the transcription factor. A complex between the activated transcription factor and the DNA probe is formed. The DNA-protein complex is detected by a gel-shift assay. Since individual gel shift assays must be performed for each activated transcription factor-DNA complex, this method is currently impractical for measuring multiple different activated transcription factors at the same time.

U.S. Pat. Nos. 6,066,452 and 5,861,246 describe methods for determining DNA binding sites for DNA-binding proteins. The DNA binding sites may then be used as probes to isolate DNA-binding proteins. Similarly, PCT Publication No. WO 00/04196 describes methods for identifying cis acting nucleic acid elements as well as methods for isolating nucleic acid binding factors.

SUMMARY OF THE INVENTION

The present invention relates to methods and kits for isolating DNA probes that bind to activated transcription factors.

In one embodiment, a method is provided which comprises: contacting a biological sample with a library of double stranded DNA probes under conditions where DNA probe-transcription factor complexes are formed between the DNA probes and activated transcription factors present in the biological sample; separating DNA probe-transcription factor complexes from non-complexed DNA probes in the library using an agarose gel separation; excising a portion of the agarose gel comprising the separated DNA probe-transcription factor complexes; and isolating the DNA probes from the excised portion of the agarose gel.

In another embodiment, a method is provided which comprises: contacting a biological sample with a library of double stranded DNA probes under conditions where DNA probe-transcription factor complexes are formed between the DNA probes and activated transcription factors present in the biological sample; separating DNA probe-transcription factor complexes from non-complexed DNA probes in the library using an agarose gel separation; excising a portion of the agarose gel comprising the separated DNA probe-transcription factor complexes; isolating the DNA probes from the excised portion of the agarose gel; and identifying which of the DNA probes in the library are isolated.

In another embodiment, a kit is provided which comprises: a library of double stranded DNA probes, each probe comprising a recognition sequence to which an activated transcription factor is capable of binding and forming a DNA probe-transcription factor complex, the DNA probes in the library capable of forming DNA probe-transcription factor complexes with multiple different activated transcription factors; and instructions for separating DNA probe-transcription factor complexes from non-complexed DNA probes in the library by agarose gel separation.

Kits are also provided for DNA probe libraries for detecting activated transcription factors.

In one embodiment, the kit comprises: first and second libraries of double stranded DNA probes, each probe in the first and second libraries comprising a recognition sequence to which an activated transcription factor is capable of binding and forming a DNA probe-transcription factor complex, the DNA probes in the library capable of forming DNA probe-transcription factor complexes with multiple different activated transcription factors; wherein the probes of the first library further comprise a first detectable marker and the probes of the second library further comprise a second detectable marker that is different than the first detectable marker.

Methods, arrays and kits are also provided for detecting activated transcription factors using a hybridization array.

In one embodiment, a method is provided which comprises: taking a library of double stranded transcription factor probes, the transcription factor probes each comprising a recognition sequence capable of binding to an activated transcription factor, the recognition sequence varying within the library for binding to different activated transcription factors; contacting a biological sample with the library of double stranded DNA probes under conditions where DNA probe-transcription factor complexes are formed between the DNA probes and activated transcription factors present in the biological sample; isolating the transcription factor probes from the transcription factor probe-transcription factor complexes formed; and identifying which transcription factor probes in the library formed complexes by taking an array of immobilized hybridization probes capable of hybridizing to at least one of the strands of the different double stranded transcription factor probes in the library and contacting the isolated transcription factor probes with the array under conditions suitable for hybridization of the strands of the different double stranded transcription factor probes to the hybridization probes in the array.

In another embodiment, a hybridization array is provided for use in identifying which of a plurality of different activated transcription factors are present in a biological sample by immobilizing transcription factor probes that form transcription factor probe-transcription factor complexes with different activated transcription factors, the array comprising: a substrate; and a plurality of hybridization probes immobilized on a surface of the substrate such that different hybridization probes are positioned in different defined regions on the surface, the different hybridization probes comprising a different transcription factor probe binding region capable of immobilizing a different transcription factor probe to the array, the transcription factor probe binding region comprising at least two copies of a complement to a portion of a recognition sequence comprised on the transcription factor probe. The hybridization array may optionally further comprise an internal standard. For example, the array may further comprise biotinylated DNA which is employed as an internal standard.

In another embodiment, a kit is provided for use in identifying which of a plurality of different activated transcription factors are present in a biological sample by isolating and immobilizing transcription factor probes that form transcription factor probe-transcription factor complexes with different activated transcription factors, the kit comprising: a hybridization array comprising a substrate, and a plurality of hybridization probes immobilized on a surface of the substrate such that different hybridization probes are positioned in different defined regions on the surface, the different hybridization probes comprising a different transcription factor probe binding region capable of immobilizing a different transcription factor probe to the array, the transcription factor probe binding region comprising at least two copies of a compliment to a portion of a recognition sequence comprised on the transcription factor probe; and instructions for separating DNA probe-transcription factor complexes from non-complexed DNA probes in the library by agarose gel separation.

Methods for characterizing cell types based on which activated transcription factors are present in a sample are also provided.

In one embodiment, a method is provided which comprises: taking a library of double stranded transcription factor probes, the transcription factor probes each comprising a recognition sequence capable of binding to an activated transcription factor, the recognition sequence varying within the library for binding to different activated transcription factors native to different cell types; contacting a biological sample with the library of double stranded DNA probes under conditions where DNA probe-transcription factor complexes are formed between the DNA probes and activated transcription factors present in the biological sample; isolating the transcription factor probes from the transcription factor probe-transcription factor complexes formed; identifying which transcription factor probes in the library formed complexes by taking an array of immobilized hybridization probes capable of hybridizing to at least one of the strands of the different double stranded transcription factor probes in the library and contacting the isolated transcription factor probes with the array under conditions suitable for hybridization of the strands of the different double stranded transcription factor probes to the hybridization probes in the array; and identifying a cell type of the biological sample based on which transcription factor probes are identified.

Methods for identifying a disease state based on which activated transcription factors are present in a biological sample are also provided.

In one embodiment, the method comprises taking a library of double stranded transcription factor probes, the transcription factor probes each comprising a recognition sequence capable of binding to an activated transcription factor, the recognition sequence varying within the library for binding to different activated transcription factors native to different cell types; identifying which activated transcription factors are present in a nuclear extract of a test sample of cells by: contacting the nuclear extract of the test sample with the library of double stranded DNA probes under conditions where DNA probe-transcription factor complexes are formed between the DNA probes and activated transcription factors present in the test sample, isolating the transcription factor probes from the transcription factor probe-transcription factor complexes formed, and identifying which transcription factor probes in the library formed complexes by taking an array of immobilized hybridization probes capable of hybridizing to at least one of the strands of the different double stranded transcription factor probes in the library and contacting the isolated transcription factor probes with the array under conditions suitable for hybridization of the strands of the different double stranded transcription factor probes to the hybridization probes in the array; identifying which activated transcription factors are present in a nuclear extract of a control sample of cells by: contacting the nuclear extract of the control sample with the library of double stranded DNA probes under conditions where DNA probe-transcription factor complexes are formed between the DNA probes and activated transcription factors present in the control sample, isolating the transcription factor probes from the transcription factor probe-transcription factor complexes formed, and identifying which transcription factor probes in the library formed complexes by taking an array of immobilized hybridization probes capable of hybridizing to at least one of the strands of the different double stranded transcription factor probes in the library and contacting the isolated transcription factor probes with the array under conditions suitable for hybridization of the strands of the different double stranded transcription factor probes to the hybridization probes in the array; and comparing which activated transcription factors are present in the test sample and the control sample.

Methods for screening drug candidates for modulating an activated transcription factor's activity are also provided.

In one embodiment, the method comprises: forming a plurality of test samples by contacting samples of cells with different agents; and for each test sample, identifying which of a plurality of different activated transcription factors are present by: taking a library of double stranded transcription factor probes, the transcription factor probes each comprising a recognition sequence capable of binding to an activated transcription factor, the recognition sequence varying within the library for binding to different activated transcription factors, contacting the different test sample with the library of double stranded DNA probes under conditions where DNA probe-transcription factor complexes are formed between the DNA probes and activated transcription factors present in the test samples, isolating the transcription factor probes from the transcription factor probe-transcription factor complexes formed, and identifying which transcription factor probes in the library formed complexes by taking an array of immobilized hybridization probes capable of hybridizing to at least one of the strands of the different double stranded transcription factor probes in the library and contacting the isolated transcription factor probes with the array under conditions suitable for hybridization of the strands of the different double stranded transcription factor probes to the hybridization probes in the array; and comparing the activated transcription factors present in the different test samples.

Methods for determining sequence binding requirements for an activated transcription factor are also provided.

In one embodiment, the method comprises: contacting a sample comprising an activated transcription factor with a library of double stranded DNA probes under conditions where DNA probe-transcription factor complexes are formed between the DNA probes and the activated transcription factor; separating DNA probe-transcription factor complexes from non-complexed DNA probes in the library; isolating the DNA probes from the excised portion of the agarose gel; and determining a consensus sequence for the DNA probes isolated in order to assess the binding requirements for the transcription factor.

In another embodiment, the method comprises contacting a sample comprising an activated transcription factor with a library of double stranded DNA probes under conditions where DNA probe-transcription factor complexes are formed between the DNA probes and the activated transcription factor;
  separating DNA probe-transcription factor complexes from non-complexed DNA probes in the library using an agarose gel separation; excising a portion of the agarose gel comprising the separated DNA probe-transcription factor complexes; isolating the DNA probes from the excised portion of the agarose gel; and determining a consensus sequence for the DNA probes isolated in order to assess the binding requirements for the transcription factor.

In yet another embodiment, the method comprises: contacting a sample comprising an activated transcription factor with a library of double stranded DNA probes under conditions where DNA probe-transcription factor complexes are formed between the DNA probes and the activated transcription factor;
  separating DNA probe-transcription factor complexes from non-complexed DNA probes in the library; isolating the DNA probes from the excised portion of the agarose gel; and quantifying the amount of each of the isolated DNA probes.

In yet another embodiment, the method comprises: contacting a sample comprising an activated transcription factor with a library of double stranded DNA probes under conditions where DNA probe-transcription factor complexes are formed between the DNA probes and the activated transcription factor; separating DNA probe-transcription factor complexes from non-complexed DNA probes in the library using an agarose gel separation; excising a portion of the agarose gel comprising the separated DNA probe-transcription factor complexes; isolating the DNA probes from the excised portion of the agarose gel; and quantifying the amount of each of the isolated DNA probes.

Methods are also provided for quantifying expression and activation of multiple different activated transcription factors. According to one embodiment, the method comprises: contacting a biological sample with a library of double stranded DNA probes for detecting active forms of multiple different transcription factors under conditions where DNA probe-transcription factor complexes are formed between the DNA probes and activated transcription factors present in the biological sample; isolating DNA probes from the DNA probe-transcription factor complexes; identifying which of the multiple different transcription factors are present in an activated form in the biological sample based on which DNA probes are isolated; and quantifying expression of the multiple different transcription factors from cDNA for the biological sample.

BRIEF DESCRIPTION OF THE DRAWINGS

FIG. 2 illustrates an array of hybridization probes attached to a solid support where different hybridization probes are attached to discrete, different regions of the array. A transcription factor expression signature is shown based on the distribution of where transcription factor probes hybridize and their intensity.

FIG. 3 illustrates an array of hybridization probes attached to a solid support where probes from a first sample with a first color dye and probes from a second sample with a second color dye are both contacted with the array.

FIG. 6 provides the sequences for the probes used to form the transcription factor probe library used in the experiments described in Sections 12–19 herein.

FIG. 7 depicts the layout of the array of hybridization probes employed in the experiments described in Sections 12–19 herein.

FIG. 12A provides a table of the signal intensities of regions of the array shown in FIG. 11A.

FIG. 12B provides a table of the signal intensities of regions of the array shown in FIG. 11B.

FIG. 12C provides a table with the ratios between the intensities of the regions of the arrays shown in FIGS. 12A and 12B.

FIG. 14A is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of A431 cells.

FIG. 14B is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of PMA-treated A431 cells.

FIG. 16A is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of Jurkat cells.

FIG. 16B is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of PMA-treated Jurkat cells.

DETAILED DESCRIPTION OF THE INVENTION

The present invention relates to rapid and efficient methods for identifying multiple different activated transcription factors in a biological sample at the same time. The methods of the present invention also provide for the quantification of the multiple different activated transcription factors. As will be described herein in greater detail, there are a great many applications that arise from being able to effectively monitor which genes are being expressed at a given time. With the assistance of the methods of the present invention, it is thus possible to rapidly and effectively monitor the levels of expression of multiple different genes at the same time.

The present invention also relates to various compositions, kits, and devices for use in conjunction with the various methods of the present invention.

Figure 1:
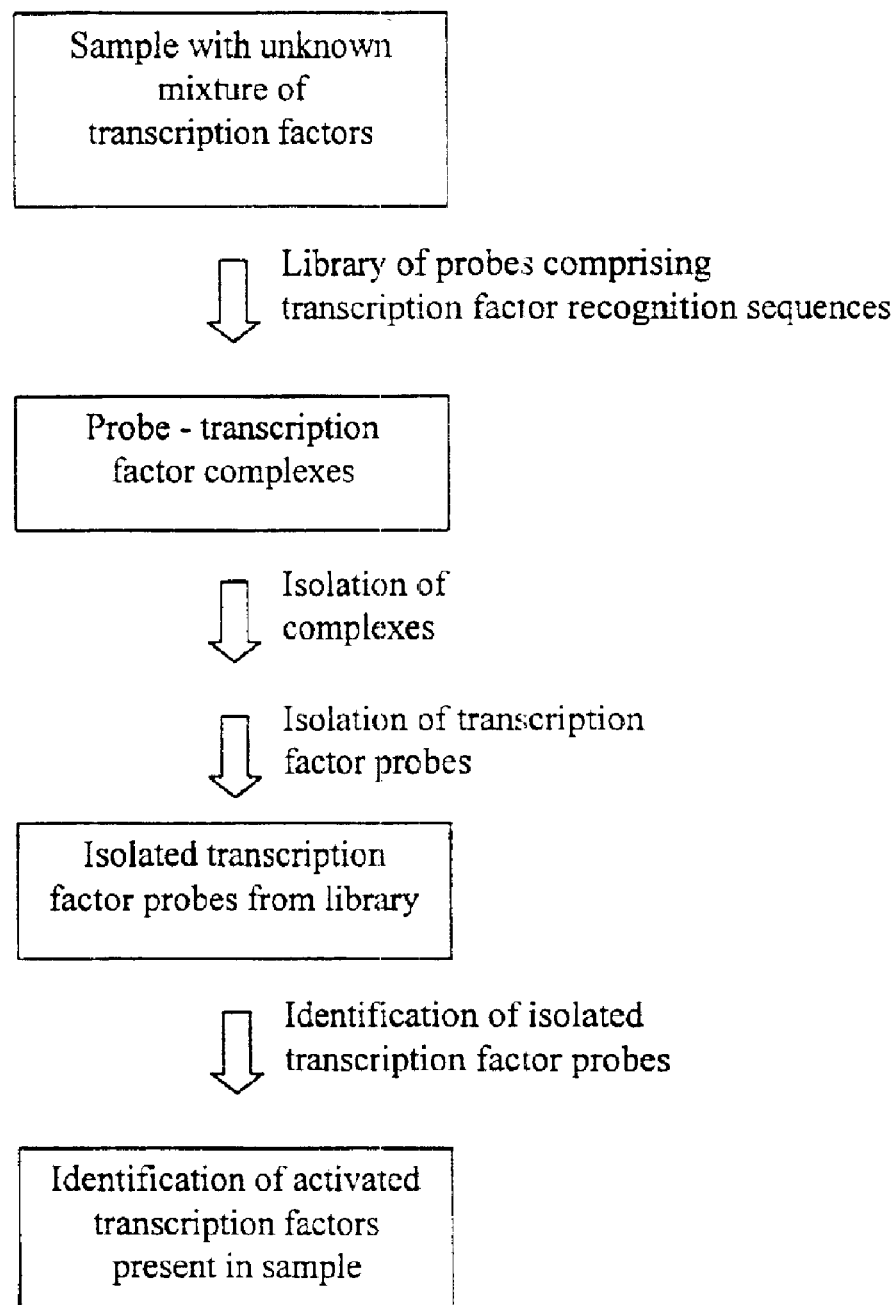
FIG. 1 provides a flow diagram for a method for identifying which of a plurality of transcription factors are activated in a given sample of cells.

FIG. 1 provides a general overview of how the present invention detects multiple different activated transcription factors and thus allows the expression of multiple different genes to be simultaneously monitored.

As illustrated, a biological sample is contacted with a library of probes. The biological sample is typically derived from a sample of cells and is preferably a nuclear extract of the cell sample. The sample contains an unknown mixture of activated transcription factors. Which activated transcription factors are present in the sample serves to indicate which genes are currently being expressed.

Information about the DNA binding specificity of transcription factors which one wishes to identify is used to design a library of transcription factor probes. In this regard, it is noted that the present invention relates to the detection, monitoring and optionally quantification of known transcription factors using a library of transcription factor probes whose sequences are known. The probes in the library are preferably double stranded. One of the strands is preferably biotin labeled at the 5' end to facilitate detection.

Each transcription factor probe in the library comprises a DNA sequence that is capable of binding to an activated transcription factor, referred to herein as the probe's recognition sequence. At least the recognition sequence varies within the library of probes such that the probes are capable of binding to a plurality of different activated transcription factors. Due to the high level binding specificity of the transcription factors, each transcription factor probe has binding specificity for a single transcription factor or family of transcription factors.

Because the present invention is used to identify known transcription factors, it is practical to use longer recognition sequences in the probes in the library as compared to what would be practical if a random library were used. As a result, at least 1%, 2%, 3%, 5%, 10%, 20%, 30%, 50% or more of the probes in the library may have recognition sequences greater than 35, 40, 45 or more base pairs in length. By using longer recognition sequences, the probes have greater binding specificity. In addition, the probes have greater binding efficiency to the transcription factors which improves the yield of probe-transcription factor complexes isolated. As a result, the method of the present invention provides a high level of sensitivity for isolating probe-transcription factor complexes, as described further herein, in combination with a high signal to noise ratio.

As a result of contacting the sample with the library of transcription factor probes, complexes are formed between activated transcription factors present in the sample and transcription factor probes in the library which have sequences that match the sequence specificity of the DNA-binding domains of the activated transcription factors. By isolating the transcription factor probe-activated transcription factor complexes, those probes from the library which bind to transcription factors in the sample are isolated.

The isolated transcription factor probes are then identified. Each probe is specific for a different transcription factor. Since only those probes from the library which form a complex with an activated transcription factor will be isolated, identification of which probes are isolated serves to identify which activated transcription factors are present. Since the presence of an activated transcription factor evidences gene expression, the above described method can be used to determine which genes were being expressed at the time the sample was taken based on which activated transcription factors are present.

The design, operation and applications for the present invention will now be described in greater detail.

1. Libraries of Transcription Factor Probes

Libraries of transcription factor probes are provided that may be used to detect activated transcription factors according to the present invention. A given library comprises a plurality of double stranded DNA probes where the DNA sequences of the probes vary within the library. The DNA sequences employed in the probes of the libraries preferably have a length between about 10 and 100 base pairs, preferably between about 10 and 75 base pairs, more preferably between about 15 and 50. Probes of longer lengths may also be used.

Each probe in the library comprises a recognition sequence which is capable of forming a probe-transcription factor complex with an activated transcription factor. Due to the high level of DNA binding specificity of transcription factors, each transcription factor will typically bind to a different DNA sequence. In some instances, a related family of transcription factors may bind to the same DNA sequence.

By designing the library of probes such that any given probe in the library includes a DNA recognition sequence which a particular activated transcription factor (or a related family of activated transcription factors) will bind to, and does not also include a DNA recognition sequence which other activated transcription factors will bind to, a given probe may be used to identify a single activated transcription factor (or a related family of activated transcription factors).

It is noted that in certain situations, individual probes may bind to more than one activated transcription factor and may nonetheless be used in the library. For example, certain probes may bind to a related family of activated transcription factors. Less than 1:1 binding specificity between probes and activated transcription factors can be readily resolved during analysis of the isolated probes.

The DNA recognition sequences used in the probes in the libraries preferably have a length between about 10 and 100 base pairs, more preferably between about 10 and 75 base pairs, more preferably between about 15 and 50 base pairs, more preferably between about 20 and 40 base pairs, and most preferably a length between about 25 and 35 base pairs.

The optimal length for the recognition sequence and the overall probe may vary somewhat depending on the particular transcription factor. Hence, one may wish to evaluate the optimal length for the recognition sequence and the probe for a given transcription factor using a traditional gel shift assay.

Because the present invention is used to identify known transcription factors, it is practical to use longer recognition sequences in the probes in the library as compared to what would be practical if a random library were used. For example, at least 1%, 2%, 3%, 5%, 10%, 20%, 30%, 50% or more of the probes in the library may have recognition sequences greater than 35, 40, 45 or more base pairs in length. By using longer recognition sequences, the probes have greater binding specificity and greater binding efficiency to the transcription factors. As a result, the method of the present invention provides a high level of sensitivity for isolating probe-transcription factor complexes, as described further herein, in combination with a high signal to noise ratio.

Selection of which DNA recognition sequences to use in a library may be based on the different transcription factors that one wishes to detect in a sample. This, in turn, may depend on the type of organism, cell, or disease state one wishes to identify and/or monitor the gene expression of. It may also depend on the different functionality that one wishes to identify or monitor.

A significant feature of the present invention is the ability to detect multiple different transcription factors at the same time. This ability arises from the number of different DNA recognition sequences used in a library, the number of different DNA recognition sequences relating directly to the number of different transcription factors that the library can be used to detect. A given library of transcription factor probes preferably has at least 2, 3, 5, 10, 20, 50, 100, 250, or more different DNA recognition sequences. The upper limit on the number of different DNA recognition sequences that may be incorporated into a library is limited only by the number of known DNA recognition sequences.

A given library of transcription factor probes may be used to detect gene expression in a single type of cell or organism or may be used to detect gene expression in multiple different types of cells or organisms. When the library is designed to detect gene expression in multiple different types of cells or organisms, the library has DNA recognition sequences for multiple different types of cells or organisms. For example, the library may include DNA recognition sequences for 2, 3, 4, 5 or more different types of cells or organisms. In one embodiment, the library includes DNA recognition sequences for 10, 20, 30, 50, or more different types of cells or organisms.

If the sample comprises cells that may be from one or more different organisms, the DNA recognition sequences used in the library may be for all or some of the different transcription factors expressed by the one or more different organisms. For example, if the library is to be used to classify an unknown type of bacterium, the library may include DNA recognition sequences for multiple different types of bacteria, thereby allowing the library to be used to classify the bacterium.

If the sample comprises cells from a particular organism, the DNA recognition sequences used in the library may be for all or some of the different transcription factors expressed by organism. If the library is to be used to classify an unknown type of cells (i.e., determine whether a growth is malignant), the library may include DNA recognition sequences for multiple different types of cells including the different types of malignant, benign, and normal cell types present in the organism.

If the sample comprises cells of a single cell type, the DNA recognition sequences used in the library may be for all or some of the different transcription factors expressed by that cell type. For example, if one wishes to monitor the expression of only a particular group of genes, such as the genes associated with a particular pathway, the library may include DNA recognition sequences for the transcription factors associated with that group of genes.

As one can see, a myriad of different libraries of probes can be assembled depending on the nature of the sample and the nature of the analysis to be performed. It is noted that different libraries may also be formed when a particularly large number of transcription factors are to be detected or when different binding conditions are needed for different groups of probes.

The probes in the library may optionally further comprise a detectable marker which allows the probe to be detected once isolated from the transcription factor probe-transcription factor complex. Since a wide variety of detection techniques may be used to identify the isolated probes, a similarly wide range of detectable markers may be used in conjunction with those different detection techniques.

The detectable marker may be any marker which can be used to determine the presence or absence of the DNA probes. In a preferred embodiment, the detectable marker is biotin and is preferably attached to one of the 5' ends of probes. Biotin probes have been found to provide a desirable high level of sensitivity.

The detectable marker may also be a dye which can be seen under natural light or with the assistance of an excitation light source to cause fluorescence. In one embodiment, the detectable marker is a fluorescent dye. Examples of fluorescent dyes that may be used include, but are not limited to fluorescein and its derivatives, rhodamine and its derivatives, dansyl, umbeliferone, acridimium, and chemiluminescent molecules such as luciferin and 2,3-dihydrophthalazinediones. The fluorescent dye may also be an energy transfer fluorescent dye.

The detectable marker may also be a molecule which binds to an analytically detectable counterpart. For example, the detectable marker may be covalently attached to or incorporated into the substrate, for example, as taught by Ward, European Patent Application No. 63,879. In such instances, the substrate is detected by adding the analytically detectable counterpart which specifically binds to the substrate, thereby enabling detection of the substrate. Examples of such detectable markers and their analytically detectable counterparts include biotin and either fluorescent or chemiluminescent avidin. Antibodies that bind to an analytically detectable antigen may also be used as the detectable marker. The detectable marker may also be a molecule which, when subjected to chemical or enzymatic modification, becomes detectable such as those disclosed in Leary, et al., Proc. Natl. Acad. Sci. (U.S.A.), 80:4045–4049 (1983).

In certain instances, it may be desirable to employ multiple different detectable markers. For example, if one wishes to classify an unknown type of cell or organism, the library may include DNA probes where different detectable markers are attached to the probes for the different types of cells. Hence, probes for transcription factors expressed by malignant cells may include a first fluorescent dye whereas probes expressed by benign cells may include a second fluorescent dye. In another example, probes for transcription factors expressed by a first type of lung cancer may include a first fluorescent dye whereas probes expressed by of a second, different type of lung cancer may include a second fluorescent dye. This allows one to rapidly visually identify the type of cell based on which detectable markers are present.

When one wishes to compare the gene expression of different groups of cells, multiple libraries may be prepared where each library contains a different detectable marker. For example, a first library labeled with a first detectable marker may be used with a first sample of cells and a second library labeled with a second detectable marker may be used with a second sample of cells. This way, the isolated probes may be analyzed together. As described in Section 6A, when an array format is used for detecting the isolated probes, the use of different detectable markers is particularly advantageous. For example, as shown in FIG. 3, transcription factor probes isolated from complexes formed from a first sample (e.g., a control sample) may have a green dye, and transcription factor probes isolated from complexes formed from a second sample (e.g., a test sample) may have a red dye. Regions in the array which are green represent genes which only the cells in the control sample are expressing, regions in the array which are red represent genes which only cells in the test sample are expressing, and regions in the array which are both green and red represent genes which cells in both the control and test samples are expressing.

2. Preparation of Sample

Nuclear extracts can be prepared from a sample of cells using the method described by Dignam, J. D., Lebovitz, R. M., and Roeder, R. G. (1983) Accurate transcription initiation by RNA polymerase II in a soluble extract from isolated mammalian nuclei. *Nucleic Acids Research* 11:1475–1489. Alternatively, a commercially available kit, such as Sigma's Nu-CLEAR Extraction Kit (cat. #N-TRACT) can be used.

3. Contacting Cell Sample with Library of Probes

Once a nuclear extract of a sample of cells is prepared, the nuclear extract is contacted with a library of probes and incubated at 15° C. for 30 min.

4. Isolation of Probe-Transcription Factor Complexes

After contacting the sample with the library of transcription factor probes, any probe-activated transcription factor complexes formed are isolated. Any isolation method which can effectively isolate the complexes may be used. Isolation is preferably performed by a form of size separation, more preferably by electrophoresis, more preferably gel electrophoresis and most preferably gel electrophoresis using an agarose gel.

One of the problems overcome by the present invention is the ability to isolate complexes of DNA probes bound to transcription factors from other probes in the library. Several methods for performing this type of isolation were attempted. However, these methods failed to provide a sufficient yield of probe-transcription factor complexes from the sample.

For example, Applicant attempted to isolate probe-transcription factor complexes by performing an ammonia precipitation. Applicant also attempted to isolate probe-transcription factor complexes by passing the sample through a nitrocellulose filter, the filter serving to immobilize proteins while allowing DNA that is not bound to protein to pass through the filter. Unfortunately, neither of these approaches provided a satisfactory yield of complexes for further characterization of the isolated probes.

Applicant also attempted to isolate probe-transcription factor complexes by using acrylamide gel electrophoresis. Unfortunately, this approach also did not provide a satisfactory yield of complexes. Without being bound by theory, it is believed that this method was hampered by the DNA probes being retained by the acrylamide gel.

Applicant successfully isolated probe-transcription factor complexes from the sample using agarose gel electrophoresis. Interestingly, despite the fact that agarose gel electrophoresis does not provide the same quality separation as other forms of gel electrophoresis (e.g., acrylamide gel electrophoresis), the resolution provided using agarose is more than sufficient to effectively separate the probe-transcription factor complexes. Meanwhile, agarose proved to have satisfactorily low retention of the DNA probes in the complex, thereby allowing the probes to be further characterized.

The separated probe-transcription factor complexes were isolated by removing the band from the gel containing the probe-transcription factor complexes.

It is noted that simultaneous isolation of multiple different probe-transcription factor complexes using a library of DNA probes is a significant departure from traditional gel-shift assays involving the use of a single probe to cause the gel shift of a single transcription factor. [Ausebel, F. M. et al eds (1993) Current Protocols in Molecular Biology Vol.2 Greene Publishing Associates, Inc. and John Wiley and Sons, Inc., New York]. In such prior gel-shift assays, since only a single transcription factor was being detected, no efforts were made to isolate the probe used to cause the gel shift. By contrast, in the present invention, since multiple probes are used in combination it is necessary to isolate the complexes in order to isolate and characterize which of the plurality of probes in the library formed a complex with a transcription factor and are present in the band.

It is also noted that simultaneous isolation of multiple different probe-transcription factor complexes by isolating and characterizing the DNA probes is also a significant departure from U.S. Pat. Nos. 6,066,452 and 5,861,246 and PCT Publication No. WO 00/04196 which describe isolation of the nucleic acid binding factors, not the probes.

The following is a detailed description of how one may isolate probe-transcription factor complexes using an agarose gel. It is noted that other separation and isolation methods may be employed without departing from the present invention.

According to one embodiment, a 2% agarose gel in 0.5×TBE is prepared. Preferably, 8 mm-wide combs are used. Each sample is mixed with 2 $\mu$l of a gel loading buffer. Table 1 provides an embodiment of a gel loading buffer that may be used.

TABLE 1

Gel shift loading buffer:

0.25 X TBE buffer: 60%
Glycerol: 40%
Bromophenol blue: 0.2% (w/v)

Add 2 ul of gel shift loading buffer and load into a 0.8 cm width lane of 2% agarose gel in 0.5% TBE. The resulting agarose gel is then run in 0.5% TBE at 120V for 16 min. The gel area containing that contains the protein/DNA complex, which will be above the blue dye and below the gel lane, is excised and transferred to a 1.5 mL tube.

5. Separation of Transcription Factor Probes from Transcription Factor-Probe Complexes Once the transcription factor probe-transcription factor complexes are separated from other proteins and DNA in the sample, for example, as described in Section 4, the transcription factor probes are separated from the excised portion of the gel.

The following is a detailed description of how one may isolate probe-transcription factor complexes from an excised portion of an agarose gel. It is noted that other isolation techniques may be employed without departing from the present invention.

It is noted that the following steps describing the isolation of the DNA probes is specifically designed for CLONTECH's NucleoTrap Kit. If another commercially available gel extraction kit is employed, the steps should be modified in accordance with that manufacturer's instructions.

1.0 mL of NT1 solution from CLONTECH's NucleoTrap Kit is added to the excised portion of the gel. The mixture is then incubated at 50° C. until the gel is totally dissolved. The tube is preferably periodically gently inverted in order to mix the contents until the gel is dissolved.

6 $\mu$l of beads from a commercially available gel extraction kit is then preferably added and the resulting mixture is incubated at room temperature for 10 min. The tube is preferably periodically gently inverted every 2–3 minutes.

The tube is then microfuged at 10,000 rpm for 30 sec. The resulting supernatant is carefully removed and the pellet resuspended in 150 $\mu$l of NT2 solution from CLONTECH's NucleoTrap Kit.

The pellet is then microfuged at 10,000 rpm for 30 sec. The resulting supernatant is then carefully removed and the pellet resuspended in 150 $\mu$l of NT3 solution from CLONTECH's NucleoTrap Kit. The pellet is then microfuged at 10,000 rpm for 30 sec. The supernatant is again removed and the pellet is allowed to air-dry for 10 min.

50 $\mu$l of dH$_2$O is then added to resuspend the pellet. The resulting mixture is incubated at room temperature for 5 min. The mixture is then gently shaken and incubated for another 5 min.

The resulting mixture is then microfuged at 10,000 rpm for 1 min. The supernatant is transferred to a fresh 1.5 ml tube. The isolated supernatant contains the DNA probes that are bound to proteins. The isolated supernatant is preferably stored on ice until proceeding to a characterization of the DNA probes.

6. Identifying Isolated Transcription Factor Probes

A variety of different methods may be used to identify which of the transcription factor probes from the library are present in the isolated probe-transcription factor complexes. These methods preferably also allow for the amount of transcription factor probes isolated to also be quantified. By identifying which transcription factor probes form complexes, one is able to determine which transcription factors are present in an activated form in the sample, the presence of an activated transcription factor evidencing expression of the gene associated with the transcription factor. By quantifying the amount of each transcription factor probe that forms a complex, one is able to determine the amount of each transcription factor present and hence the level of expression of the gene associated with that transcription factor.

One method that may be used to identify which of the transcription factor probes from the library are present in the isolated probe-transcription factor complexes is mass spectroscopy. According to this method, the length and composition of each probe can be determined. Therefore, the analyzed results show whether a specific probe is existing in the complexes and the interactions between transcription factors and binding probes can be determined.

Another method that may be used to identify which of the transcription factor probes from the library are present in the isolated probe-transcription factor complexes is based on size separation. According to this method, one varies the length of the probes in the transcription factor probe library so that it is possible to resolve the different sized probes based on a size-based separation. For example, electrophoresis may be performed in order to separate the probes based on size. Such size-based DNA separations are traditionally done with high level specificity for DNA sequencing. By identifying which transcription factor probes are present based on the size-based separation, one can determine which activated transcription factors are present and can also quantify the amount of each activated transcription factor.

Yet another method for identifying which of the probes from the transcription factor probe library formed complexes involves hybridization of the transcription factor probes with a hybridization probe comprising a complement to the transcription factor probes recognition sequence. According to this method, detection of a particular transcription factor probe is accomplished by detecting the formation of a duplex between the transcription factor probe and a hybridization probe comprising a complement to the transcription factor probe's recognition sequence.

A wide variety of assays have been developed for performing hybridization assays and detecting the formation of duplexes that may be used in the present invention. For example, hybridization probes with a fluorescent dye and a quencher where the fluorescent dye is quenched when the probe is not hybridized to a target and is not quenched when hybridized to a target oligonucleotide may be used. Such fluorescer-quencher probes are described in, for example, U.S. Pat. No. 6,070,787 and S. Tyagi et al., "Molecular Beacons: Probes that Fluoresce upon Hybridization", Dept. of Molecular Genetics, Public Health Research Institute, New York, N.Y., Aug. 25, 1995, each of which are incorporated herein by reference. By attaching different fluorescent dyes to different hybridization probes, it is possible to determine which transcription factor probes from the library formed complexes based on which fluorescent dyes are present (e.g., fluorescent dye and quencher on hybridization probe or fluorescent dye on hybridization probe and quencher on transcription factor probe). Applicant notes that one may also attach different fluorescent dyes to different transcription factor probes and use a change in fluorescence due to hybridization to a hybridization probe to determine which transcription factor probes are present (e.g., fluorescent dye and quencher on transcription factor probe or fluorescent dye on transcription factor probe and quencher on hybridization probe).

A difficulty, however, arises when using multiple different fluorescer to detect multiple different transcription factor probes. Namely, there is a limited number of different fluorescers that may be spectrally resolved. As a result, a limited number of different transcription factors can be detected at the same time, for example only as many as five to ten.

A. Hybridization Arrays for Detecting Isolated Transcription Factor Probes

A preferred assay for detecting the formation of duplexes between transcription factor probes and hybridization probes comprising their complements involves the use of an array of hybridization probes immobilized on a solid support. The hybridization probes comprise sequences that are complementary to at least a portion of the recognition sequences of the transcription factor probes and thus are able to hybridize to the different probes in a transcription factor probe library.

In order to improve enhance the sensitivity of the hybridization array, the immobilized probes preferably provide at least 2, 3, 4 or more copies of at least a portion of the recognition sequence incorporated into the transcription factor probes.

According to the present invention, the hybridization probes immobilized on the array preferably are at least 25 nucleotides in length, more preferably at least 30, 40 or 50 nucleotides in length. The immobilized hybridization probes may be 50, 75, 100 nucleotides or longer in length. In one preferred embodiment the immobilized probes are between 50 and 100 nucleotides in length.

By immobilizing hybridization probes on a solid support which comprise one or more copies of a complement to at least a portion of the recognition sequences of the transcription factor probes, the hybridization probes serve as immobilizing agents for the transcription factor probes, each different hybridization probe being designed to selectively immobilize a different transcription factor probe.

FIG. 2 illustrates an array of hybridization probes attached to a solid support where different hybridization probes are attached to discrete, different regions of the array. Each different region of the array comprises one or more copies of a same hybridization probe which incorporates a sequence that is complementary to a recognition sequence of a transcription factor probe. As a result, the hybridization probes in a given region of the array can selectively hybridize to and immobilize a different transcription factor probe based on the transcription factor probe's recognition sequence.

By detecting which regions the isolated transcription factor probes hybridize to on the array, one can determine which activated transcription factors are present in the sample and can also quantify the amount of each activated transcription factor.

These arrays can be designed and used to study transcription factor activation in a variety of biological processes, including cell proliferation, differentiation, transformation, apoptosis, drug treatment, and others described herein.

Numerous methods have been developed for attaching hybridization probes to solid supports in order to perform immobilized hybridization assays and detect target oligonucleotides in a sample. Numerous methods and devices are also known in the art for detecting the hybridization of a target oligonucleotide to a hybridization probe immobilized in a region of the array. Examples of such methods and device for forming arrays and detecting hybridization include, but are not limited to those described in U.S. Pat. Nos. 6,197,506, 6,045,996, 6,040,138, 5,424,186, 5,384, 261, each of which are incorporated herein by reference.

Several modifications may be made to the hybridization arrays known in the art in order to customize the hybridization arrays for use in detecting activated transcription factors through the characterization of isolated transcription factor probes which form a complex with the activated transcription factors.

Since the hybridization probe arrays of the present invention are designed to hybridize to the probes in the transcription factor probe library by comprising a sequence that is complementary to the transcription factor recognition sequence, the composition of the hybridization probes in the array should complement the recognition sequences of the probes in the transcription factor probe library. As discussed in Section 1, a variety of different libraries of transcription factor probes are provided that may be used to detect activated transcription factors according to the present invention.

Selection of the sequences used in the hybridization probes may be based on the different transcription factors that one wishes to detect in a sample. This, in turn, may depend on the type of organism, cell, or disease state one wishes to identify and/or monitor the gene expression of.

A significant feature of the present invention is the ability to detect multiple different transcription factors at the same time. This ability arises from the number of different DNA recognition sequences used in a library, the number of different DNA recognition sequences relating directly to the number of different transcription factors that the library can be used to detect. A given array of hybridization probes preferably has complements for at least 2, 3, 5, 10, 20, 30, 50, 100, 250 or more different DNA recognition sequences. The upper limit on the number of different DNA recognition sequences that the array of hybridization probes may detect is limited only by the number of known DNA recognition sequences and hence the number of known complements to the DNA recognition sequences.

A given array of hybridization probes may be used to detect gene expression in a single type of cell or organism or may be used to detect gene expression in multiple different types of cells or organisms. When the array is designed for use with a library designed to detect gene expression in multiple different types of cells or organisms, the array may include complements to DNA recognition sequences for multiple different types of cells or organisms. For example, the array may include complements to DNA recognition sequences for 2, 3, 4, 5 or more different types of cells or organisms. In one embodiment, the array may include complements to DNA recognition sequences for 10, 20, 30, 50, or more different types of cells or organisms.

If the sample to be analyzed comprises cells that may be from one or more different organisms, the DNA recognition sequences used in the library may be for all or some of the different transcription factors expressed by the one or more different organisms. For example, if library is to be used to classify an unknown type of bacterium, the library may include DNA recognition sequences for multiple different types of bacteria, thereby allowing the library to be used to classify the bacterium. Accordingly, the array used in combination with the library would include complements to DNA recognition sequences for multiple different types of bacteria.

If the sample comprises cells from a particular organism, the DNA recognition sequences used in the library may be for all or some of the different transcription factors expressed by organism. Accordingly, the array used in combination with the library would include complements to DNA recognition sequences for the different transcription factors expressed by organism.

If the library is to be used to classify an unknown type of cells (i.e., determine whether a growth is malignant), the library may include DNA recognition sequences for multiple different types of cells including the different types of malignant, benign, and normal cell types present in the organism. Accordingly, the array used in combination with the library would include complements to DNA recognition sequences for the multiple different types of cells.

If the sample comprises cells of a single cell type, the DNA recognition sequences used in the library may be for all or some of the different transcription factors expressed by that cell type. Accordingly, the array used in combination with the library would include complements to the recognition sequences for all or some of the different transcription factors expressed by that cell type.

i. Procedure for Performing Hybridization Using Array

Provided below is a description of a procedure that may be used to hybridize isolated transcription factor probes to a hybridization array. It is noted that the below procedure may be varied and modified without departing from other aspects of the invention.

An array membrane having hybridization probes attached for the transcription factor probes is first placed into a hybridization bottle. The membrane is then wet by filling the bottle with deionized $H_2O$. After wetting the membrane, the water is decanted. Membranes that may be used as array membranes include any membrane to which a hybridization probe may be attached. Specific examples of membranes that may be used as array membranes include, but are not limited to NYTRAN membrane (Schleicher & Schuell), BIODYNE membrane (Pall), and NYLON membrane (Roche Molecular Biochemicals).

5 ml of prewarmed hybridization buffer is then added to each hybridization bottle containing an array membrane. The bottle is then placed in a hybridization oven at 42° C. for 2 hr. An example of a hybridization buffer that may be used is EXPHYP by Clonetech.

After incubating the hybridization bottle, a thermal cycler may be used to denature the hybridization probes by heating the probes at 90° C. for 3 min, followed by immediately chilling the hybridization probes on ice.

The isolated probe-transcription factors complexes are then added to the hybridization bottle. Hybridization is preferably performed at 42° C. overnight.

After hybridization, the hybridization mixture is decanted from the hybridization bottle. The membrane is then washed repeatedly.

In one embodiment, washing includes using 60 ml of a prewarmed first hybridization wash which preferably comprises 2×SSC/0.5% SDS. The membrane is incubated in the presence of the first hybridization wash at 42° C. for 20 min with shaking. The first hybridization wash solution is then decanted and the membrane washed a second time. A second hybridization wash, preferably comprising 0.1×SSC/0.5% SDS is then used to wash the membrane further. The membrane is incubated in the presence of the second hybridization wash at 42° C. for 20 min with shaking. The second hybridization wash solution is then decanted and the membrane washed a second time.

ii. Procedure for Detecting Array Hybridization

The following describes a procedure that may be used to detect isolated transcription factor probes isolated on the hybridization array. It is noted that each membrane should be separately hybridized, washed and detected in separate containers in order to prevent cross contamination between samples. It is also noted that it is preferred that the membrane is not allowed to dry during detection.

According to the procedure, the membrane is carefully removed from the hybridization bottle and transferred to a new container containing 30 ml of 1× blocking buffer. The dimensions of each container is preferably about 4.5"×3.5", equivalent in size to a 200 μL pipette-tip container. Table 2 provides an embodiment of a blocking buffer that may be used.

TABLE 2

| 1 X Blocking Buffer: |
| --- |
| Blocking reagent: 1% |
| 0.1 M Maleic acid |
| 0.15 M NaCl |
| Adjusted with NaOH to pH 7.5 |

It is noted that the array membrane may tend to curl adjacent its edges. It is desirable to keep the array membrane flush with the bottom of the container.

The array membrane is incubated at room temperature for 30 min with gentle shaking. 1 ml of blocking buffer is then transferred from each membrane container to a fresh 1.5 ml tube. 3 μl of Streptavidin-AP conjugate is then added to the 1.5 ml tube and is mixed well. The contents of the 1.5 ml tube is then returned to the container and the container is incubated at room temperature for 30 min.

The membrane is then washed three times at room temperature with 40 ml of 1× detection wash buffer, each 10 min. Table 3 provides an embodiment of a 1× detection wash buffer that may be used.

TABLE 3

| 1 X Detection wash buffer: |
| --- |
| 10 mM Tris-HCl, pH 8.0 |
| 150 mM NaCl |
| 0.05% Tween-20 |

30 ml of 1× detection equilibrate buffer is then added to each membrane and the combination is incubated at room temperature for 5 min. Table 4 provides an embodiment of a 1× detection equilibrate buffer that may be used.

TABLE 4

| 1 X Detection equilibrate buffer: |
| --- |
| 0.1 M Tris-HCl pH 9.5 |
| 0.1 M NaCl |

The resulting membrane is then transferred onto a transparency film. 3 ml of CPD-Star substrate, produced by Applera, Applied Biosystems Division, is then pipetted onto the membrane.

A second transparency film is then placed over the first transparency. It is important to ensure that substrate is evenly distributed over the membrane with no air bubbles. The sandwich of transparency films are then incubated at room temperature for 5 min.

The CPD-Star substrate is then shaken off and the films are wiped. The membrane is then exposed to Hyperfilm ECL, available from Amersham-Pharmercia. Alternatively, a chemiluminescence imaging system may be used such as the ones produced by ALPHA INNOTECH. It may be desirable to try different exposures of varying lengths of time (e.g., 2–10 min).

The hybridization array may be used to obtain a quantitative analysis of the amount of transcription factor probe present. For example, if a chemiluminescence imaging system is being used, the instructions that come with that system's software should be followed. If Hyperfilm ECL is used, it may be necessary to scan the film to obtain numerical data for comparison.

iii. Normalization of Data from Array Hybridization

One of the advantages provided by array hybridization for detecting isolated transcription factor probes is the ability to simultaneously analyze whether multiple different activated transcription factors are present.

A further advantage provided is that the system allows one to compare a quantification of multiple different activated transcription factors between two or more samples. When two or more arrays from multiple samples are compared, it is desirable to normalize them.

In order to facilitate normalization of the arrays, an internal standard may be used so that the intensity of detectable marker signals between arrays can be normalized. In certain instances, the internal standard may also be used to control the time used to develop the detectable marker.

In one embodiment, the internal standard for normalization is biotinylated DNA which is spotted on a portion of the array, preferably adjacent one or more sides of the array. For example, biotin-labeled ubiquitin DNA may be positioned on the bottom line and last column of the array. In order to normalize two or more arrays for comparison of results, the exposure time for each array should be adjusted so that the signal intensity in the region of the biotinylated DNA is approximately equivalent on both arrays.

7. Use of Multiple Libraries in Combination to Compare Gene Expression Between Different Samples When an array format is used for detecting the isolated probes, it may be desirable to use multiple libraries labeled with different detectable markers in order to facilitate comparison between samples. For example, as shown in FIG. 3, probes from a first sample (e.g., a control sample) may have a green dye, and probes from a second sample (e.g., a test sample) may have a red dye. Both probes are separated from their bound complexes, mixed, and hybridized to a single array. Green spots in the array represent genes which only the cells in the control sample are expressing, and red spots in the array represent genes which only cells in the test sample are expressing. When both dyes hybridize to the same spot in an equal amount, the balanced mixture of green and red appears as yellow in the array, representing genes which cells in both the control and test samples are expressing.

One embodiment of this application of the present invention thus relates to a method for comparing gene expression between a test sample and a control sample, the method comprising forming transcription factor probe-activated transcription factors complexes using the test sample and a first library of transcription factor probes having a first detectable marker; forming transcription factor probe-activated transcription factors complexes using the control sample and a second library of transcription factor probes having the same nucleic acid sequences as the first library but having a second, different detectable marker; isolating the transcription factor probes from the first library which formed complexes involving transcription factors from the test sample; isolating the transcription factor probes from the second library which formed complexes involving transcription factors from the control sample; and detecting the isolated transcription factor probes from the first and second libraries using a same hybridization array.

Another embodiment of this application of the present invention relates to a kit comprises the first and second library of transcription factor probes. The kit may optionally further include a hybridization array comprising complements to the transcription factor probes. The kit may also include instructions for isolating the transcription factor probe-activated transcription factor complexes using agarose gel.

8. Applications for Monitoring Gene Expression via Detection of Activated Transcription Factors By better understanding which cells express which genes and how different conditions influence gene expression, fundamental questions of biology can be answered. Thus, by being able to rapidly and efficiently detect multiple activated transcription factors at the same time, the present invention avails itself to numerous valuable applications relating to the monitoring of gene expression. Some of these applications are described herein. Other applications will be apparent to those of ordinary skill.

a. Characterization of Cell Type

By detecting and optionally quantifying which activated transcription factors are present in a cell sample, the methods of the present invention allow one to identify which genes are being expressed and to what extent each gene is being expressed. Different types of cells for a particular organism will express different genes. As a result, the present invention allows one to rapidly characterize a cell type based on which activated transcription factors are present and at what levels.

One embodiment of this application of the present invention thus relates to a method for characterizing a cell type, the method comprising forming transcription factor probe-activated transcription factors complexes using a test sample and a library of transcription factor probes comprising recognition sequences characteristic of different types of cells; isolating the transcription factor probes from the library which formed complexes involving transcription factors from the test sample; and detecting the isolated transcription factor probes using a hybridization array comprising sequences complementary to the transcription factor probes in the library.

A further embodiment of this application of the present invention relates to a library of transcription factor probes and hybridization array comprising complements to the library of transcription factor probes are provided where the transcription factor probes comprise recognition sequences from multiple different cell types. A kit is also provided that comprises both the library of probes and the hybridization array. The kit may also include instructions for isolating the transcription factor probe-activated transcription factor complexes using an agarose gel, either in combination with the library, the hybridization array, or both.

It is noted that different organisms will also express different activated transcription factors. Characterizing the mixture of different activated transcription factors expressed by a particular organism (e.g., a culture of bacteria) can be used to identify the particular organism. This application of the method of the present invention may be particularly useful for rapidly characterizing microbes such as bacteria and diseased tissue.

One embodiment of this application of the present invention thus relates to a method for characterizing an organism, the method comprising forming transcription factor probe-activated transcription factors complexes using a test sample and a library of transcription factor probes comprising recognition sequences characteristic of different organisms; isolating the transcription factor probes from the library which formed complexes involving transcription factors from the test sample; and detecting the isolated transcription factor probes using a hybridization array comprising sequences complementary to the transcription factor probes in the library.

A further embodiment of this application of the present invention relates to a library of transcription factor probes and hybridization array comprising complements to the library of transcription factor probes are provided where the transcription factor probes comprise recognition sequences from multiple different organisms. A kit is also provided that comprises both the library of probes and the hybridization array. The kit may also include instructions for isolating the transcription factor probe-activated transcription factor complexes using an agarose gel, either in combination with the library, the hybridization array, or both.

It is noted that the mixture of different activated transcription factors expressed by different cell types or organisms may be used according to the present invention as a form of an expression signature for that cell type. FIG. 2 illustrates an array detection format. The pattern formed by the detectable markers [cubes] in FIG. 2 can be used as a visual fingerprint of the expression signature and can be used to identify a particular cell type or organism based on that visual fingerprint. In this regard, it is envisioned that an array may be developed with a great multiplicity of immobilizing agents for different transcription factor probes. It is noted that the number of cubes shown in the figure is employed to reflect signal intensity.

The array may include immobilizing agents for transcription factor probes for different cell types and/or for different organisms. By comparing the array pattern to a standard for a particular cell type or organism, the cell type or organism can be rapidly determined.

b. Determining the Functions of Different Genes

Despite the fact that each cell in the human body contains the same set of genes, the human body is comprised of a wide diversity of different cell types that work in concert to form the human body. The wide diversity of cell types present in the human body and other multicellular organisms is due to variations between cells regarding which genes are expressed, the level at which the genes are expressed, and the conditions under which the genes are expressed. The present invention provides the unique ability of rapidly determining which of a great number of genes are expressed by numerous different cell types. By being able to determine which genes are expressed by which cell types, the functions of different genes can be deduced.

c. Diagnosis of Disease States

Certain disease states may be caused and/or characterizable by certain genes being expressed or not expressed as compared to normal cells. Other disease states may result from and/or be characterizable by certain genes being transcribed at different levels as compared to normal cells.

By being able to rapidly monitor the expression levels of multiple different genes, the present invention provides an accurate method for diagnosing certain disease states known to be associated with the expression non-expression, reduced expression, and/or elevated expression of one or more genes. Conversely, by comparing the expression non-expression, reduced expression, and/or elevated expression of one or more genes in normal and abnormal cells, present invention facilitates the association of one or more genes with certain disease states. By understanding that a particular disease state is caused by a different expression (higher or lower) of one or more proteins, it should be possible to remedy the disease state by increasing or decreasing the expression of the one or more proteins, by administering the one or more proteins or, if particular proteins are overexpressed, by inhibiting the one or more proteins.

One embodiment of this application of the present invention thus relates to a method for diagnosing a disease state of a sample of cells, the method comprising forming transcription factor probe-activated transcription factors complexes using the sample of cells and a library of transcription factor probes comprising different transcription factor recognition sequences; isolating the transcription factor probes from the library which form complexes involving transcription factors from the sample; detecting the isolated transcription factor probes using a hybridization array comprising sequences complementary to the transcription factor probes in the library; and diagnosing a presence of a disease state based on which transcription factors are activated in the cell sample as identified by which transcription factor probes are isolated.

d. Compound Screening for Drug Candidates

Being able to monitor transcription factor activity for multiple different transcription factors at the same time is of great importance to developing a better understanding of different roles that various transcription factors play. In addition, monitoring multiple different transcription factors at the same time allows one to rapidly screen for compounds that influence transcription factor activity, referred to herein as a "transcription factor modulator."

The present invention may thus be used as a high throughput screening assay for transcription factor modulators that either up- or down-regulate genes by influencing the synthesis and activation of transcription factors for those genes.

By having a further understanding of what compounds modulate transcription factor activity, such compounds may be more effectively used for in vitro modification of signal transduction, transcription, splicing, and the like, e.g., as tools for recombinant methods, cell culture modulators, etc. More importantly, such compounds can be used as lead compounds for drug development for a variety of conditions, including as antibacterial, antifungal, antiviral, antineoplastic, inflammation modulatory, or immune system modulatory agents. Accordingly, being able to monitor transcription factor activity for multiple different factors has great use for screening compounds to identify lead compounds for pharmaceutical or other applications.

Indeed, because gene expression is fundamental in all biological processes, including cell division, growth, replication, differentiation, repair, infection of cells, etc., the ability to monitor transcription factor activity and identify compounds which modulator their activity can be used to identify drug leads for a variety of conditions, including neoplasia, inflammation, allergic hypersensitivity, metabolic disease, genetic disease, viral infection, bacterial infection, fungal infection, or the like. In addition, compounds which specifically target transcription factors in undesired organisms such as viruses, fungi, agricultural pests, or the like, can serve as fungicides, bactericides, herbicides, insecticides, and the like. Thus, the range of conditions that are related to transcription factor activity includes conditions in humans and other animals, and in plants, e.g., for agricultural applications.

As used herein, the term "transcription factor modulator" refers to any molecule or complex of more than one molecule that affects the regulatory region. The present invention contemplates screens for synthetic small molecule agents, chemical compounds, chemical complexes, and salts thereof as well as screens for natural products, such as plant extracts or materials obtained from fermentation broths. Other molecules that can be identified using, the screens of the invention include proteins and peptide fragments, peptides, nucleic acids and oligonucleotides (particularly triple-helix-forming oligonucleotides), carbohydrates, phospholipids and other lipid derivatives, steroids and steroid derivatives, prostaglandins and related arachadonic acid derivatives, etc.

Existing methods for monitoring gene expression typically monitor down-stream expression processes by measuring mRNA or the resulting gene product. However, why a particular mRNA or protein is expressed at higher or lower levels is not revealed by these methods. This is because a given compound can influence the formation of a transcription factor, influence the activation of the transcription factor, interact with the activated transcription factor, interact with the regulatory element to which the transcription factor binds, or interact with the mRNA that is produced.

By contrast, because the present invention is specific to detecting activated transcription factors, the present invention can be effectively used to screen for drugs that have a mechanism of action directly related to the expression and/or activation of transcription factors.

It should be noted that methods exist for measuring a transcription factor in a sample. However, because such methods detect the protein itself, they are unable to determine whether the transcription factor is activated, i.e., it is capable of binding to a regulatory element. By being able to detect whether multiple different transcription factors are activated, the present invention, when used in combination with an assay for detecting the amount of activated and unactivated transcription factor, allows one to evaluate specifically how a given compound influences the activation of different transcription factors.

The present invention may be used to screen large chemical libraries for modulator activity for multiple different transcription factors. For example, by exposing cells to different members of the chemical libraries, and performing the methods of the present invention, one is able to screen the different members of the library relative to multiple different transcription factors at the same time.

It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Such combinatorial libraries are then screened to identify those library members (particular chemical species or subclasses) that modulate one or more transcription factors. The compounds thus identified can serve as conventional "lead compounds" or can themselves be used as potential or actual therapeutics for the one or more transcription factors whose activities the compounds modulate.

Preparation and screening of combinatorial libraries is well known to those of skill in the art. Such combinatorial libraries include, but are not limited to, peptide libraries (e.g., U.S. Pat. No. 5,010,175, Furka, Int. J. Pept. Prot. Res.

37:487–493 (1991) and Houghton et al., Nature 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909–6913 (1993)), vinylogous polypeptides (Hagihara et al., J. Amer. Chem. Soc. 114:6568 (1992)), nonpeptidal peptidomimetics with .beta.-D-glucose scaffolding (Hirschmann et al., J. Amer. Chem. Soc. 114:9217–9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309–314 (1996) and PCT/US96/10287), carbohydrate libraries (see, e.g., Liang et al., Science, 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are also commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Control reactions may be performed in combination with the libraries. Such optional control reactions are appropriate and increase the reliability of the screening. Accordingly, in a preferred embodiment, the methods of the invention include such a control reaction. The control reaction may be a negative control reaction that measures the transcription factor activity independent of a transcription modulator. The control reaction may also be a positive control reaction that measures transcription factor activity in view of a known transcription modulator.

By being able to screen multiple different transcription factors at the same time, not only is it possible to screen a large number of potential transcription modulators per day, it is also possible to screen any potential transcription modulator relative to a large number of different transcription factors. The ability to screen multiple different transcription factors at the same time thus greatly enhances the high throughput capabilities of this screening assay.

d. Evaluation of Drug Efficacy

Given that certain disease states may be caused by an unusual level of transcription of one or more genes, drugs may be designed to either stimulate or inhibit transcription in order make gene expression of diseased cells approach the gene expression of normal cells. A rapid and effective method for monitoring gene expression is thus highly advantageous for evaluating the effectiveness of a drug's ability to alter the transcription of one or more genes. The effectiveness of a drug being delivered to a site of action as well as the drug's efficacy in vivo can thus be evaluated with the assistance of the methods of the present invention.

Also of great concern when developing new drugs is the side effects which the drugs might have. One approach for screening drug candidates for undesirable side effects would be to employ the present invention to monitor how gene expression is altered in response to the administration of a drug candidate. By understanding how a candidate affects gene expression, candidates likely to have undesirable side affects can be rapidly identified.

Because the biological importance of transcription factors, they are ideal drug targets. Traditional transcription factor screening assays only detect one transcription factor at a time. As a result, existing assays are tremendously inefficient for detecting how a drug effects different gene expression. However, with the assistance of the present invention, it is now possible to screen hundreds and even thousands of transcription factors in a short amount of time in order to monitor how a given drug affects the expression of wide range of genes. The present invention will thus dramatically facilitate the screening process of identifying new drugs, characterizing their mechanism of the action, and screening for adverse side effects based on the drug's impact on expression.

9. Determining Sequence Binding Requirements for Transcription Factors

In general, a further application of the present invention is the rapid and efficient determination of the DNA sequence binding requirements for a given transcription factor. By being able to efficiently isolate DNA probes from multiple DNA probe-transcription factor complexes, the present invention makes it feasible to identify which DNA sequences bind to transcription factors, quantify the amount of each DNA sequence isolated, and use that information to determine different DNA sequence binding requirements for a given transcription factor in a high throughput manner.

As a result of the completion of the human genome project, many new proteins will be discovered. Based on their primary structure, transcription factors for these proteins can be identified. However, the identification of DNA sequences to which these transcription factors will bind is a more difficult problem which the present invention helps to address.

When determining the DNA sequences to which transcription factors bind, there are several different questions that need to be answered. One question relates to the identification of an optimal binding sequence for the transcription factor. Another question relates to the identification of the minimal sequence required for binding. Yet another question which is related to the prior question, relates to the identification of a consensus sequence which is the minimum sequence required for binding. The present invention can be used to facilitate the answering of each of these questions.

The present invention enables one to rapidly determine a set of DNA sequences to which an activated transcription factor will bind and a set of DNA sequences to which an activated transcription factor will not bind. The amount isolated of each member in the set of DNA sequences to which an activated transcription factor binds may also be quantified.

Using this information, the minimum sequence required for the transcription factor to bind may be determined. Varying degrees of consensus sequences among the DNA sequences to which an activated transcription factor binds can also be determined. Meanwhile, by quantifying the amount of isolated DNA, how different base substitutions affect transcription factor binding can also be evaluated. This enables one to determine the sequences to which a given transcription factor binds most tightly.

Figure 4:
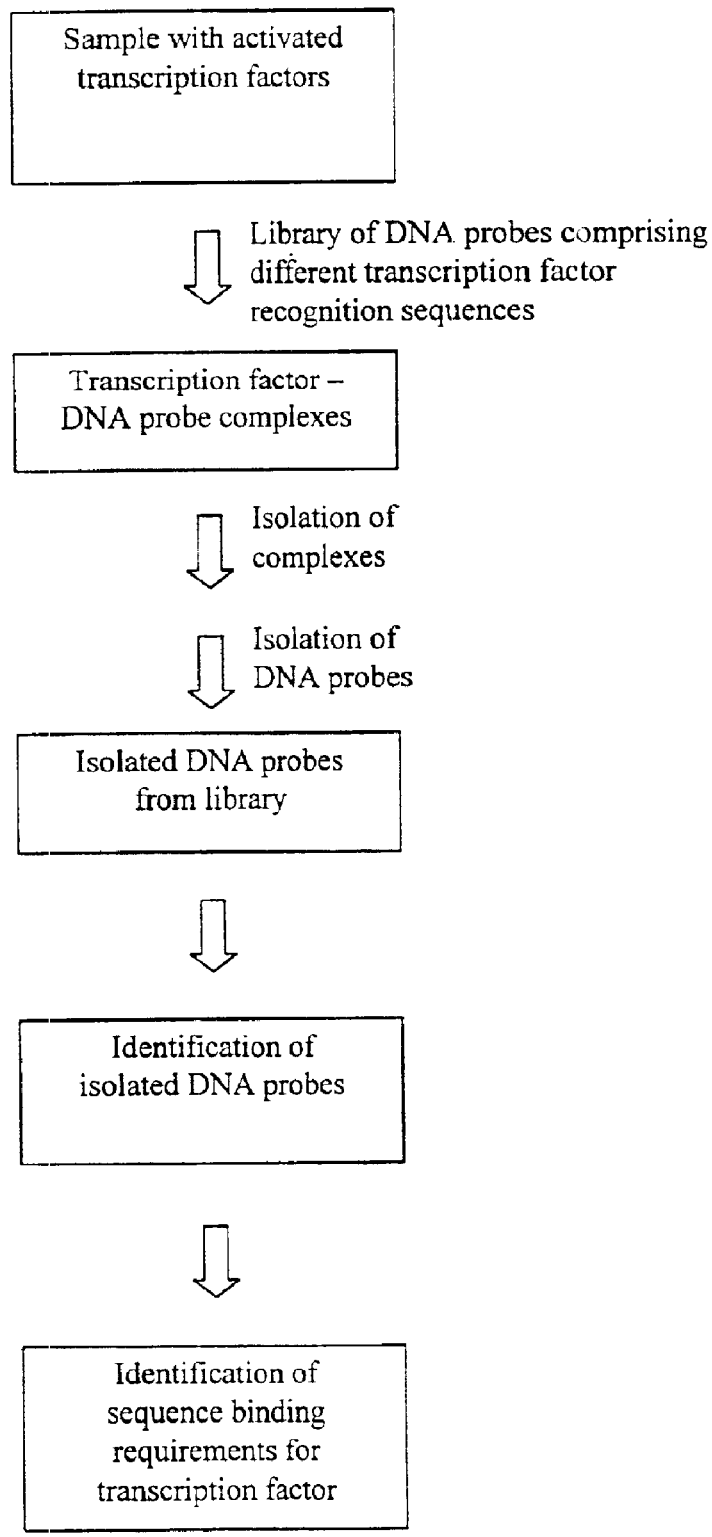
FIG. 4 illustrates a process whereby the minimum DNA sequence binding requirements for a given transcription factor can be rapidly determined.

FIG. 4 illustrates a process whereby the minimum DNA sequence binding requirements for a given transcription factor can be rapidly determined. As illustrated, a sample containing an activated transcription factor is contacted with a library of probes. The probes in the library comprise a DNA sequence and a detectable marker.

Since, in this embodiment, the library of probes are used to determine the minimum DNA sequence binding requirements, the DNA sequences used in the library may be variations on a sequence which the transcription factor is known to bind to. Alternatively, the sequences used in the library may selected without knowledge of the binding specificity of the activated transcription factor.

If the DNA probes used to perform this method are known, a simple hybridization array having complements to the DNA probes in the library may be employed, as described above. However, if a random library of DNA probes is employed, any isolated DNA probes can be characterized by existing position-fixed DNA array technology.

As a result of contacting the sample with the library of probes, complexes are formed between the activated transcription factor present in the sample and DNA probes in the library which have sequences that satisfy the sequence specificity of the DNA-binding domain of the activated transcription factor. The resulting probe-transcription factor complexes are preferably isolated by purification from agarose gel as described previously. After isolating the DNA probe-activated transcription factor complexes, those probes from the library which bind to transcription factors in the sample may be further isolated and characterized as discussed previously.

Since only those probes from the library which form a complex with an activated transcription factor will be isolated, identification of which probes are isolated serves to identify the range of sequences to which the activated transcription factor is capable of binding.

By constructing a consensus sequence based on the isolated probes, one is able to more precisely define the minimum binding requirements for the transcription factor. Furthermore, once a consensus sequence and a series of binding sequences are known, this information can be used to locate the occurrence of those sequences in 5' untranslation regions within a genome. This will allow researchers to identify which proteins may be regulated by the transcription factor. Genomes of different organisms may also be researched to identify proteins that may be functionally related.

Depending on the level of diversity of the library used, a further round of screening may be used to map the binding requirements of the transcription factor in greater detail. For example, when one or more binding sequences are identified, further experimentation may also be conducted to identify more binding sequences. This may involve creating a library of random mutations based on one or more DNA sequences shown to bind to the transcription factor in the prior screen. Binding of the mutants may be performed in order to identify other mutants to which the transcription factor binds. Multiple cycles of generating and screening mutant libraries may be conducted as is necessary and desirable.

Figure 5:
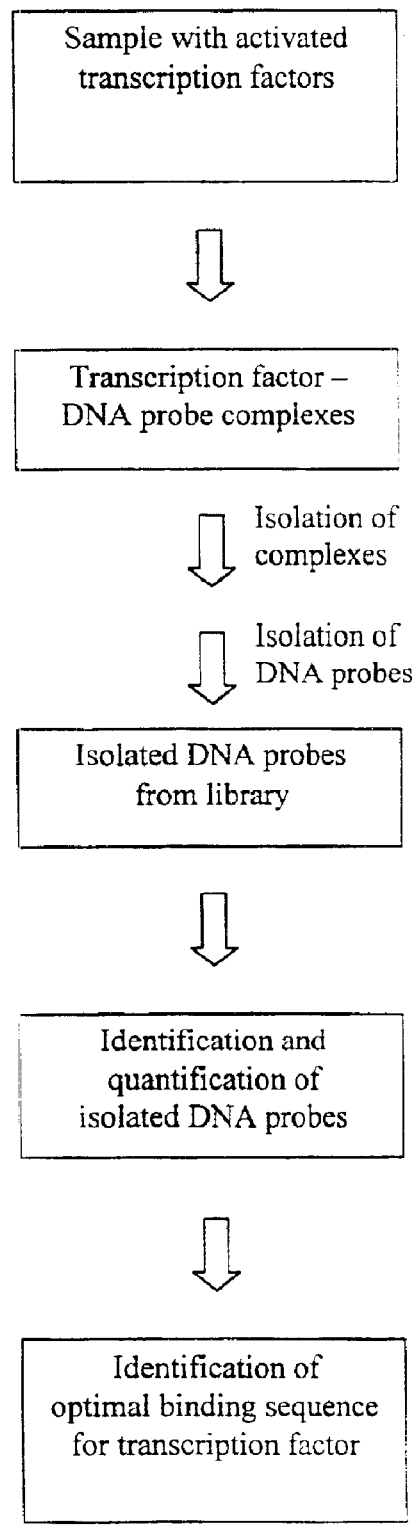
FIG. 5 illustrates a variation of the method described in regard to FIG. 4 where an optimal sequence for binding is identified.

FIG. 5 illustrates a variation of the method described in regard to FIG. 4 where an optimal sequence for binding is identified. As illustrated in FIG. 5, the isolated DNA probes are quantified as well as identified. By monitoring how changes in the sequence affect the amount of each probe isolated, one is able to see how the different sequences compete for binding to the transcription factor. As a result, an optimal transcription factor binding sequence can be identified.

Depending on the level of diversity of the library used to perform the first screen, when one or more binding sequences are identified, further experimentation may also be conducted to identify a better binding sequence. This may involve creating a library of random mutations based on one or more DNA sequences shown to bind to the transcription factor in the prior screen. Quanitification of the binding of the mutants may be performed in order to identify a stronger binding mutant. Multiple cycles of generating and screening mutant libraries may be conducted as is necessary and desirable.

10. Determining Transcription Factor Expression and Activation

Prior to being activated, a transcription factor must be expressed. However, not all expressed transcription factors are activated. By determining whether multiple different transcription factors are being activated according to the present invention, in combination with determining whether the different transcription factors are being expressed, the present invention provides a rapid and efficient method for monitoring how different transcription factor expression and transcription factor activation change.

One application of this method relates to the diagnosis of disease states. By being able to track both changes in transcription factor expression and activation, more precise diagnosis of the cause of genetically related diseases may be discovered.

A further application of this method relates to the evaluation of how different agents or conditions affect both transcription factor expression and activation. For example, different agents can be screened for their ability to inhibit and/or activate the expression of certain proteins or impact different disease states. By knowing how the agent affects both transcription factor expression and activation, one is able to identify the mode of action of the agent. By being able to screen multiple transcription factors at the same time, one is further able to screen those agents for otherwise unforeseen adverse affects on the genetic level.

11. Kits for Use in the Present Invention

A wide variety of kits may be designed for use with the present invention. Various examples of these kits have already been described and additional kits are further described herein.

In one particular embodiment, a kit is provided which includes a library of transcription factor probes comprising recognition sequences for transcription factors. The kit further includes an array of hybridization probes where each probe comprises a sequence that is complementary to at least a portion of the recognition sequences on the probes in the library. In a preferred embodiment, the probes in the array of hybridization probes comprise 2, 3, 4, or more copies of a sequence that is complementary to at least a portion of the recognition sequences on the probes in the library.

In another particular embodiment, a kit is provided which includes a first library of transcription factor probes comprising recognition sequences for transcription factors, each probe in the first library further comprising a first detectable marker. The kit further includes a second library of transcription factor probes comprising the same recognition sequences for transcription factors as the first library, each probe in the second library further comprising a second detectable marker that is different than the first detectable marker.

In another particular embodiment, a kit is provided which includes a library of transcription factor probes comprising recognition sequences for transcription factors in combination with instructions for using agarose gel to isolate transcription factor probe-transcription factor complexes.

In yet another embodiment, a kit is provided which includes an array of hybridization probes where each probe comprises a sequence that is complementary to at least a portion of recognition sequences of transcription factors. The kit further includes instructions for using agarose gel to isolate transcription factor probe-transcription factor complexes.

In yet another embodiment, a kit is provided which includes a hybridization array according to the present invention, hybridization buffer, detection wash buffer, and detection equilibrate buffer.

With regard to any of the kit embodiments, it is noted that the libraries of transcription factor probes and hybridization arrays may be varied as has been described herein.

12. Array Detection of Different Activated Transcription Factors

This section describes experimental results achieved by employing a library of probes according to the present invention to simultaneously screen samples of cells for 54 different activated transcription factors.

FIG. 6 provides the sequences for the probes used to form the transcription factor probe library used in this experiment and the experiments described in Sections 13–19 herein. It is noted that the probes used were doubled stranded, FIG. 6 only showing the strand with biotin labeled at the 5' end. The strands not shown are the complements to the sequences shown in FIG. 6.

FIG. 6 also shows the hybridization probes used in the hybridization probe array used in this experiment. FIG. 7 shows the layout of the array of hybridization probes employed in the experiments described herein.

As can be seen in FIG. 7, each hybridization probe was placed in multiple different regions, in this case, 4 separate regions. It is noted that 2, 3, 4 or more multiple separate regions may be employed. Alternatively, only a single region may also be employed. As can also be seen in FIG. 7, the concentration of hybridization probe was varied in the different regions. This serves both as an internal control as well as a mechanism for quantifying the amount of immobilized probes.

Biotinylated oligonucleotides which are used as controls were positioned in the regions of Row O and Column 17. These oligonucleotides also serve as a legend for the array, allowing a person to identify positions of rows and columns in the array.

The transcription factor probe library described in FIG. 6 was contacted with the array of hybridization probes described in regard to FIGS. 6 and 7. In this instance, unlike the experiments to be described herein, no intermediate isolation of transcription factor probe-transcription factor complexes was performed.

Figure 8:
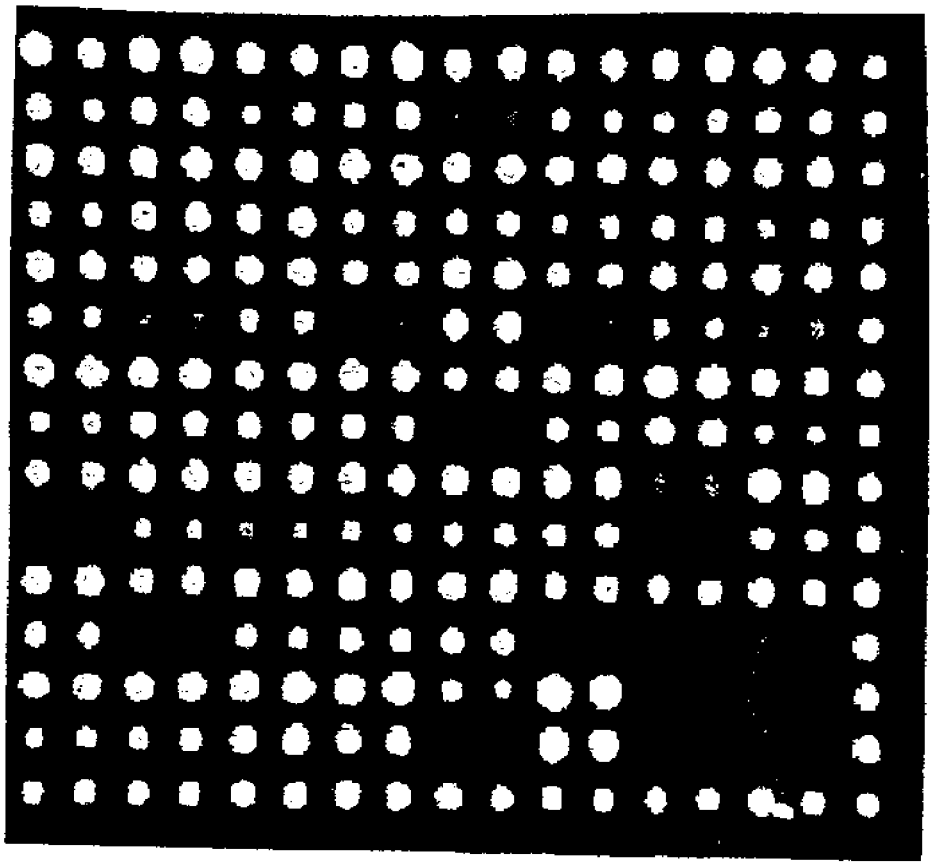
FIG. 8 is an image of the array described in regard to FIG. 7 when the transcription factor probe library described in FIG. 6 is contacted with the array.

FIG. 8 is an image of the resulting array. As can be seen, all of the regions contain immobilized transcription factor probes. As can also be seen, the regions with higher concentrations of the same hybridization probe appear brighter (e.g., A1 and A2 vs. B1 and B2).

13. Array Detection of Selected Activated Transcription Factors

Specific transcription factor probes and combinations of transcription factor probes were also contacted with a nuclear extract from HeLa cells and probes from any transcription factor probe-transcription factor complexes that formed being isolated. The transcription factor probes and combinations of transcription factor probes used were Brn3, c-Myb, Smad3/4 individually and the combination of Brn3, c-Myb, and Smad3/4.

Figure 9A:
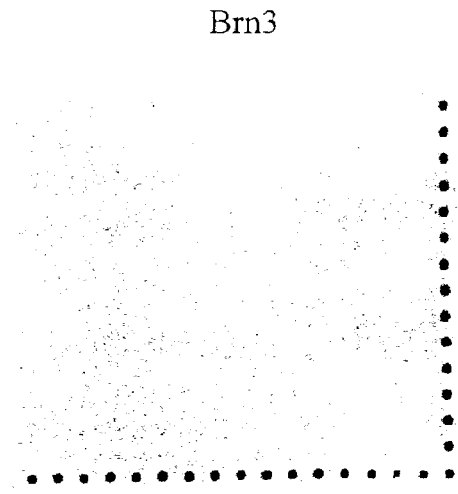
FIG. 9A is an image of an array described in regard to FIG. 7 that is contacted with transcription factor hybridization probes isolated from transcription factor probe-transcription factor complexes formed when Brn3 transcription factor hybridization probes are contacted with a nuclear extract of HeLa cells.
Figure 9B:
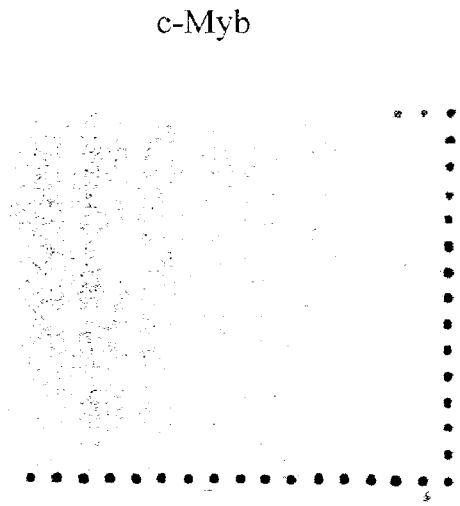
FIG. 9B is an image of an array described in regard to FIG. 7 that is contacted with transcription factor hybridization probes isolated from transcription factor probe-transcription factor complexes formed when c-Myb transcription factor hybridization probes are contacted with a nuclear extract of HeLa cells.
Figure 9C:
FIG. 9C is an image of an array described in regard to FIG. 7 that is contacted with transcription factor hybridization probes isolated from transcription factor probe-transcription factor complexes formed when Smad3/4 transcription factor hybridization probes are contacted with a nuclear extract of HeLa cells.
Figure 9D:
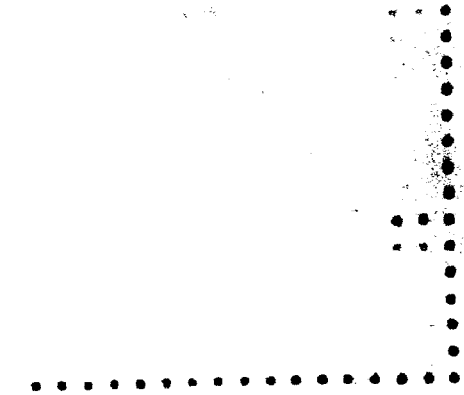
FIG. 9D is an image of an array described in regard to FIG. 7 that is contacted with transcription factor hybridization probes isolated from transcription factor probe-transcription factor complexes formed when Brn3, c-Myb, and Smad3/4 transcription factor hybridization probes are contacted with a nuclear extract of HeLa cells.

FIGS. 9A–9D are images of the resulting arrays. As can be seen, only the hybridization probe regions for Brn3, c-Myb, and Smad3/4 appear to possess immobilized transcription factor probes in FIGS. 9A–9C respectively. Meanwhile, FIG. 9D shows immobilized transcription factor probes in the Brn3, c-Myb, and Smad3/4 hybridization probe regions. The ratios of the spot densities among Brn3, c-Myb, and Smad3/4 has been found to be very similar to what is observed in arrays with single probe detection.

As can also be seen, the higher concentration regions appear consistently darker than the lower concentration regions. The use of regions with different concentrations of hybridization probes allows different concentrations of transcription factor probes to be isolated. If the higher concentration region is saturated, the lower concentration one can be used for evaluation.

14. Array Detection of Activated Transcription Factors in HeLa Cells

The entire library of probes described in regard to FIG. 6 was also contacted with a nuclear extract from HeLa cells and probes from any transcription factor probe-transcription factor complexes that formed being isolated.

Figure 10A:
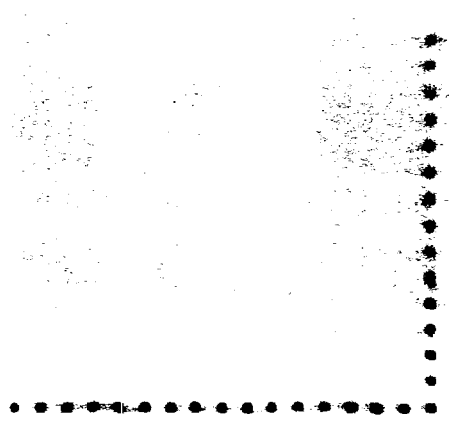
FIG. 10A is an image of an array described in regard to FIG. 7 that is contacted with transcription factor hybridization probes isolated from transcription factor probe-transcription factor complexes formed when the entire library of transcription factor probes described in regard to FIG. 6 are contacted with a control sample that does not contain any transcription factors.
Figure 10B:
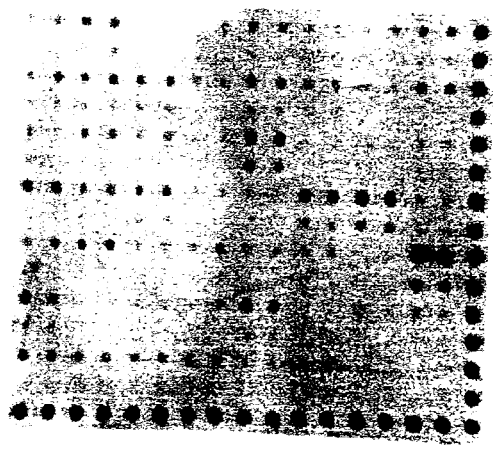
FIG. 10B is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of HeLa cells.

FIG. 10B is an image of the resulting array. As a control, the entire library of probes described in regard to FIG. 6 was also contacted with a control sample that did not contain any transcription factors. Probes from any transcription factor probe-transcription factor complexes that formed were isolated. Since no transcription factors are present in the control sample, it is expected that no complexes are formed and hence no probes are isolated. FIG. 10A is an image of the resulting array.

As can be seen in FIG. 10A and as would be expected, no transcription factor probes are immobilized in the array for the control sample. Meanwhile, as can be seen in FIG. 10B, a myriad of transcription factor probes are immobilized in the array for the HeLa cell sample.

15. Comparison Between Activated Transcription Factors in HeLa Cells and PMA-activated HeLa Cells FIG. 11A is an image of the array resulting from the entire library of probes described in regard to FIG. 6 being contacted with a nuclear extract from HeLa cells and any probes from any transcription factor probe-transcription factor complexes that formed being isolated.

Figure 11A:
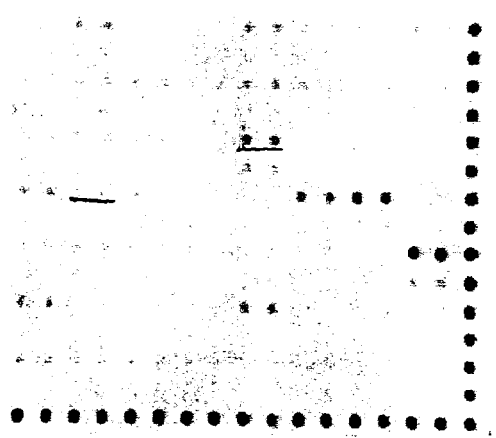
FIG. 11A is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of HeLa cells.
Figure 11B:
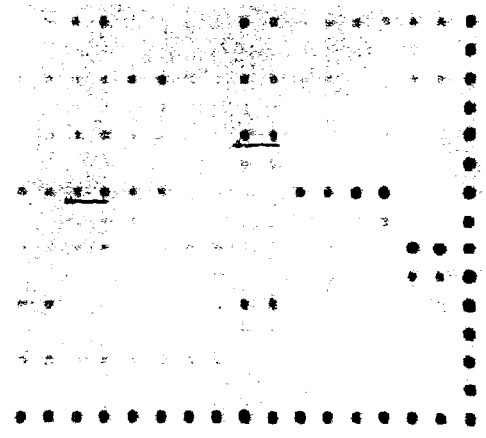
FIG. 11B is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of PMA-treated HeLa cells.

In comparison, FIG. 11B is an image of the array resulting from the entire library of probes described in regard to FIG. 6 being contacted with a nuclear extract from PMA-treated HeLa cells and probes from any transcription factor probe-transcription factor complexes that formed being isolated.

As can be seen by comparing FIGS. 11A and 11B, a number of transcription factors including Ets and NF-E1 can be seen to have been activated at higher levels in the PMA-treated HeLa cells.

The arrays shown in FIGS. 11A and 11B were imaged using a FluorChem imager (from Alpha Innotech Corp) in order to quantify the intensity of the spots appearing in the different regions of the array. FIGS. 12A and 12B provide tables of the signal intensity for the arrays shown in FIGS. 11A and 11B. FIG. 12C provides the ratio between the intensities shown in FIGS. 12A and 12B.

As can be seen by comparing the data shown in FIGS. 12A and 12B, the signal intensities for the regions associated with transcription factors Egr (C5, C6, D5, D6); Ets (E9, E10, F9, F10); NF-E1 (G4, G5, H4, H5); and Smad3/4 (I15, I16, J15, J16) are more intense. Meanwhile, Ets (E9, E10, F9, F10) and Smad3/4 (I15, I16, J15, J16) show no difference in density.

Figure 13:
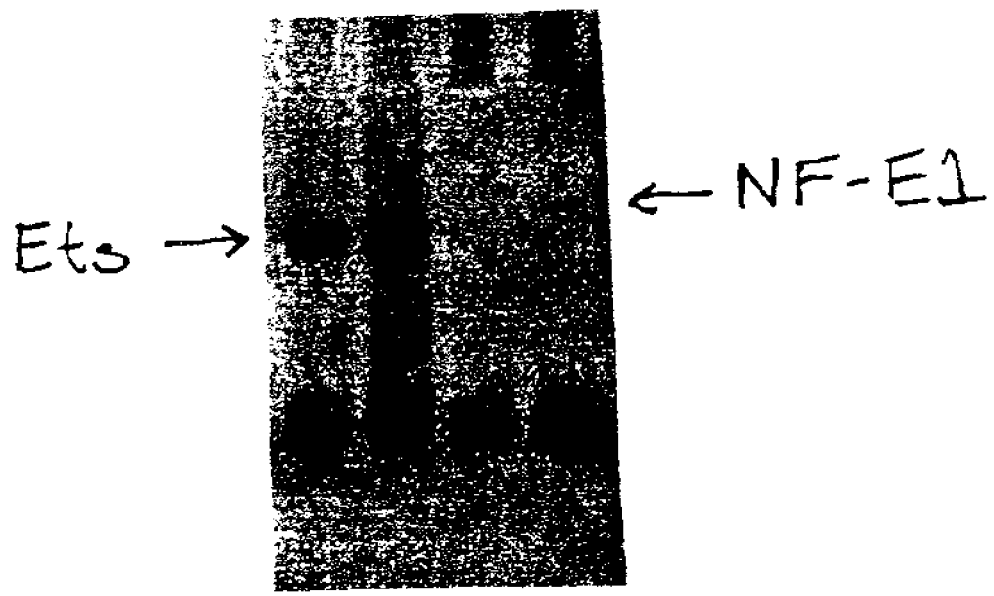
FIG. 13 provides an image of a gel shift analysis of Est and NF-E1 performed on HeLa and PMA-treated HeLa cells.

The results of the experiment described in regard to FIGS. 11A, 11B, and 12A–12C was confirmed by performing a standard gel shift assay using Ets and NF-E1 probes. Specifically, nuclear extracts of HeLa and PMA-treated HeLa cells were incubated with Ets and NF-E1 probes respectively. As can be seen in FIG. 13, bands corresponding to Ets appear for both PMA-treated and untreated HeLa cells. By contrast, a band corresponding to NF-E1 was not present in untreated HeLa cells but appeared in PMA-treated HeLa cells.

16. Comparison Between Activated Transcription Factors in A431 Cells and PMA-Activated A431 Cells The entire library of probes described in regard to FIG. 6 was also contacted with a nuclear extract untreated A431 cells and PMA-treated A431 cells. FIG. 14A is an image of the array for untreated A431 cells and FIG. 14B is an image of the array for PMA-treated A431 cells. As can be seen by comparing FIGS. 14A and 14B, transcription factors NF-E1 and NF-kB were found to be activated by PMA in A431 cells.

Figure 15:
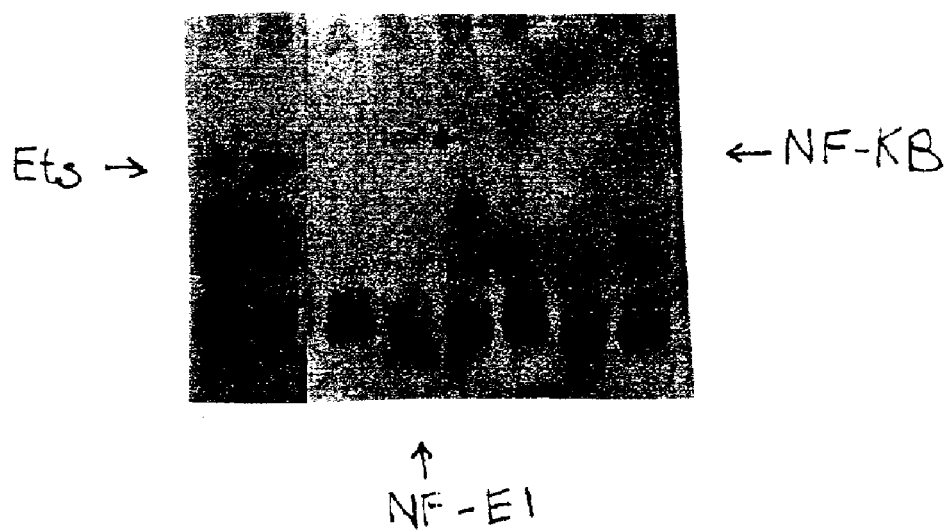
FIG. 15 provides an image of a gel shift analysis of Ets, NF-E1, and NF-kB performed on A431 and PMA-treated A431 cells.
Figure 17A:
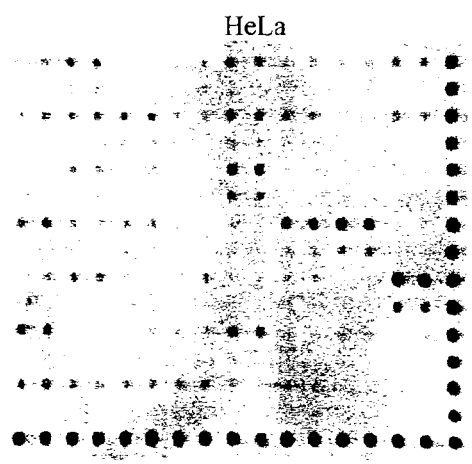
FIG. 17A is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of HeLa cells.
Figure 17B:
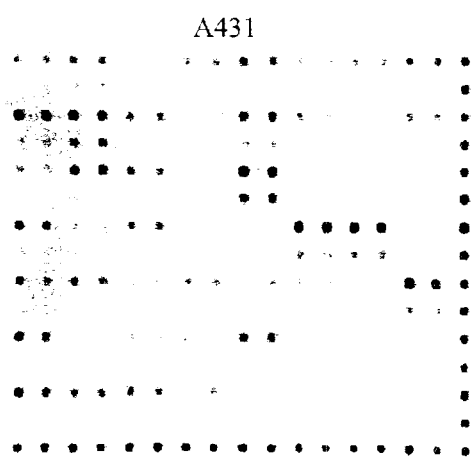
FIG. 17B is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of A431 cells.
Figure 17C:
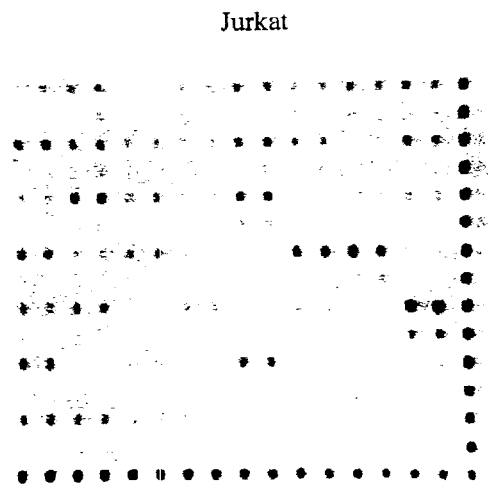
FIG. 17C is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of Jurkat cells.
Figure 17D:
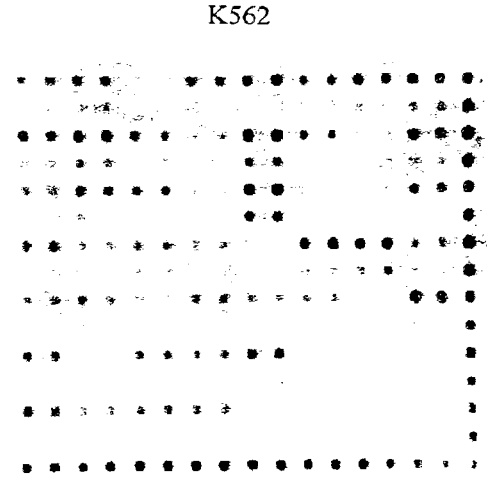
FIG. 17D is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of K-562 cells.
Figure 17E:
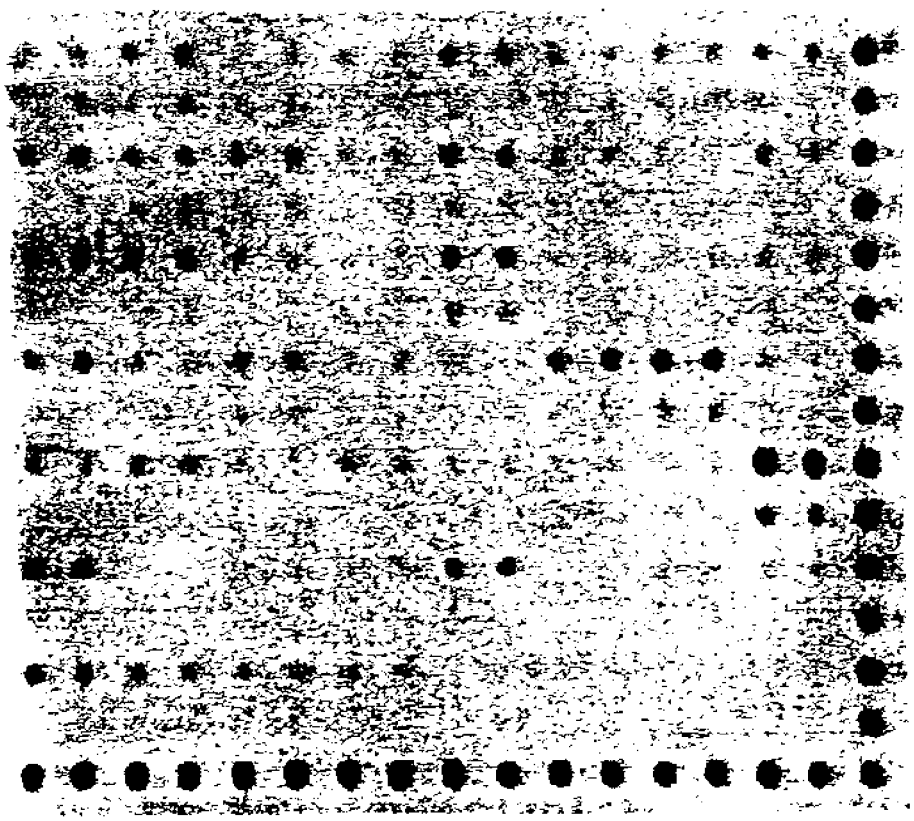
FIG. 17E is an image of an array described in regard to FIG. 7 that is contacted with transcription factor hybridization probes isolated from transcription factor probe-transcription factor complexes formed when the entire library of transcription factor probes described in regard to FIG. 6 are contacted with a nuclear extract of Y79 cells.

The results of the experiment described in regard to FIGS. 14A and 14B was confirmed by performing a standard gel shift assay using Ets, NF-E1, and NF-kB probes. Specifically, nuclear extracts of A431 and PMA-treated A431 cells were incubated with Ets, NF-E1, and NF-kB probes respectively. As can be seen in FIG. 15, bands corresponding to Ets appear for both PMA-treated and untreated A431 cells. By contrast, bands corresponding to NF-E1 and NF-kB were not present in untreated A431 cells but appeared in PMA-treated A431 cells.

17. Comparison Between Activated Transcription Factors in Jurkat Cells and PMA-Activated Jurkat Cells The entire library of probes described in regard to FIG. 6 was also contacted with a nuclear extract untreated Jurkat cells and PMA-treated Jurkat cells. FIG. 16A is an image of the array for untreated Jurkat cells and FIG. 16B is an image of the array for PMA-treated Jurkat cells. As can be seen by comparing FIGS. 16A and 16B, transcription factor AP 1 was found to be activated by PMA. Interestingly, NF-E1 was not induced by PMA, showing that NF-E1 induction by PMA is cell line dependent.

18. Comparison of Activated Transcription Factors Between Multiple Cell Lines

The entire library of probes described in regard to FIG. 6 was also contacted with nuclear extracts for HeLa, A431, Jurkat, K-562, and Y79 cells in order to compare the activated transcription factors present in these different cell lines. FIGS. 17A–17E show the resulting arrays for HeLa, A431, Jurkat, K-562, and Y79 cells respectively. As can be seen, the mixture of transcription factors that are activated varies for the different cells.

19. Gel Shift Analyses of Different Transcription Factors

Figure 18A:
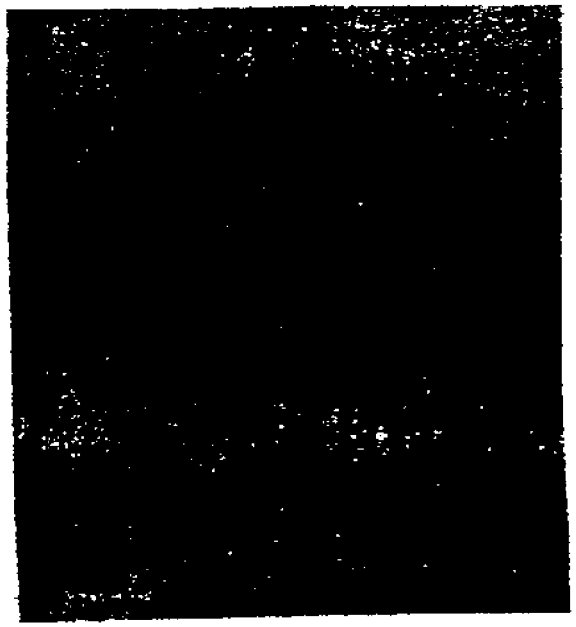
FIG. 18A is an image of a polyacrylamide gel from a gel shift analysis for multiple different transcription factors.
Figure 18B:
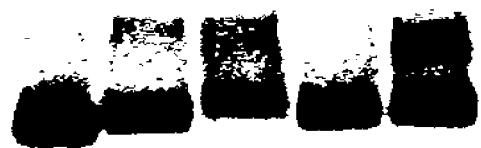
FIG. 18B is an image of an agarose gel from a gel shift analysis for multiple different transcription factors.

Gel shift analyses were performed for multiple different transcription factors in order evaluate the sensitivity of gel shift analysis for detecting different transcription factors. Specifically, a nuclear extract of HeLa cells was incubated with transcription factor probes for c-Myb, Ets, Smad3/4, Brn3 and NF-E2. FIG. 18A is an image of a polyacrylamide gel and FIG. 18B is an image of an agarose gel. As can be seen in both figures, a band corresponding to probe-transcription factor complexes is effectively separated. As can also be seen, c-Myb, Ets, and Smad3/4 can be detected. However, Brn3 and NF-E2 are difficult to detect. By contrast, c-Myb, Ets, Smad3/4, Bm3 and NF-E2 can all be detected in the array shown in FIG. 10B.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method for isolating DNA probes which bind to activated transcription factors in a biological sample, the method comprising:

taking a library of double stranded DNA probes, wherein each DNA probes each comprises a recognition sequence varying within the library, and the variation on the DNA probes in the library is based on its binding to at least two known transcrintion factors selected from the group consisting of AP1, AP-2, ARE, Brn-3, C/EBP, CBF, CDP, c-Myb, CREB, E2F-1, EFR, ERE, Ets, Ets-1/PEA3, FAST-1, GAS/ISRE, GATA, GRE, HNF-4, IRF-1, MEF-1, MEF-2, Myc-Max, NF-1, NFATc, NF-E1, NF-E2, NFKB, Oct-1, p53, Pax-5, Pbx1, Pit 1, PPAR, PRE, RAR, RAR (DR-5), SIE, Smad SBE, Smad3/4, SP1, SRE, Stat1, Stat3, Stat4, Stat4, Stat5, Stat6, TFIID, TR, TR(DR-4), USF-1, VDR (DR-3), HSE, and MRE; contacting a biological sample with the library of double stranded DNA probes under conditions where DNA probe-transcription factor complexes are formed between the DNA probes and activated transcription factors present in the biological sample;

separating DNA probe—transcription factor complexes from non-complexed DNA probes in the library using an agarose gel separation;

excising a portion of the agarose gel comprising the separated DNA probe—transcription factor complexes; and isolating the DNA probes from the excised portion of the agarose gel.

2. A method according to claim 1 wherein one strand of the double stranded DNA probes comprises a detectable marker.

3. A method according to claim 1 wherein one strand of the double stranded DNA probes comprises a detectable marker at a 5' end of the strand.

4. A method according to claim 1 wherein one strand of the double stranded DNA probes comprises biotin at a 5' end of the strand.

5. A method according to claim 1 wherein each of the probes in the library has a recognition sequence greater than 35 base pairs in length.

6. A method according to claim 1 wherein each of the probes in the library has a recognition sequence greater than 40 base pairs in length.

7. A method according to claim 1 wherein the recognition sequence on each of the probes in the library is between 20 and 40 base pairs in length.

8. A method according to claim 1 wherein the recognition sequence on each of the probes in the library is between 25 and 35 base pairs in length.

9. A method according to claim 1 wherein the library comprises at least 2 different DNA recognition sequences.

10. A method according to claim 1 wherein the library comprises at least 5 different DNA recognition sequences.

11. A method according to claim 1 wherein the library comprises DNA recognition sequences for at least 5 different types of cells.

12. A method according to claim 1 wherein the library comprises DNA recognition sequences for malignant, benign, and normal cell types.

13. A method according to claim 1 wherein the biological sample is a nuclear extract.

14. A method according to claim 1, further comprising: identifying which of the DNA probes in the library are isolated.

15. The method according to claim 1, wherein the recognition sequences comprised on the DNA probes are known to bind to at least two transcription factors selected from the group consisting of NF-E1, NFKB, Ets, Ap1, p53 and c-Myb.

* * * * *

SEQUENCE LISTING

<160> NUMBER OF SEQ ID NOS: 162

<210> SEQ ID NO 1
<211> LENGTH: 21
<212> TYPE: DNA
<213> ORGANISM: Artificial sequence
<220> FEATURE:
<223> OTHER INFORMATION: Transcription factor probe PP01

<400> SEQUENCE: 1
cgcttgatga ctcagccgga a                                          21

<210> SEQ ID NO 2
<211> LENGTH: 21
<212> TYPE: DNA
<213> ORGANISM: Artificial sequence
<220> FEATURE:
<223> OTHER INFORMATION: Transcription factor probe PP02

<400> SEQUENCE: 2
ttccggctga gtcatcaagc g                                          21

<210> SEQ ID NO 3

```
<211> LENGTH: 26
<212> TYPE: DNA
<213> ORGANISM: Artificial sequence
<220> FEATURE:
<223> OTHER INFORMATION: Transcription factor probe PP03

<400> SEQUENCE: 3
gatcgaactg accgcccgcg gcccgt                                              26

<210> SEQ ID NO 4
<211> LENGTH: 26
<212> TYPE: DNA
<213> ORGANISM: Artificial sequence
<220> FEATURE:
<223> OTHER INFORMATION: Transcription factor probe PP04

<400> SEQUENCE: 4
acgggccgcg ggcggtcagt tcgatc                                              26

<210> SEQ ID NO 5
<211> LENGTH: 23
<212> TYPE: DNA
<213> ORGANISM: Artificial sequence
<220> FEATURE:
<223> OTHER INFORMATION: Transcription factor probe PP05

<400> SEQUENCE: 5
gtctggtaca gggtgttctt ttt                                                 23

<210> SEQ ID NO 6
<211> LENGTH: 23
<212> TYPE: DNA
<213> ORGANISM: Artificial sequence
<220> FEATURE:
<223> OTHER INFORMATION: Transcription factor probe PP06

<400> SEQUENCE: 6
aaaaagaaca ccctgtacca gac                                                 23

<210> SEQ ID NO 7
<211> LENGTH: 18
<212> TYPE: DNA
<213> ORGANISM: Artificial sequence
<220> FEATURE:
<223> OTHER INFORMATION: Transcription factor probe PP07

<400> SEQUENCE: 7
cacagctcat taacgcgc                                                       18

<210> SEQ ID NO 8
<211> LENGTH: 18
<212> TYPE: DNA
<213> ORGANISM: Artificial sequence
<220> FEATURE:
<223> OTHER INFORMATION: Transcription factor probe PP08

<400> SEQUENCE: 8
gcgcgttaat gagctgtg                                                       18

<210> SEQ ID NO 9
<211> LENGTH: 20
<212> TYPE: DNA
<213> ORGANISM: Artificial sequence
<220> FEATURE:
<223> OTHER INFORMATION: Transcription factor probe PP09

<400> SEQUENCE: 9
```
tgcagattgc gcaatctgca                    20

<210> SEQ ID NO 10
<211> LENGTH: 20
<212> TYPE: DNA
<213> ORGANISM: Artificial sequence
<220> FEATURE:
<223> OTHER INFORMATION: Transcription factor probe PP10

<400> SEQUENCE: 10
tgcagattgc gcaatctgca                    20

<210> SEQ ID NO 11
<211> LENGTH: 27
<212> TYPE: DNA
<213> ORGANISM: Artificial sequence
<220> FEATURE:
<223> OTHER INFORMATION: Transcription factor probe PP11

<400> SEQUENCE: 11
agaccgtacg tgattggtta atctctt             27

<210> SEQ ID NO 12
<211> LENGTH: 27
<212> TYPE: DNA
<213> ORGANISM: Artificial sequence
<220> FEATURE:
<223> OTHER INFORMATION: Transcription factor probe PP12

<400> SEQUENCE: 12
aagagattaa ccaatcacgt acggtct             27

<210> SEQ ID NO 13
<211> LENGTH: 27
<212> TYPE: DNA
<213> ORGANISM: Artificial sequence
<220> FEATURE:
<223> OTHER INFORMATION: Transcription factor probe PP13

<400> SEQUENCE: 13
acccaatgat tattagccaa tttctga             27

<210> SEQ ID NO 14
<211> LENGTH: 27
<212> TYPE: DNA
<213> ORGANISM: Artificial sequence
<220> FEATURE:
<223> OTHER INFORMATION: Transcription factor probe PP14

<400> SEQUENCE: 14
tcagaaattg gctaataatc attgggt             27

<210> SEQ ID NO 15
<211> LENGTH: 25
<212> TYPE: DNA
<213> ORGANISM: Artificial sequence
<220> FEATURE:
<223> OTHER INFORMATION: Transcription factor probe PP15

<400> SEQUENCE: 15
tacaggcata acggttccgt agtga               25

<210> SEQ ID NO 16
<211> LENGTH: 25
<212> TYPE: DNA

```
<213> ORGANISM: Artificial sequence
<220> FEATURE:
<223> OTHER INFORMATION: Transcription factor probe PP16

<400> SEQUENCE: 16
tcactacgga accgttatgc ctgta                                    25

<210> SEQ ID NO 17
<211> LENGTH: 27
<212> TYPE: DNA
<213> ORGANISM: Artificial sequence
<220> FEATURE:
<223> OTHER INFORMATION: Transcription factor probe PP17

<400> SEQUENCE: 17
agagattgcc tgacgtcaga gagctag                                  27

<210> SEQ ID NO 18
<211> LENGTH: 27
<212> TYPE: DNA
<213> ORGANISM: Artificial sequence
<220> FEATURE:
<223> OTHER INFORMATION: Transcription factor probe PP18

<400> SEQUENCE: 18
ctagctctct gacgtcaggc aatctct                                  27

<210> SEQ ID NO 19
<211> LENGTH: 25
<212> TYPE: DNA
<213> ORGANISM: Artificial sequence
<220> FEATURE:
<223> OTHER INFORMATION: Transcription factor probe PP19

<400> SEQUENCE: 19
atttaagttt cgcgcccttt ctcaa                                    25

<210> SEQ ID NO 20
<211> LENGTH: 25
<212> TYPE: DNA
<213> ORGANISM: Artificial sequence
<220> FEATURE:
<223> OTHER INFORMATION: Transcription factor probe PP20

<400> SEQUENCE: 20
ttgagaaagg gcgcgaaact taaat                                    25

<210> SEQ ID NO 21
<211> LENGTH: 27
<212> TYPE: DNA
<213> ORGANISM: Artificial sequence
<220> FEATURE:
<223> OTHER INFORMATION: Transcription factor probe PP21

<400> SEQUENCE: 21
ggatccagcg ggggcgagcg ggggcca                                  27

<210> SEQ ID NO 22
<211> LENGTH: 27
<212> TYPE: DNA
<213> ORGANISM: Artificial sequence
<220> FEATURE:
<223> OTHER INFORMATION: Transcription factor probe PP22

<400> SEQUENCE: 22 tggccccgc tcgcccccgc tggatcc                                   27
```

<210> SEQ ID NO 23
<211> LENGTH: 35
<212> TYPE: DNA
<213> ORGANISM: Artificial sequence
<220> FEATURE:
<223> OTHER INFORMATION: Transcription factor probe PP23

<400> SEQUENCE: 23
gtccaaagtc aggtcacagt gacctgatca aagtt                                35

<210> SEQ ID NO 24
<211> LENGTH: 35
<212> TYPE: DNA
<213> ORGANISM: Artificial sequence
<220> FEATURE:
<223> OTHER INFORMATION: Transcription factor probe PP24

<400> SEQUENCE: 24
aactttgatc aggtcactgt gacctgactt tggac                                35

<210> SEQ ID NO 25
<211> LENGTH: 31
<212> TYPE: DNA
<213> ORGANISM: Artificial sequence
<220> FEATURE:
<223> OTHER INFORMATION: Transcription factor probe PP25

<400> SEQUENCE: 25
ggaggagggc tgcttgagga agtataagaa t                                    31

<210> SEQ ID NO 26
<211> LENGTH: 31
<212> TYPE: DNA
<213> ORGANISM: Artificial sequence
<220> FEATURE:
<223> OTHER INFORMATION: Transcription factor probe PP26

<400> SEQUENCE: 26
attcttatac ttcctcaagc agccctcctc c                                    31

<210> SEQ ID NO 27
<211> LENGTH: 21
<212> TYPE: DNA
<213> ORGANISM: Artificial sequence
<220> FEATURE:
<223> OTHER INFORMATION: Transcription factor probe PP27

<400> SEQUENCE: 27
gatctcgagc aggaagttcg a                                               21

<210> SEQ ID NO 28
<211> LENGTH: 21
<212> TYPE: DNA
<213> ORGANISM: Artificial sequence
<220> FEATURE:
<223> OTHER INFORMATION: Transcription factor probe PP28

<400> SEQUENCE: 28
tcgaacttcc tgctcgagat c                                               21

<210> SEQ ID NO 29
<211> LENGTH: 21
<212> TYPE: DNA
<213> ORGANISM: Artificial sequence
<220> FEATURE:

```
<223> OTHER INFORMATION: Transcription factor probe PP29

<400> SEQUENCE: 29
cggattgtgt attggctgta c                                              21

<210> SEQ ID NO 30
<211> LENGTH: 21
<212> TYPE: DNA
<213> ORGANISM: Artificial sequence
<220> FEATURE:
<223> OTHER INFORMATION: Transcription factor probe PP30

<400> SEQUENCE: 30
gtacagccaa tacacaatcc g                                              21

<210> SEQ ID NO 31
<211> LENGTH: 32
<212> TYPE: DNA
<213> ORGANISM: Artificial sequence
<220> FEATURE:
<223> OTHER INFORMATION: Transcription factor probe PP31

<400> SEQUENCE: 31
cgaagtactt tcagtttcat attactctac aa                                  32

<210> SEQ ID NO 32
<211> LENGTH: 32
<212> TYPE: DNA
<213> ORGANISM: Artificial sequence
<220> FEATURE:
<223> OTHER INFORMATION: Transcription factor probe PP32

<400> SEQUENCE: 32
ttgtagagta atatgaaact gaaagtactt cg                                  32

<210> SEQ ID NO 33
<211> LENGTH: 27
<212> TYPE: DNA
<213> ORGANISM: Artificial sequence
<220> FEATURE:
<223> OTHER INFORMATION: Transcription factor probe PP33

<400> SEQUENCE: 33
cacttgataa cagaaagtga taactct                                        27

<210> SEQ ID NO 34
<211> LENGTH: 27
<212> TYPE: DNA
<213> ORGANISM: Artificial sequence
<220> FEATURE:
<223> OTHER INFORMATION: Transcription factor probe PP34

<400> SEQUENCE: 34
agagttatca ctttctgtta tcaagtg                                        27

<210> SEQ ID NO 35
<211> LENGTH: 41
<212> TYPE: DNA
<213> ORGANISM: Artificial sequence
<220> FEATURE:
<223> OTHER INFORMATION: Transcription factor probe PP35

<400> SEQUENCE: 35
gaccctagag gatctgtaca ggatgttcta gatccaattc g                        41
```

```
<210> SEQ ID NO 36
<211> LENGTH: 41
<212> TYPE: DNA
<213> ORGANISM: Artificial sequence
<220> FEATURE:
<223> OTHER INFORMATION: Transcription factor probe PP36

<400> SEQUENCE: 36
cgaattggat ctagaacatc ctgtacagat cctctagggt c                 41

<210> SEQ ID NO 37
<211> LENGTH: 25
<212> TYPE: DNA
<213> ORGANISM: Artificial sequence
<220> FEATURE:
<223> OTHER INFORMATION: Transcription factor probe PP37

<400> SEQUENCE: 37
ctcagcttgt actttggtac aacta                                   25

<210> SEQ ID NO 38
<211> LENGTH: 25
<212> TYPE: DNA
<213> ORGANISM: Artificial sequence
<220> FEATURE:
<223> OTHER INFORMATION: Transcription factor probe PP38

<400> SEQUENCE: 38
tagttgtacc aaagtacaag ctgag                                   25

<210> SEQ ID NO 39
<211> LENGTH: 22
<212> TYPE: DNA
<213> ORGANISM: Artificial sequence
<220> FEATURE:
<223> OTHER INFORMATION: Transcription factor probe PP39

<400> SEQUENCE: 39
ggaagcgaaa atgaaattga ct                                      22

<210> SEQ ID NO 40
<211> LENGTH: 22
<212> TYPE: DNA
<213> ORGANISM: Artificial sequence
<220> FEATURE:
<223> OTHER INFORMATION: Transcription factor probe PP40

<400> SEQUENCE: 40
agtcaatttc attttcgctt cc                                      22

<210> SEQ ID NO 41
<211> LENGTH: 25
<212> TYPE: DNA
<213> ORGANISM: Artificial sequence
<220> FEATURE:
<223> OTHER INFORMATION: Transcription factor probe PP41

<400> SEQUENCE: 41
gatcccccca acacctgctg cctga                                   25

<210> SEQ ID NO 42
<211> LENGTH: 25
<212> TYPE: DNA
<213> ORGANISM: Artificial sequence
<220> FEATURE:
<223> OTHER INFORMATION: Transcription factor probe PP42
```

<400> SEQUENCE: 42
tcaggcagca ggtgttgggg ggatc            25

<210> SEQ ID NO 43
<211> LENGTH: 25
<212> TYPE: DNA
<213> ORGANISM: Artificial sequence
<220> FEATURE:
<223> OTHER INFORMATION: Transcription factor probe PP43

<400> SEQUENCE: 43
gatcgctcta aaataaccc tgtcg            25

<210> SEQ ID NO 44
<211> LENGTH: 25
<212> TYPE: DNA
<213> ORGANISM: Artificial sequence
<220> FEATURE:
<223> OTHER INFORMATION: Transcription factor probe PP44

<400> SEQUENCE: 44
cgacagggtt atttttagag cgatc            25

<210> SEQ ID NO 45
<211> LENGTH: 26
<212> TYPE: DNA
<213> ORGANISM: Artificial sequence
<220> FEATURE:
<223> OTHER INFORMATION: Transcription factor probe PP45

<400> SEQUENCE: 45
ggaagcagac cacgtggtct gcttcc            26

<210> SEQ ID NO 46
<211> LENGTH: 26
<212> TYPE: DNA
<213> ORGANISM: Artificial sequence
<220> FEATURE:
<223> OTHER INFORMATION: Transcription factor probe PP46

<400> SEQUENCE: 46
ggaagcagac cacgtggtct gcttcc            26

<210> SEQ ID NO 47
<211> LENGTH: 25
<212> TYPE: DNA
<213> ORGANISM: Artificial sequence
<220> FEATURE:
<223> OTHER INFORMATION: Transcription factor probe PP47

<400> SEQUENCE: 47
ttttggattg aagccaatat gataa            25

<210> SEQ ID NO 48
<211> LENGTH: 25
<212> TYPE: DNA
<213> ORGANISM: Artificial sequence
<220> FEATURE:
<223> OTHER INFORMATION: Transcription factor probe PP48

<400> SEQUENCE: 48
ttatcatatt ggcttcaatc caaaa            25

<210> SEQ ID NO 49
<211> LENGTH: 30

```
<212> TYPE: DNA
<213> ORGANISM: Artificial sequence
<220> FEATURE:
<223> OTHER INFORMATION: Transcription factor probe PP49

<400> SEQUENCE: 49
acgcccaaag aggaaaattt gtttcataca                                    30

<210> SEQ ID NO 50
<211> LENGTH: 30
<212> TYPE: DNA
<213> ORGANISM: Artificial sequence
<220> FEATURE:
<223> OTHER INFORMATION: Transcription factor probe PP50

<400> SEQUENCE: 50
tgtatgaaac aaatttteet ctttgggcgt                                    30

<210> SEQ ID NO 51
<211> LENGTH: 27
<212> TYPE: DNA
<213> ORGANISM: Artificial sequence
<220> FEATURE:
<223> OTHER INFORMATION: Transcription factor probe PP51

<400> SEQUENCE: 51
cgctccgcgg ccatcttggc ggctggt                                       27

<210> SEQ ID NO 52
<211> LENGTH: 27
<212> TYPE: DNA
<213> ORGANISM: Artificial sequence
<220> FEATURE:
<223> OTHER INFORMATION: Transcription factor probe PP52

<400> SEQUENCE: 52
accagccgcc aagatggccg cggagcg                                       27

<210> SEQ ID NO 53
<211> LENGTH: 27
<212> TYPE: DNA
<213> ORGANISM: Artificial sequence
<220> FEATURE:
<223> OTHER INFORMATION: Transcription factor probe PP53

<400> SEQUENCE: 53
tggggaacct gtgctgagtc actggag                                       27

<210> SEQ ID NO 54
<211> LENGTH: 27
<212> TYPE: DNA
<213> ORGANISM: Artificial sequence
<220> FEATURE:
<223> OTHER INFORMATION: Transcription factor probe PP54

<400> SEQUENCE: 54
ctccagtgac tcagcacagg ttcccca                                       27

<210> SEQ ID NO 55
<211> LENGTH: 22
<212> TYPE: DNA
<213> ORGANISM: Artificial sequence
<220> FEATURE:
<223> OTHER INFORMATION: Transcription factor probe PP55

<400> SEQUENCE: 55
```

```
agttgagggg actttcccag gc                                          22

<210> SEQ ID NO 56
<211> LENGTH: 22
<212> TYPE: DNA
<213> ORGANISM: Artificial sequence
<220> FEATURE:
<223> OTHER INFORMATION: Transcription factor probe PP56

<400> SEQUENCE: 56
gcctgggaaa gtcccctcaa ct                                          22

<210> SEQ ID NO 57
<211> LENGTH: 22
<212> TYPE: DNA
<213> ORGANISM: Artificial sequence
<220> FEATURE:
<223> OTHER INFORMATION: Transcription factor probe PP57

<400> SEQUENCE: 57
tgtcgaatgc aaatcactag aa                                          22

<210> SEQ ID NO 58
<211> LENGTH: 22
<212> TYPE: DNA
<213> ORGANISM: Artificial sequence
<220> FEATURE:
<223> OTHER INFORMATION: Transcription factor probe PP58

<400> SEQUENCE: 58
ttctagtgat ttccattcga ca                                          22

<210> SEQ ID NO 59
<211> LENGTH: 27
<212> TYPE: DNA
<213> ORGANISM: Artificial sequence
<220> FEATURE:
<223> OTHER INFORMATION: Transcription factor probe PP59

<400> SEQUENCE: 59
tacagaacat gtctaagcat gctgggg                                     27

<210> SEQ ID NO 60
<211> LENGTH: 27
<212> TYPE: DNA
<213> ORGANISM: Artificial sequence
<220> FEATURE:
<223> OTHER INFORMATION: Transcription factor probe PP60

<400> SEQUENCE: 60
ccccagcatg cttagacatg ttctgta                                     27

<210> SEQ ID NO 61
<211> LENGTH: 27
<212> TYPE: DNA
<213> ORGANISM: Artificial sequence
<220> FEATURE:
<223> OTHER INFORMATION: Transcription factor probe PP61

<400> SEQUENCE: 61
gaatggggca ctgaggcgtg accaccg                                     27

<210> SEQ ID NO 62
<211> LENGTH: 27
<212> TYPE: DNA
<213> ORGANISM: Artificial sequence
```

```
<220> FEATURE:
<223> OTHER INFORMATION: Transcription factor probe PP62

<400> SEQUENCE: 62
cggtggtcac gcctcagtgc cccattc                                27

<210> SEQ ID NO 63
<211> LENGTH: 26
<212> TYPE: DNA
<213> ORGANISM: Artificial sequence
<220> FEATURE:
<223> OTHER INFORMATION: Transcription factor probe PP63

<400> SEQUENCE: 63
cgaattgatt gatgcactaa ttggag                                 26

<210> SEQ ID NO 64
<211> LENGTH: 26
<212> TYPE: DNA
<213> ORGANISM: Artificial sequence
<220> FEATURE:
<223> OTHER INFORMATION: Transcription factor probe PP64

<400> SEQUENCE: 64
ctccaattag tgcatcaatc aattcg                                 26

<210> SEQ ID NO 65
<211> LENGTH: 28
<212> TYPE: DNA
<213> ORGANISM: Artificial sequence
<220> FEATURE:
<223> OTHER INFORMATION: Transcription factor probe PP65

<400> SEQUENCE: 65
tgtcttcctg aatatgaata agaaataa                               28

<210> SEQ ID NO 66
<211> LENGTH: 28
<212> TYPE: DNA
<213> ORGANISM: Artificial sequence
<220> FEATURE:
<223> OTHER INFORMATION: Transcription factor probe PP66

<400> SEQUENCE: 66
ttatttctta ttcatattca ggaagaca                               28

<210> SEQ ID NO 67
<211> LENGTH: 20
<212> TYPE: DNA
<213> ORGANISM: Artificial sequence
<220> FEATURE:
<223> OTHER INFORMATION: Transcription factor probe PP67

<400> SEQUENCE: 67
caaaactagg tcaaaggtca                                        20

<210> SEQ ID NO 68
<211> LENGTH: 20
<212> TYPE: DNA
<213> ORGANISM: Artificial sequence
<220> FEATURE:
<223> OTHER INFORMATION: Transcription factor probe PP68

<400> SEQUENCE: 68
tgacctttga cctagttttg                                        20
```

<210> SEQ ID NO 69
<211> LENGTH: 27
<212> TYPE: DNA
<213> ORGANISM: Artificial sequence
<220> FEATURE:
<223> OTHER INFORMATION: Transcription factor probe PP69

<400> SEQUENCE: 69
gatcctgtac aggatgttct agctaca                                    27

<210> SEQ ID NO 70
<211> LENGTH: 27
<212> TYPE: DNA
<213> ORGANISM: Artificial sequence
<220> FEATURE:
<223> OTHER INFORMATION: Transcription factor probe PP70

<400> SEQUENCE: 70
tgtagctaga acatcctgta caggatc                                    27

<210> SEQ ID NO 71
<211> LENGTH: 31
<212> TYPE: DNA
<213> ORGANISM: Artificial sequence
<220> FEATURE:
<223> OTHER INFORMATION: Transcription factor probe PP71

<400> SEQUENCE: 71
tcgagggtag ggttcaccga aagttcactc g                               31

<210> SEQ ID NO 72
<211> LENGTH: 31
<212> TYPE: DNA
<213> ORGANISM: Artificial sequence
<220> FEATURE:
<223> OTHER INFORMATION: Transcription factor probe PP72

<400> SEQUENCE: 72
cgagtgaact ttcggtgaac cctaccctcg a                               31

<210> SEQ ID NO 73
<211> LENGTH: 26
<212> TYPE: DNA
<213> ORGANISM: Artificial sequence
<220> FEATURE:
<223> OTHER INFORMATION: Transcription factor probe PP73

<400> SEQUENCE: 73
agcttcaggt cagaggtcag agagct                                     26

<210> SEQ ID NO 74
<211> LENGTH: 26
<212> TYPE: DNA
<213> ORGANISM: Artificial sequence
<220> FEATURE:
<223> OTHER INFORMATION: Transcription factor probe PP74

<400> SEQUENCE: 74
agctctctga cctctgacct gaagct                                     26

<210> SEQ ID NO 75
<211> LENGTH: 27
<212> TYPE: DNA
<213> ORGANISM: Artificial sequence
<220> FEATURE:
<223> OTHER INFORMATION: Transcription factor probe PP75

```
<400> SEQUENCE: 75
gtgcatttcc cgtaaatctt gtctaca                                27

<210> SEQ ID NO 76
<211> LENGTH: 27
<212> TYPE: DNA
<213> ORGANISM: Artificial sequence
<220> FEATURE:
<223> OTHER INFORMATION: Transcription factor probe PP76

<400> SEQUENCE: 76
tgtagacaag atttacggga aatgcac                                27

<210> SEQ ID NO 77
<211> LENGTH: 16
<212> TYPE: DNA
<213> ORGANISM: Artificial sequence
<220> FEATURE:
<223> OTHER INFORMATION: Transcription factor probe PP77

<400> SEQUENCE: 77
agtatgtcta gactga                                           16

<210> SEQ ID NO 78
<211> LENGTH: 16
<212> TYPE: DNA
<213> ORGANISM: Artificial sequence
<220> FEATURE:
<223> OTHER INFORMATION: Transcription factor probe PP78

<400> SEQUENCE: 78
tcagtctaga catact                                           16

<210> SEQ ID NO 79
<211> LENGTH: 39
<212> TYPE: DNA
<213> ORGANISM: Artificial sequence
<220> FEATURE:
<223> OTHER INFORMATION: Transcription factor probe PP79

<400> SEQUENCE: 79
tcgagagcca gacaaaaagc cagacattta gccagacac                  39

<210> SEQ ID NO 80
<211> LENGTH: 39
<212> TYPE: DNA
<213> ORGANISM: Artificial sequence
<220> FEATURE:
<223> OTHER INFORMATION: Transcription factor probe PP80

<400> SEQUENCE: 80
gtgtctggct aaatgtctgg cttttttgtct ggctctcga                 39

<210> SEQ ID NO 81
<211> LENGTH: 21
<212> TYPE: DNA
<213> ORGANISM: Artificial sequence
<220> FEATURE:
<223> OTHER INFORMATION: Transcription factor probe PP81

<400> SEQUENCE: 81
attcgatcgg ggcggggcga g                                     21

<210> SEQ ID NO 82
```

```
<211> LENGTH: 21
<212> TYPE: DNA
<213> ORGANISM: Artificial sequence
<220> FEATURE:
<223> OTHER INFORMATION: Transcription factor probe PP82

<400> SEQUENCE: 82
ctcgccccgc cccgatcgaa t                                              21

<210> SEQ ID NO 83
<211> LENGTH: 22
<212> TYPE: DNA
<213> ORGANISM: Artificial sequence
<220> FEATURE:
<223> OTHER INFORMATION: Transcription factor probe PP83

<400> SEQUENCE: 83
ggatgtccat attaggacat ct                                             22

<210> SEQ ID NO 84
<211> LENGTH: 22
<212> TYPE: DNA
<213> ORGANISM: Artificial sequence
<220> FEATURE:
<223> OTHER INFORMATION: Transcription factor probe PP84

<400> SEQUENCE: 84
agatgtccta atatggacat cc                                             22

<210> SEQ ID NO 85
<211> LENGTH: 25
<212> TYPE: DNA
<213> ORGANISM: Artificial sequence
<220> FEATURE:
<223> OTHER INFORMATION: Transcription factor probe PP85

<400> SEQUENCE: 85
catgttatgc atattcctgt aagtg                                          25

<210> SEQ ID NO 86
<211> LENGTH: 25
<212> TYPE: DNA
<213> ORGANISM: Artificial sequence
<220> FEATURE:
<223> OTHER INFORMATION: Transcription factor probe PP86

<400> SEQUENCE: 86
cacttacagg aatatgcata acatg                                          25

<210> SEQ ID NO 87
<211> LENGTH: 24
<212> TYPE: DNA
<213> ORGANISM: Artificial sequence
<220> FEATURE:
<223> OTHER INFORMATION: Transcription factor probe PP87

<400> SEQUENCE: 87
gatccttctg ggaattccta gatc                                           24

<210> SEQ ID NO 88
<211> LENGTH: 24
<212> TYPE: DNA
<213> ORGANISM: Artificial sequence
<220> FEATURE:
<223> OTHER INFORMATION: Transcription factor probe PP88

<400> SEQUENCE: 88
```

```
gatctaggaa ttcccagaag gatc                                            24

<210> SEQ ID NO 89
<211> LENGTH: 33
<212> TYPE: DNA
<213> ORGANISM: Artificial sequence
<220> FEATURE:
<223> OTHER INFORMATION: Transcription factor probe PP89

<400> SEQUENCE: 89
ctagagcctg atttccccga aatgatgagc tag                                  33

<210> SEQ ID NO 90
<211> LENGTH: 33
<212> TYPE: DNA
<213> ORGANISM: Artificial sequence
<220> FEATURE:
<223> OTHER INFORMATION: Transcription factor probe PP90

<400> SEQUENCE: 90
ctagctcatc atttcgggga aatcaggctc tag                                  33

<210> SEQ ID NO 91
<211> LENGTH: 21
<212> TYPE: DNA
<213> ORGANISM: Artificial sequence
<220> FEATURE:
<223> OTHER INFORMATION: Transcription factor probe PP91

<400> SEQUENCE: 91
agatttctag gaattcaatc c                                               21

<210> SEQ ID NO 92
<211> LENGTH: 21
<212> TYPE: DNA
<213> ORGANISM: Artificial sequence
<220> FEATURE:
<223> OTHER INFORMATION: Transcription factor probe PP92

<400> SEQUENCE: 92
ggattgaatt cctagaaatc t                                               21

<210> SEQ ID NO 93
<211> LENGTH: 20
<212> TYPE: DNA
<213> ORGANISM: Artificial sequence
<220> FEATURE:
<223> OTHER INFORMATION: Transcription factor probe PP93

<400> SEQUENCE: 93
gtatttccca gaaaaggaac                                                 20

<210> SEQ ID NO 94
<211> LENGTH: 20
<212> TYPE: DNA
<213> ORGANISM: Artificial sequence
<220> FEATURE:
<223> OTHER INFORMATION: Transcription factor probe PP94

<400> SEQUENCE: 94
gttccttttc tgggaaatac                                                 20

<210> SEQ ID NO 95
<211> LENGTH: 25
<212> TYPE: DNA
```

```
<213> ORGANISM: Artificial sequence
<220> FEATURE:
<223> OTHER INFORMATION: Transcription factor probe PP95

<400> SEQUENCE: 95
gcagagcata taaaatgagg tagga                                              25

<210> SEQ ID NO 96
<211> LENGTH: 25
<212> TYPE: DNA
<213> ORGANISM: Artificial sequence
<220> FEATURE:
<223> OTHER INFORMATION: Transcription factor probe PP96

<400> SEQUENCE: 96
tcctacctca ttttatatgc tctgc                                              25

<210> SEQ ID NO 97
<211> LENGTH: 32
<212> TYPE: DNA
<213> ORGANISM: Artificial sequence
<220> FEATURE:
<223> OTHER INFORMATION: Transcription factor probe PP97

<400> SEQUENCE: 97
gatcgtaaga ttcaggtcat gacctgagga ga                                      32

<210> SEQ ID NO 98
<211> LENGTH: 32
<212> TYPE: DNA
<213> ORGANISM: Artificial sequence
<220> FEATURE:
<223> OTHER INFORMATION: Transcription factor probe PP98

<400> SEQUENCE: 98
tctcctcagg tcatgacctg aatcttacga tc                                      32

<210> SEQ ID NO 99
<211> LENGTH: 29
<212> TYPE: DNA
<213> ORGANISM: Artificial sequence
<220> FEATURE:
<223> OTHER INFORMATION: Transcription factor probe PP99

<400> SEQUENCE: 99
agcttcaggt cacaggaggt cagagagct                                          29

<210> SEQ ID NO 100
<211> LENGTH: 29
<212> TYPE: DNA
<213> ORGANISM: Artificial sequence
<220> FEATURE:
<223> OTHER INFORMATION: Transcription factor probe PP100

<400> SEQUENCE: 100
agctctctga cctcctgtga cctgaagct                                          29

<210> SEQ ID NO 101
<211> LENGTH: 23
<212> TYPE: DNA
<213> ORGANISM: Artificial sequence
<220> FEATURE:
<223> OTHER INFORMATION: Transcription factor probe PP101

<400> SEQUENCE: 101
cacccggtca cgtggcctac acc                                                23
```

```
<210> SEQ ID NO 102
<211> LENGTH: 23
<212> TYPE: DNA
<213> ORGANISM: Artificial sequence
<220> FEATURE:
<223> OTHER INFORMATION: Transcription factor probe PP102

<400> SEQUENCE: 102
ggtgtaggcc acgtgaccgg gtg                                              23

<210> SEQ ID NO 103
<211> LENGTH: 28
<212> TYPE: DNA
<213> ORGANISM: Artificial sequence
<220> FEATURE:
<223> OTHER INFORMATION: Transcription factor probe PP103

<400> SEQUENCE: 103
agcttcaggt caaggaggtc agagagct                                         28

<210> SEQ ID NO 104
<211> LENGTH: 28
<212> TYPE: DNA
<213> ORGANISM: Artificial sequence
<220> FEATURE:
<223> OTHER INFORMATION: Transcription factor probe PP104

<400> SEQUENCE: 104
agctctctga cctccttgac ctgaagct                                         28

<210> SEQ ID NO 105
<211> LENGTH: 15
<212> TYPE: DNA
<213> ORGANISM: Artificial sequence
<220> FEATURE:
<223> OTHER INFORMATION: Transcription factor probe PP105

<400> SEQUENCE: 105
ctggaatttt ctaga                                                       15

<210> SEQ ID NO 106
<211> LENGTH: 15
<212> TYPE: DNA
<213> ORGANISM: Artificial sequence
<220> FEATURE:
<223> OTHER INFORMATION: Transcription factor probe PP106

<400> SEQUENCE: 106
tctagaaaat tccag                                                       15

<210> SEQ ID NO 107
<211> LENGTH: 15
<212> TYPE: DNA
<213> ORGANISM: Artificial sequence
<220> FEATURE:
<223> OTHER INFORMATION: Transcription factor probe PP107

<400> SEQUENCE: 107
ctctgcgccc ggccc                                                       15

<210> SEQ ID NO 108
<211> LENGTH: 15
<212> TYPE: DNA
<213> ORGANISM: Artificial sequence
<220> FEATURE:
```

<223> OTHER INFORMATION: Transcription factor probe PP108

<400> SEQUENCE: 108
gggccgggcg cagag                                              15

<210> SEQ ID NO 109
<211> LENGTH: 63
<212> TYPE: DNA
<213> ORGANISM: Artificial sequence
<220> FEATURE:
<223> OTHER INFORMATION: Hybridization probe MP02

<400> SEQUENCE: 109
ttccggctga gtcatcaagc gttccggctg agtcatcaag cgttccggct gagtcatcaa    60
gcg                                                               63

<210> SEQ ID NO 110
<211> LENGTH: 78
<212> TYPE: DNA
<213> ORGANISM: Artificial sequence
<220> FEATURE:
<223> OTHER INFORMATION: Hybridization probe MP04

<400> SEQUENCE: 110
acgggccgcg ggcggtcagt tcgatcacgg gccgcgggcg gtcagttcga tcacgggccg    60
cgggcggtca gttcgatc                                               78

<210> SEQ ID NO 111
<211> LENGTH: 69
<212> TYPE: DNA
<213> ORGANISM: Artificial sequence
<220> FEATURE:
<223> OTHER INFORMATION: Hybridization probe MP06-1

<400> SEQUENCE: 111
aaaaagaaca ccctgtacca gacaaaaga acaccctgta ccagacaaaa agaacaccct    60
gtaccagac                                                         69

<210> SEQ ID NO 112
<211> LENGTH: 54
<212> TYPE: DNA
<213> ORGANISM: Artificial sequence
<220> FEATURE:
<223> OTHER INFORMATION: Hybridization probe MP08

<400> SEQUENCE: 112
gcgcgttaat gagctgtggc gcgttaatga gctgtggcgc gttaatgagc tgtg         54

<210> SEQ ID NO 113
<211> LENGTH: 60
<212> TYPE: DNA
<213> ORGANISM: Artificial sequence
<220> FEATURE:
<223> OTHER INFORMATION: Hybridization probe MP10

<400> SEQUENCE: 113
tgcagattgc gcaatctgca tgcagattgc gcaatctgca tgcagattgc gcaatctgca   60

<210> SEQ ID NO 114
<211> LENGTH: 81
<212> TYPE: DNA
<213> ORGANISM: Artificial sequence
<220> FEATURE:
<223> OTHER INFORMATION: Hybridization probe MP12

-continued

```
<400> SEQUENCE: 114
aagagattaa ccaatcacgt acggtctaag agattaacca atcacgtacg gtctaagaga      60
ttaaccaatc acgtacggtc t                                                81

<210> SEQ ID NO 115
<211> LENGTH: 81
<212> TYPE: DNA
<213> ORGANISM: Artificial sequence
<220> FEATURE:
<223> OTHER INFORMATION: Hybridization probe MP14

<400> SEQUENCE: 115
tcagaaattg gctaataatc attgggttca gaaattggct aataatcatt gggttcagaa      60
attggctaat aatcattggg t                                                81

<210> SEQ ID NO 116
<211> LENGTH: 75
<212> TYPE: DNA
<213> ORGANISM: Artificial sequence
<220> FEATURE:
<223> OTHER INFORMATION: Hybridization probe MP16

<400> SEQUENCE: 116
tcactacgga accgttatgc ctgtatcact acggaaccgt tatgcctgta tcactacgga      60
accgttatgc ctgta                                                       75

<210> SEQ ID NO 117
<211> LENGTH: 81
<212> TYPE: DNA
<213> ORGANISM: Artificial sequence
<220> FEATURE:
<223> OTHER INFORMATION: Hybridization probe MP18

<400> SEQUENCE: 117
ctagctctct gacgtcaggc aatctctcta gctctctgac gtcaggcaat ctctctagct      60
ctctgacgtc aggcaatctc t                                                81

<210> SEQ ID NO 118
<211> LENGTH: 75
<212> TYPE: DNA
<213> ORGANISM: Artificial sequence
<220> FEATURE:
<223> OTHER INFORMATION: Hybridization probe MP20

<400> SEQUENCE: 118
ttgagaaagg gcgcgaaact taaatttgag aaagggcgcg aaacttaaat ttgagaaagg      60
gcgcgaaact taaat                                                       75

<210> SEQ ID NO 119
<211> LENGTH: 81
<212> TYPE: DNA
<213> ORGANISM: Artificial sequence
<220> FEATURE:
<223> OTHER INFORMATION: Hybridization probe MP22

<400> SEQUENCE: 119
tggcccccgc tcgccccgc tggatcctgg ccccgctcg ccccgctgg atcctggccc      60 ccgctcgccc ccgctggatc c                                                81

<210> SEQ ID NO 120
```

<210> SEQ ID NO 120
<211> LENGTH: 70
<212> TYPE: DNA
<213> ORGANISM: Artificial sequence
<220> FEATURE:
<223> OTHER INFORMATION: Hybridization probe MP24

<400> SEQUENCE: 120
aactttgatc aggtcactgt gacctgactt tggacaactt tgatcaggtc actgtgacct    60
gactttggac    70

<210> SEQ ID NO 121
<211> LENGTH: 93
<212> TYPE: DNA
<213> ORGANISM: Artificial sequence
<220> FEATURE:
<223> OTHER INFORMATION: Hybridization probe MP26

<400> SEQUENCE: 121
attcttatac ttcctcaagc agccctcctc cattcttata cttcctcaag cagccctcct    60
ccattcttat acttcctcaa gcagccctcc tcc    93

<210> SEQ ID NO 122
<211> LENGTH: 63
<212> TYPE: DNA
<213> ORGANISM: Artificial sequence
<220> FEATURE:
<223> OTHER INFORMATION: Hybridization probe MP28

<400> SEQUENCE: 122
tcgaacttcc tgctcgagat ctcgaacttc ctgctcgaga tctcgaactt cctgctcgag    60
atc    63

<210> SEQ ID NO 123
<211> LENGTH: 63
<212> TYPE: DNA
<213> ORGANISM: Artificial sequence
<220> FEATURE:
<223> OTHER INFORMATION: Hybridization probe MP30

<400> SEQUENCE: 123
gtacagccaa tacacaatcc ggtacagcca atacacaatc cggtacagcc aatacacaat    60
ccg    63

<210> SEQ ID NO 124
<211> LENGTH: 96
<212> TYPE: DNA
<213> ORGANISM: Artificial sequence
<220> FEATURE:
<223> OTHER INFORMATION: Hybridization probe MP32

<400> SEQUENCE: 124
ttgtagagta atatgaaact gaaagtactt cgttgtagag taatatgaaa ctgaaagtac    60
ttcgttgtag agtaatatga aactgaaagt acttcg    96

<210> SEQ ID NO 125
<211> LENGTH: 81
<212> TYPE: DNA
<213> ORGANISM: Artificial sequence
<220> FEATURE:
<223> OTHER INFORMATION: Hybridization probe MP34

<400> SEQUENCE: 125
agagttatca ctttctgtta tcaagtgaga gttatcactt tctgttatca agtgagagtt    60

```
atcactttct gttatcaagt g                                              81

<210> SEQ ID NO 126
<211> LENGTH: 82
<212> TYPE: DNA
<213> ORGANISM: Artificial sequence
<220> FEATURE:
<223> OTHER INFORMATION: Hybridization probe MP36

<400> SEQUENCE: 126
cgaattggat ctagaacatc ctgtacagat cctctagggt ccgaattgga tctagaacat   60
cctgtacaga tcctctaggg tc                                            82

<210> SEQ ID NO 127
<211> LENGTH: 75
<212> TYPE: DNA
<213> ORGANISM: Artificial sequence
<220> FEATURE:
<223> OTHER INFORMATION: Hybridization probe MP38

<400> SEQUENCE: 127
tagttgtacc aaagtacaag ctgagtagtt gtaccaaagt acaagctgag tagttgtacc   60
aaagtacaag ctgag                                                    75

<210> SEQ ID NO 128
<211> LENGTH: 66
<212> TYPE: DNA
<213> ORGANISM: Artificial sequence
<220> FEATURE:
<223> OTHER INFORMATION: Hybridization probe MP40

<400> SEQUENCE: 128
agtcaatttc attttcgctt ccagtcaatt tcattttcgc ttccagtcaa tttcattttc   60
gcttcc                                                              66

<210> SEQ ID NO 129
<211> LENGTH: 75
<212> TYPE: DNA
<213> ORGANISM: Artificial sequence
<220> FEATURE:
<223> OTHER INFORMATION: Hybridization probe MP42

<400> SEQUENCE: 129
tcaggcagca ggtgttgggg ggatctcagg cagcaggtgt tgggggatc tcaggcagca    60 ggtgttgggg ggatc                                                    75

<210> SEQ ID NO 130
<211> LENGTH: 75
<212> TYPE: DNA
<213> ORGANISM: Artificial sequence
<220> FEATURE:
<223> OTHER INFORMATION: Hybridization probe MP44

<400> SEQUENCE: 130
cgacagggtt attttagac cgatccgaca gggttatttt tagaccgatc cgacagggtt   60 attttagac cgatc                                                     75

<210> SEQ ID NO 131
<211> LENGTH: 78
<212> TYPE: DNA
<213> ORGANISM: Artificial sequence
<220> FEATURE:
```

<223> OTHER INFORMATION: Hybridization probe MP46

<400> SEQUENCE: 131

```
ggaagcagac cacgtggtct gcttccggaa gcagaccacg tggtctgctt ccggaagcag    60
accacgtggt ctgcttcc                                                  78
```

<210> SEQ ID NO 132
<211> LENGTH: 75
<212> TYPE: DNA
<213> ORGANISM: Artificial sequence
<220> FEATURE:
<223> OTHER INFORMATION: Hybridization probe MP48

<400> SEQUENCE: 132

```
ttatcatatt ggcttcaatc caaaattatc atattggctt caatccaaaa ttatcatatt    60
ggcttcaatc caaaa                                                     75
```

<210> SEQ ID NO 133
<211> LENGTH: 90
<212> TYPE: DNA
<213> ORGANISM: Artificial sequence
<220> FEATURE:
<223> OTHER INFORMATION: Hybridization probe MP50

<400> SEQUENCE: 133

```
tgtatgaaac aaattttcct ctttgggcgt tgtatgaaac aaattttcct ctttgggcgt    60
tgtatgaaac aaattttcct ctttgggcgt                                     90
```

<210> SEQ ID NO 134
<211> LENGTH: 81
<212> TYPE: DNA
<213> ORGANISM: Artificial sequence
<220> FEATURE:
<223> OTHER INFORMATION: Hybridization probe MP52

<400> SEQUENCE: 134

```
accagccgcc aagatggccg cggagcgacc agccgccaag atggccgcgg agcgaccagc    60
cgccaagatg gccgcggagc g                                              81
```

<210> SEQ ID NO 135
<211> LENGTH: 81
<212> TYPE: DNA
<213> ORGANISM: Artificial sequence
<220> FEATURE:
<223> OTHER INFORMATION: Hybridization probe MP54

<400> SEQUENCE: 135

```
ctccagtgac tcagcacagg ttccccactc cagtgactca gcacaggttc cccactccag    60
tgactcagca caggttcccc a                                              81
```

<210> SEQ ID NO 136
<211> LENGTH: 66
<212> TYPE: DNA
<213> ORGANISM: Artificial sequence
<220> FEATURE:
<223> OTHER INFORMATION: Hybridization probe MP56

<400> SEQUENCE: 136

```
gcctgggaaa gtcccctcaa ctgcctggga aagtcccctc aactgcctgg gaaagtcccc    60
tcaact                                                               66
```

-continued

<210> SEQ ID NO 137
<211> LENGTH: 66
<212> TYPE: DNA
<213> ORGANISM: Artificial sequence
<220> FEATURE:
<223> OTHER INFORMATION: Hybridization probe MP58

<400> SEQUENCE: 137
ttctagtgat tccattcga cattctagtg atttccattc gacattctag tgatttccat    60
tcgaca                                                               66

<210> SEQ ID NO 138
<211> LENGTH: 81
<212> TYPE: DNA
<213> ORGANISM: Artificial sequence
<220> FEATURE:
<223> OTHER INFORMATION: Hybridization probe MP60

<400> SEQUENCE: 138
ccccagcatg cttagacatg ttctgtaccc cagcatgctt agacatgttc tgtacccag    60 catgcttaga catgttctgt a                                              81

<210> SEQ ID NO 139
<211> LENGTH: 81
<212> TYPE: DNA
<213> ORGANISM: Artificial sequence
<220> FEATURE:
<223> OTHER INFORMATION: Hybridization probe MP62

<400> SEQUENCE: 139
cggtggtcac gcctcagtgc cccattccgg tggtcacgcc tcagtgcccc attccggtgg    60
tcacgcctca gtgccccatt c                                              81

<210> SEQ ID NO 140
<211> LENGTH: 78
<212> TYPE: DNA
<213> ORGANISM: Artificial sequence
<220> FEATURE:
<223> OTHER INFORMATION: Hybridization probe MP64

<400> SEQUENCE: 140
ctccaattag tgcatcaatc aattcgctcc aattagtgca tcaatcaatt cgctccaatt    60
agtgcatcaa tcaattcg                                                  78

<210> SEQ ID NO 141
<211> LENGTH: 84
<212> TYPE: DNA
<213> ORGANISM: Artificial sequence
<220> FEATURE:
<223> OTHER INFORMATION: Hybridization probe MP66

<400> SEQUENCE: 141
ttatttctta ttcatattca ggaagacatt atttcttatt catattcagg aagacattat    60
ttcttattca tattcaggaa gaca                                           84

<210> SEQ ID NO 142
<211> LENGTH: 60
<212> TYPE: DNA
<213> ORGANISM: Artificial sequence
<220> FEATURE:
<223> OTHER INFORMATION: Hybridization probe MP68

<400> SEQUENCE: 142

```
tgacctttga cctagttttg tgacctttga cctagttttg tgacctttga cctagttttg    60
```

<210> SEQ ID NO 143
<211> LENGTH: 81
<212> TYPE: DNA
<213> ORGANISM: Artificial sequence
<220> FEATURE:
<223> OTHER INFORMATION: Hybridization probe MP70

<400> SEQUENCE: 143

```
tgtagctaga acatcctgta caggatctgt agctagaaca tcctgtacag gatctgtagc    60
tagaacatcc tgtacaggat c                                              81
```

<210> SEQ ID NO 144
<211> LENGTH: 93
<212> TYPE: DNA
<213> ORGANISM: Artificial sequence
<220> FEATURE:
<223> OTHER INFORMATION: Hybridization probe MP72

<400> SEQUENCE: 144

```
cgagtgaact tcggtgaacc ctaccctcg acgagtgaac tttcggtgaa ccctaccctc     60
gacgagtgaa ctttcggtga accctaccct cga                                 93
```

<210> SEQ ID NO 145
<211> LENGTH: 78
<212> TYPE: DNA
<213> ORGANISM: Artificial sequence
<220> FEATURE:
<223> OTHER INFORMATION: Hybridization probe MP74

<400> SEQUENCE: 145

```
agctctctga cctctgacct gaagctagct ctctgacctc tgacctgaag ctagctctct    60
gacctctgac ctgaagct                                                  78
```

<210> SEQ ID NO 146
<211> LENGTH: 81
<212> TYPE: DNA
<213> ORGANISM: Artificial sequence
<220> FEATURE:
<223> OTHER INFORMATION: Hybridization probe MP76

<400> SEQUENCE: 146

```
tgtagacaag atttacggga aatgcactgt agacaagatt tacgggaaat gcactgtaga    60
caagatttac gggaaatgca c                                              81
```

<210> SEQ ID NO 147
<211> LENGTH: 64
<212> TYPE: DNA
<213> ORGANISM: Artificial sequence
<220> FEATURE:
<223> OTHER INFORMATION: Hybridization probe MP78

<400> SEQUENCE: 147

```
tcagtctaga catacttcag tctagacata cttcagtcta gacatacttc agtctagaca    60
tact                                                                 64
```

<210> SEQ ID NO 148
<211> LENGTH: 117
<212> TYPE: DNA
<213> ORGANISM: Artificial sequence
<220> FEATURE:
<223> OTHER INFORMATION: Hybridization probe MP80

-continued

```
<400> SEQUENCE: 148
gtgtctggct aaatgtctgg cttttgtctg gctctcgag tgtctggcta aatgtctggc      60
tttttgtctg gctctcgagt gtctggctaa atgtctggct ttttgtctgg ctctcga       117

<210> SEQ ID NO 149
<211> LENGTH: 63
<212> TYPE: DNA
<213> ORGANISM: Artificial sequence
<220> FEATURE:
<223> OTHER INFORMATION: Hybridization probe MP82

<400> SEQUENCE: 149
ctcgccccgc cccgatcgaa tctcgccccg ccccgatcga atctcgcccc gccccgatcg      60
aat                                                                   63

<210> SEQ ID NO 150
<211> LENGTH: 66
<212> TYPE: DNA
<213> ORGANISM: Artificial sequence
<220> FEATURE:
<223> OTHER INFORMATION: Hybridization probe MP84

<400> SEQUENCE: 150
agatgtccta atatggacat ccagatgtcc taatatggac atccagatgt cctaatatgg      60
acatcc                                                                66

<210> SEQ ID NO 151
<211> LENGTH: 75
<212> TYPE: DNA
<213> ORGANISM: Artificial sequence
<220> FEATURE:
<223> OTHER INFORMATION: Hybridization probe MP86

<400> SEQUENCE: 151
cacttacagg aatatgcata acatgcactt acaggaatat gcataacatg cacttacagg      60
aatatgcata acatg                                                      75

<210> SEQ ID NO 152
<211> LENGTH: 72
<212> TYPE: DNA
<213> ORGANISM: Artificial sequence
<220> FEATURE:
<223> OTHER INFORMATION: Hybridization probe MP88

<400> SEQUENCE: 152
gatctaggaa ttcccagaag gatcgatcta ggaattccca gaaggatcga tctaggaatt      60
cccagaagga tc                                                         72

<210> SEQ ID NO 153
<211> LENGTH: 99
<212> TYPE: DNA
<213> ORGANISM: Artificial sequence
<220> FEATURE:
<223> OTHER INFORMATION: Hybridization probe MP90

<400> SEQUENCE: 153
ctagctcatc atttcgggga aatcaggctc tagctagctc atcatttcgg ggaaatcagg      60
ctctagctag ctcatcattt cggggaaatc aggctctag                            99

<210> SEQ ID NO 154
```

<211> LENGTH: 63
<212> TYPE: DNA
<213> ORGANISM: Artificial sequence
<220> FEATURE:
<223> OTHER INFORMATION: Hybridization probe MP92

<400> SEQUENCE: 154

```
ggattgaatt cctagaaatc tggattgaat tcctagaaat ctggattgaa ttcctagaaa     60
tct                                                                  63
```

<210> SEQ ID NO 155
<211> LENGTH: 60
<212> TYPE: DNA
<213> ORGANISM: Artificial sequence
<220> FEATURE:
<223> OTHER INFORMATION: Hybridization probe MP94

<400> SEQUENCE: 155

```
gttccttttc tgggaaatac gttccttttc tgggaaatac gttccttttc tgggaaatac     60
```

<210> SEQ ID NO 156
<211> LENGTH: 75
<212> TYPE: DNA
<213> ORGANISM: Artificial sequence
<220> FEATURE:
<223> OTHER INFORMATION: Hybridization probe MP96

<400> SEQUENCE: 156

```
tcctacctca ttttatatgc tctgctccta cctcatttta tatgctctgc tcctacctca     60
ttttatatgc tctgc                                                     75
```

<210> SEQ ID NO 157
<211> LENGTH: 96
<212> TYPE: DNA
<213> ORGANISM: Artificial sequence
<220> FEATURE:
<223> OTHER INFORMATION: Hybridization probe MP98

<400> SEQUENCE: 157

```
tctcctcagg tcatgacctg aatcttacga tctctcctca ggtcatgacc tgaatcttac     60
gatctctcct caggtcatga cctgaatctt acgatc                              96
```

<210> SEQ ID NO 158
<211> LENGTH: 87
<212> TYPE: DNA
<213> ORGANISM: Artificial sequence
<220> FEATURE:
<223> OTHER INFORMATION: Hybridization probe MP100

<400> SEQUENCE: 158

```
agctctctga cctcctgtga cctgaagcta gctctctgac ctcctgtgac ctgaagctag     60
ctctctgacc tcctgtgacc tgaagct                                        87
```

<210> SEQ ID NO 159
<211> LENGTH: 69
<212> TYPE: DNA
<213> ORGANISM: Artificial sequence
<220> FEATURE:
<223> OTHER INFORMATION: Hybridization probe MP102

<400> SEQUENCE: 159

```
ggtgtaggcc acgtgaccgg gtgggtgtag gccacgtgac cgggtgggtg taggccacgt     60
gaccgggtg                                                            69
```

<210> SEQ ID NO 160
<211> LENGTH: 84
<212> TYPE: DNA
<213> ORGANISM: Artificial sequence
<220> FEATURE:
<223> OTHER INFORMATION: Hybridization probe MP104

<400> SEQUENCE: 160
agctctctga cctccttgac ctgaagctag ctctctgacc tccttgacct gaagctagct    60
ctctgacctc cttgacctga agct    84

<210> SEQ ID NO 161
<211> LENGTH: 60
<212> TYPE: DNA
<213> ORGANISM: Artificial sequence
<220> FEATURE:
<223> OTHER INFORMATION: Hybridization probe MP106

<400> SEQUENCE: 161
tctagaaaat tccagtctag aaaattccag tctagaaaat tccagtctag aaaattccag    60

<210> SEQ ID NO 162
<211> LENGTH: 60
<212> TYPE: DNA
<213> ORGANISM: Artificial sequence
<220> FEATURE:
<223> OTHER INFORMATION: Hybridization probe MP108

<400> SEQUENCE: 162
gggccgggcg cagaggggcc gggcgcagag gggccgggcg cagaggggcc gggcgcagag    60